US012661496B2

(12) United States Patent
Soykan et al.

(10) Patent No.: US 12,661,496 B2
(45) Date of Patent: Jun. 23, 2026

(54) TRANSMITTING AND RECEIVING ANTENNAS FOR TRANSFERRING POWER TO IMPLANTED MEDICAL DEVICES

(71) Applicant: Corisma Cardiovascular, Hamden, CT (US)

(72) Inventors: Orhan Soykan, Hamden, CT (US); Michael Edward Theran, Bethany, CT (US); Jim Kelley, Hamden, CT (US); Mark Kelley, Hamden, CT (US)

(73) Assignee: Corisma Cardiovascular, Hamden, CT (US)

( * ) Notice: Subject to any disclaimer, the term of this patent is extended or adjusted under 35 U.S.C. 154(b) by 498 days.

(21) Appl. No.: 18/177,290

(22) Filed: Mar. 2, 2023

(65) Prior Publication Data

US 2024/0165395 A1 May 23, 2024

Related U.S. Application Data

(63) Continuation-in-part of application No. 18/056,749, filed on Nov. 18, 2022, now Pat. No. 12,485,272, which is a continuation-in-part of application No. PCT/US2022/035172, filed on Jun. 27, 2022, said application No. 18/056,749 is a continuation-in-part of application No. PCT/US2022/035177, filed on Jun. 27, 2022.

(60) Provisional application No. 63/217,388, filed on Jul. 1, 2021, provisional application No. 63/318,559, filed on Mar. 10, 2022, provisional application No. 63/318,560, filed on Mar. 10, 2022.

(51) Int. Cl.
*A61M 60/148* (2021.01)

(52) U.S. Cl.
CPC ..... *A61M 60/148* (2021.01); *A61M 2209/088* (2013.01)

(58) Field of Classification Search
CPC .......... A61M 2209/088; A61M 60/178; A61M 60/216; A61M 60/873
See application file for complete search history.

(56) References Cited

U.S. PATENT DOCUMENTS 5,370,509 A * 12/1994 Golding .............. F04D 29/0467
417/423.1
10,729,834 B2 * 8/2020 Bonde ................. A61M 60/515
(Continued)

*Primary Examiner* — Paula J Stice
(74) *Attorney, Agent, or Firm* — Farber LLC

(57) ABSTRACT

Systems, devices and methods are provided for supporting cardiac function. One system comprises an implantable intracardiac device comprising a motor and a pump, an external energy source and a transmitting resonator comprising a magnetic coil and configured to receive a first level of power from the external energy source and transmit a second level of power through an outer skin surface of the patient. The system further comprises a receiving resonator configured for implantation within the patient, comprising a magnetic coil and configured to transmit a third level of power to the motor within the implanted device. The third level of power is at least 40% of the first level of power, thereby ensuring that the pump will continuously pump blood through the heart at a sufficient rate regardless of any changes in the system, such as power loss due to transmission inefficiencies and/or changes in the relative positions between the transmitting and receiving coils.

27 Claims, 32 Drawing Sheets

(56)         References Cited

U.S. PATENT DOCUMENTS

| | | | |
|---|---|---|---|
| 2009/0216149 A1* | 8/2009 | Neff ........................ | A61B 5/031 |
| | | | 600/561 |
| 2013/0289334 A1* | 10/2013 | Badstibner ............. | H01F 38/14 |
| | | | 307/104 |
| 2013/0310630 A1* | 11/2013 | Smith ................. | A61M 60/538 |
| | | | 600/16 |
| 2018/0311425 A1* | 11/2018 | Tuseth ................ | A61M 60/818 |
| 2021/0283391 A1* | 9/2021 | Hansen ................... | H02J 50/12 |
| 2021/0283392 A1* | 9/2021 | Schilling ............. | H02J 7/00034 |
| 2022/0139614 A1* | 5/2022 | Diekhans ................ | H01F 38/14 |
| | | | 307/104 |

* cited by examiner

904

900

902

914

910

912

924

920

922

934

930

932

944        942

940

954        952

950

964        962

960

974            972            970

984            982            980

TRANSMITTING AND RECEIVING ANTENNAS FOR TRANSFERRING POWER TO IMPLANTED MEDICAL DEVICES

CROSS-REFERENCE TO RELATED APPLICATIONS

This application is a continuation-in-part of U.S. application Ser. No. 18/056,749, filed Nov. 18, 2022, which is a continuation-in-part of International Applications Nos. US 2022/35172 and US 2022/35177, filed Jun. 27, 2022, which claim the benefit of U.S. Provisional Application Ser. No. 63/217,388, filed Jul. 1, 2021, 63/318,560, filed Mar. 10, 2022 and U.S. Pat. No. 63,318,559, filed Mar. 10, 2022, the entire disclosures of which are incorporated herein by reference in their entirety for all purposes.

FIELD

The present disclosure generally relates to systems and methods for wirelessly transferring power to implanted medical devices and more particularly to systems for transferring power to medical devices designed for supporting cardiac function.

BACKGROUND

In recent decades, the confluence of advances in medical and surgical capabilities, biomedical engineering, and electronic and computer miniaturization has produced a revolution in the field of active implantable medical devices, with resultant increases in human longevity and quality of life. Examples of implantable medical devices include artificial hearts, implantable heart monitors and defibrillators, pacemakers, artificial heart valves, neurostimulators, ventricular assist devices, extracorporeal membrane oxygenation devices (ECMO) and the like.

A ventricular assist device (VAD) is a medical device that partially or completely replaces the function of a damaged or failing heart. VADs typically assist the heart and do not completely take over cardiac function or require removal of the patient's heart. A particular VAD may be used to assist the patient's right ventricle (RVAD), left ventricle (LVAD) or both ventricles (BiVAD), depending on the needs of the patient.

VADs have an outer casing, which may be a collapsible stent design, and typically include an axial or radial flow pump within the casing to support cardiac function. The casing is typically implanted into one of the lower chambers of the heart, such as the left ventricle, where it receives blood. The pump includes a rotor with impeller blades that rotate and add work to the blood, propelling it from the device to the aorta for distribution to the rest of the body. Recently, systems have been designed to wirelessly power and control the axial pump, thereby obviating the need to implant a power source within the patient. In addition, VADs can be implanted using minimally invasive procedures without the need for open heart surgery.

Although VADs may sometimes be intended for short term use, for example, to provide post-operative assistance to a surgically repaired heart or as a bridge while awaiting a transplant, VADs are increasingly being used as a long-term solution. For example, VADs are now being implanted in patients suffering from congestive heart failure and for destination therapy (DT) for patients with heart failure who are no longer responding to optimal medical management and are not candidates for heart transplant surgery. The broadened use criteria of VADs coupled with a growing imbalance of transplant candidates and available hearts have resulted in an increased frequency of LVAD implantation and longer durations of support. As LVAD utilization grows, expectations of an improved and stable quality of life have become increasingly important as patients desire to return to a normal lifestyle and experience minimal disruptions from their LVADs.

Conventional VADs require a percutaneous driveline, wherein a biocompatible cable extends through the patient's body to connect the VAD to a power source and system controller. These "trans-dermal" drivelines have many disadvantages and negative quality-of-life impacts for a patient. Moreover, due to improvements in VAD technology and the increasingly long-term use of VADs, the most common cause of complications requiring patient hospitalization and/or affecting patient mortality is no longer failure of the VAD itself. Rather, the most common complications result from exit site infection (ESI) associated with the percutaneous driveline. ESI can result in repeated hospitalization, increased patient pain and suffering, and significant medical expenses incurred.

The risk of ESI largely results from the need to continuously provide power through the protective barrier provided by the patient's skin to the implanted medical device for long-term operation of the device. It would, therefore, be advantageous to provide power wirelessly to an implanted medical device such as a VAD.

Prior attempts to transfer power wirelessly through a patient's skin use conventional inductive coupling techniques, e.g., magnetic coils on the inner and outer surfaces of the skin. However, conventional inductive coupling energy transfer has several drawbacks. For example the magnetic coils require very close separation distance in order to effectively transfer power through the patient's skin. In addition, restrictions on misalignment between the transmitting and receiving coils limit the practicality of conventional inductive coupling.

In an attempt to solve these issues, magnetically coupled resonators (MCRs) have been developed that use dynamic power management control to maintain high energy transfer efficiency over relatively long distances (e.g., typically over 1 meter). In addition, relay resonators have been developed to further increase the distance between the implanted receiver coil and the transmitter coil.

While these magnetically coupled resonators have shown promise, they still suffer from a number of challenges and drawbacks for long-term implantation of VADs. For example, the power received by the implanted pump must continuously remain at or above a threshold level in order for the pump to continuously pump a sufficient quantity of blood to effectively assist heart function. Since the patient is typically relying on the VAD to provide sufficient heart function, even a momentary drop in this power level could cause complications and/or adverse health consequences for the patient.

At the same time, power must be transferred from the transmitting coil (or a relay resonator) through the air, the patient's outer skin surface and various tissue structures in the patient to the internal receiver. The initial power produced by the external power source is reduced as it passes through all of these substances. In addition, power may be reduced or lost due to various deviations between the relative positions and/or orientations of the receiver and transmitter coils, such as the distance between the coils, the offset between the center of the coils, the substance between the coils and the angle between the coils. All of these factors may be subject to constant change as the patient moves around and changes the relative position and orientation of the coils with simple daily activities, such as standing up, walking, lying down, sitting down, exercising and the like.

What is needed, therefore, are improved devices for supporting cardiac function that overcome the challenges and deficiencies with existing devices. It would be particularly desirable to provide intracardiac devices that provide a constant level of wireless power transfer to the implanted device regardless of power transmission inefficiencies and/ or reduced coupling between the transmitter and receiver coils.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present description provides systems, devices and methods for transmitting wireless power to a medical device implanted within a patient. The systems and methods are particular useful for transferring power to medical devices designed for supporting cardiac function, such as devices designed for longer term implantation in patients that are, for example, suffering from congestive heart failure for destination therapy (DT), bridge to transplant therapy (BTT) and for any patients with heart failure who are no longer responding to optimal medical management and are not candidates for heart transplant surgery. However, it will be recognized that the devices and methods described herein may also be used for shorter term "acute" use as, for example, mechanical circulatory support devices (MCS) to provide hemodynamic support to patients who present with cardiogenic shock and other disorders.

In one aspect, a system for supporting cardiac function in a patient comprises a housing configured for implantation into a human heart or vascular system and comprising at least a motor and a pump. The system further comprises an external power source, a transmitting antenna and a receiving antenna configured for implantation within the patient. The external power source transmits a first level of power to the transmitting antenna and the transmitting antenna is configured to transmit a second level of power through an outer skin surface of the patient. The receiving antenna is configured to receive the second level of power and to transmit a third level of power to the housing. The third level of power is at least 40% of the first level of power, preferably at least 50% of the first level of power. Thus, the overall power transfer efficiency of the system (i.e., receiver output/ transmitter input) is at least 40%, which ensures that the implanted pump will receive sufficient power to continuously pump blood through the heart.

In embodiments, the system maintains the third level of power at least 50% of the first level of power when the transmitting coil is positioned a certain distance away from the receiving coil. In certain applications, the transmitting and receiving coils are designed to optimally transfer power at a distance of about 2 cm therebetween. For example, this distance may be the thickness of the skin and subcutaneous fat on the outer skin of a patient. In certain embodiments, the system is configured to maintain the third level of power at least 50% of the first level of power when the coils are positioned away from each other up to 4 cm, and/or when the coils are positioned closer to each other or less than 2 cm. This ensures that the pump will continue to operate in the event that, for example, the patient does not position the transmitting coil an optimal distance from the implanted receiving coil.

In embodiments, the controller also maintains the third level of power at least 50% of the first level of power when a center of the transmitting coil is offset a certain distance from a center of the receiving coil. In certain applications, the transmitting and receiving coils are designed to optimally transfer power with a center offset of zero (i.e., the centers of the coils are substantially aligned). In certain embodiments, the system is configured to maintain the third level of power at least 50% of the first level of power when the centers of the coils are offset by up to 4 cm. This ensures that the pump will continue to operate in the event that, for example, the patient does not properly align the transmitting coil with the implanted receiver coil.

This dynamic coupling between the transmitting and receiving coils compensates for reduced coupling between the antennas and/or other power loss inefficiencies in the system. This ensures that the pump within the implanted device will continuously pump blood through the heart at a sufficient rate regardless of any changes in the system (e.g., such as changes in the relative position and/or orientations of the transmitting and receiving coils) that would otherwise reduce the level of power received by the motor. This minimizes complications and/or adverse health consequences that would otherwise occur with a momentary or longer-term reduction in this power.

In embodiments, the system further comprises a controller coupled to the transmitting antenna and configured to control the transmitting and receiving antennas such that the third level of power remains at or above a threshold level. In preferred embodiments, the controller is configured to maintain the third level of power substantially constant. The specific level of power required by the implant will depend on the efficiency of the motor and the pump in transferring this power to blood flowing through the pump. In certain embodiments, the first level of power is about 20 Watts to about 40 Watts, preferably about 30 Watts. The second level of power is about 17.5 Watts to about 35 Watts, preferably about 25 Watts. The third level of power is about 5 Watts to about 20 Watts, preferably about 10 Watts.

In certain embodiments, the controller is configured to adjust the first level of power if the efficiency of the system drops below 50% or if the received power level drops below a predetermined amount, such as 6 Watts. This can occur in some instances, for example, if the patient moves the transmitting coil to a location that is greater than 4 cm from the receiving coil, the centers of the coils are offset by a distance of greater than 4 cm or other factors. In this embodiment, the controller automatically adjusts the first level of power to ensure that the third level of power delivered to the housing is between about 5 Watts to about 20 Watts, preferably about 10 Watts.

In embodiments, the transmitting and receiving coils are configured to have a specific absorption rate (SAR) in the outer skin surface of about 1.5 Watts/kg or less. This reduces or eliminates any damage to the cellular tissue between, or around, the transmitting and receiving coils.

In embodiments, the transmitting and receiving antenna may include one or more magnetic coils, preferably two magnetic coils. The transmitting and receiving coils each comprise a housing with an outer surface and a coil comprising a substantially spiral winding on the outer surface. In some embodiments, the coil is a continuous winding. In other embodiments, the coil comprises two or more discontinuous windings (i.e., multiple windings on the outer surface of the housing that are not directly connected with each other). These discontinuous windings may each form a substantially spiral shape, a circular or semi-circular shape (i.e., a concentric design) or they may form this spiral or concentric shape together as a unit. In certain embodiments, the discontinuous windings are substantially concentric with each other. In some embodiments, the windings are semi-circular.

In an exemplary embodiment, the transmitting coil(s) have a diameter of less than about 20 cm. In certain embodiments, the transmitting coil(s) are flexible and capable of movement relative to the receiving coil. The transmitting coil(s) may comprise any suitable material, such as polyimide, fiberglass-reinforced epoxy (e.g., FR4) or the like. In certain embodiments, the coil(s) comprises a loop outer diameter of about 50 mm to about 110 mm and a coil outer diameter of about 100 mm to about 120 mm. The trace width of the transmitting coil(s) is about 2.2 mm to about 2.7 mm, preferably about 2.5 mm to about 2.6 mm and the pitch is from about 3 mm to about 10 mm, preferably about 4.5 mm to about 7.2 mm (center to center), although it will be recognized that other configurations may be employed.

In embodiments, the receiving coil(s) will preferably have a diameter of less than about 10 cm, preferably between about 7 cm to about 10 cm. In certain embodiments, the receiving coil(s) are flexible and capable of movement relative to the transmitting coil. The coil(s) may comprise any suitable material, such as polyimide, fiberglass-reinforced epoxy (e.g., FR4) or the like. In certain embodiments, the coil(s) comprise a loop outer diameter of about 60 mm to about 80 mm and a coil outer diameter of about 100 mm to about 120 mm. The trace width of the receiving coil(s) about 2.2 mm to about 2.7 mm, preferably about 2.5 mm to about 2.6 mm and the pitch is from about 3 mm to about 10 mm, preferably about 4.5 mm to about 7.2 mm (center to center), although it will be recognized that other configurations may be employed.

In embodiments, the spiral windings on the coils preferably have about 4 turns to about 7 turns. In some embodiments, the spiral windings have 4 turns. The spiral windings may comprise two or more discontinuous windings each having between about 1 to 2 turns.

In one embodiment, the implantable device comprises one or more sensors for continuously measuring the third level of power received at the housing and optionally the temperatures of the various parts within the housing (i.e., at the motor or at the coil). These sensor(s) may be, for example, housed within the implant and coupled to the power electronics provided to the motor. The sensor(s) may be coupled to an internal controller (either directly through wired connections or wirelessly). The internal controller receives this data related to the second level of the power and transmits it to an external controller, which modulates one or more of the parameters of the wireless power transmission based on this data such that the power received by the motor remains substantially constant or at least above the threshold level.

The transmitting antenna (or a relay resonator coupled to the transmitting antenna) may reside in a housing that is configured to be attached to, or worn, by the patient. The receiving antenna may be implanted in a suitable location within the patient, such as a subcutaneous location within the patient near the outer skin surface. This limits the physical distance between the internal and external coils, which reduces power loss inefficiencies therebetween and minimizes changes in the relative position and orientation between the transmitting and receiving coils.

The system may further comprise a user interface that includes one or more indicators coupled to the controller that provide an alert when the wearable device is not positioned at the optimal distance and/or orientation relative to the receiver, whether the substance existing between the coils has changed (i.e., such as the substance of the user's clothing or other items) and/or that the second level of power is below the threshold level. The indicators may be visual, audible, tactile (e.g., vibration) or the like, and they may be housed on, or within, the wearable device or wirelessly coupled to the wearable device, for example, on a separate mobile device or the like. The user interface provides immediate feedback to the patient and/or the healthcare professional that the wearable device should be repositioned to establish sufficient power transfer to the implant.

In certain embodiments, the receiving antenna comprises a first magnet and the transmitting resonator comprises a second magnet. The first and second magnets are configured to cooperate with each other to optimize a position of the transmitting antenna relative to the receiving antenna. This minimizes relative movement between the receiving and transmitting coils as the patient moves with daily activities, such as sitting, standing up, walking or exercising.

In one embodiment, the system includes one or more position indicators coupled to the controller and the receiving and/or transmitting antennas The position indicators are configured to determine a distance between the magnetic coils in the receiving and transmitting antennas and to transmit this data to the controller. The controller is configured to adjust various parameters of the power generation and transmission to adjust for changes in this distance. For example, the controller may adjust the first level of power applied to the transmitting antenna if this distance increases. Alternatively, the controller may adjust other factors related to the power generation and transmission to account for this change, such as the amplifier frequency, the impedance of the system and the like.

In another embodiment, the system further comprises one or more center position indicators coupled to the controller and the receiving and transmitting antennas. The position indicators are configured to determine a positional offset between a center of the magnetic coil in the receiving antenna and a center of the magnetic coil in the transmitting antenna and to transmit this data to the controller. The controller is configured to adjust various parameters of the power generation and transmission to adjust for changes in this positional offset.

In yet another embodiment, the system further comprises one or more angle indicators coupled to the controller and the receiving and transmitting antennas. The angle indicators are configured to determine an angle between the magnetic coils in the receiving and transmitting antennas and to transmit this data to the controller. The controller is configured to adjust various parameters of the power generation and transmission to adjust for changes in this angle.

The position, angle and/or center position indicators may include sensors that indicate the absolute position or orientation of the coil within the transmitter. In other embodiments, the sensors may indicate the position or orientation of the transmitter coil relative to the receiver coil. Suitable sensors may include capacitive displacement sensors, eddy-current sensors, Hall effect sensors, inductive sensors, laser doppler sensors, linear variable differential transformers (LVDTs), photodiode arrays, piezo-electric transducers, position encoders, potentiometers, optical proximity sensors, magnetic angle sensors, TMR, GMR or AMR angle sensors, orientation sensors and the like. Furthermore, the information relating to the angle and the relative position of the coils could be obtained from the RF signal received by the receiver or the RF power reflected back to the transmitter or a combination of the two. The sensors may be coupled to an external device or controller, an internal controller or both. The controller(s) are configured to compare the position and orientation of the transmitter and receiver coils with the power delivered to the motor within the pump to, for example, determine if the wearable device is positioned correctly on the patient (i.e., at the optimal distance, angle and/or coil center offset to achieve an acceptable power transfer therebetween).

In certain embodiments, the transmitter and receiving antennas form a magnetically coupled resonator (MCR) by matching a resonance frequency between the transmitter resonator and the receiver resonator. MCRs induce power transfer between two components through a matching of the resonance frequency between a source resonator and a receiver resonator. A controller may be operable to receive data from sensor(s) coupled to the resonators, and to control the operating parameters to optimize the energy transfer efficiency in the MCR. In other embodiments, the transmitter or the receiver or both may contain impedance matching schemes, such as pi-networks, quarter or half wavelength transmission lines, RLC networks or similar. The system may further include an internal controller coupled to the receiving antenna. The internal controller comprises a power source, such as a rechargeable battery, a motor driver for transferring the power to the implant and associated electronics, such as memory, telemetry and the like. The internal controller may further include one or more sensors that detect a variety of operational parameters for the pump, such as the power transmitted to the pump, the pump speed, the maximum output pressure, the negative intake pressure, motor current, motor temperature and the like.

In certain embodiments, the implant comprises a housing configured for implantation into a right atrium of the patient. The housing comprises an inlet and an outlet spaced longitudinally from the inlet, the inlet and the outlet defining a primary blood flow path from a left atrium through at least a portion of the housing to an aorta. The housing comprises a motor coupled to, or disposed within, the housing and an impeller coupled to the motor for pumping blood from the first inlet to the outlet of the housing through the primary blood flow path.

In this embodiment, the implant bypasses the left ventricle by drawing freshly oxygenated blood from the left atrium and propelling this blood directly into the aorta, thereby reducing the pre-load on the left ventricle. Since the pump is implanted in the right atrium (or right atrium appendage), any blood clots that form on the pump will not break away and pass into the aorta and the arteries supplying blood to the brain, thereby eliminating the potential for a thrombotic stroke. In addition, in certain instances wherein the entry port is the descending aorta, the internal pressure within the right atrium is lower than any other chamber of the heart, which decreases the stresses and loads on the blood pump, thereby reducing bleeding events, mechanical failure and/or wear on the pump components over time.

In another embodiment, the implant comprises an axial flow pump having an elongate housing with first and second ends, an internal surface, a first inlet for blood disposed between the first and second ends and an outlet spaced longitudinally from the first inlet. The first inlet and the outlet define a primary blood flow path through the housing. The pump includes a rotatable element, such as a rotor, disposed within the housing and spaced from the internal surface to define a clearance therebetween. An impeller is coupled to the rotor for propelling blood from the first inlet to the outlet of the housing along the primary blood flow path. The housing includes a second inlet fluidly coupled to the clearance between the rotor and the housing to define a secondary flow path through the clearance. The blood passing through the secondary flow path continuously flushes the clearance between the rotor and the housing to minimize the formation and/or growth of blood clots and/or to remove heat generated by the rotor. This design, therefore, substantially reduces the risk of thrombosis within the pump or in the patient's heart or vascular system.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 15E is a perspective view of a rotor for the axial flow pump of FIG. 15D;

FIG. 15F is an enlarged view of one portion of the rotor of FIG. 14D;

DETAILED DESCRIPTION OF THE PREFERRED EMBODIMENTS

Figure 1:
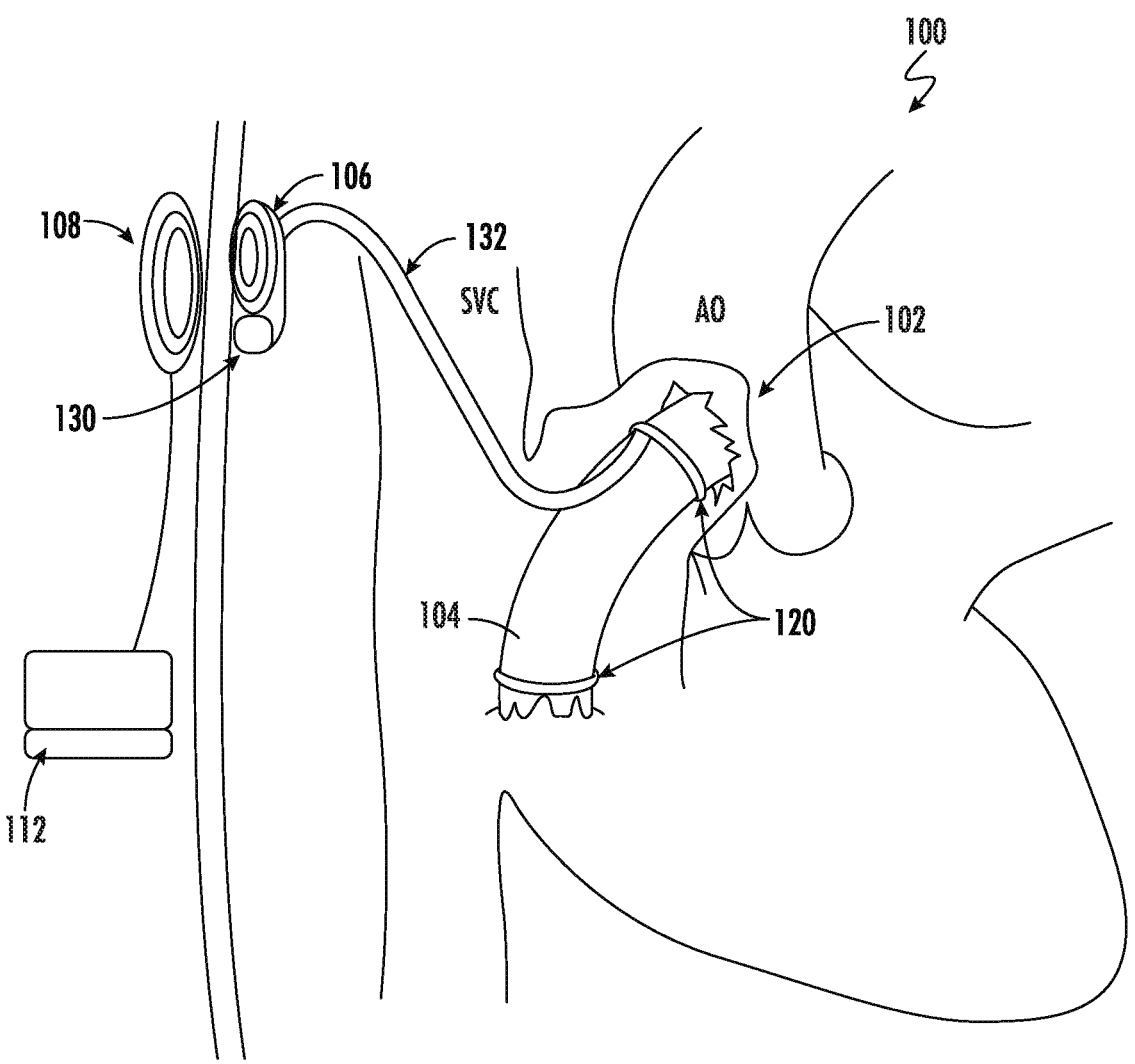
FIG. 1 is a schematic depicting an exemplary ventricular assist system.

Particular embodiments of the present disclosure are described hereinbelow with reference to the accompanying drawings; however, it is to be understood that the disclosed embodiments are merely exemplary of the disclosure and that the disclosure may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail. It should be understood also that the drawings are not drawn to scale and are not intended to represent absolute dimensions or relative size. Instead, the drawings help to illustrate the concepts described herein.

The present description provides systems, devices and methods for transmitting wireless power to a medical device implanted within a patient. The systems and methods are particular useful for transferring power to medical devices designed for supporting cardiac function. In the representative embodiments, the devices are implantable intracardiac devices, such a ventricular assist devices (VADs) for assisting or replacing cardiac function, such as in the case of ventricular failure. The intracardiac devices are particular useful for longer term implantation in patients suffering from congestive heart failure, for destination therapy (DT), bridge to transplant therapy (BTT) and for any patients with heart failure who are no longer responding to optimal medical management and are not candidates for heart transplant surgery. However, it will be recognized that the devices of the present disclosure may also be used as mechanical circulatory support devices (MCS) to provide hemodynamic support to patients who present with, for example, cardiogenic shock. In addition, the intracardiac devices may be used in other applications, such as artificial hearts, ECMO devices, implantable heart monitors and defibrillators, pacemakers, or other intracardiac devices.

In the representative embodiments, the intracardiac devices may include an axial flow pump designed to support cardiac function by pumping blood from the left atrium to the patient's arterial system. The pump is housed within a casing that may, or may not, have a collapsible stent design depending on the method of implantation. The pump may be wirelessly powered and controlled. In some embodiments, the pump may be implanted using minimally invasive procedures without the need for open heart surgery.

In certain cases, the intracardiac device may include inflow and outflow valves that are closeable to seal the pump from a subject's anatomy. Closing the inflow and outflow valves modulate flow and allow for sealing of the pump, prolonging the life of the pump when not in use.

In some embodiments, the intracardiac devices may include a cleaning system configured to introduce and circulate cleaning solutions and therapeutics to the pump. For example, the cleaning system includes an access port that enables rapid circulation of a cleaning solution into the pump. Coupling the cleaning system to the inflow and outflow valves allows for maintenance of the pump while implanted without biological or chemical fouling (such as thrombosis, intimal hyperplasia, encrustation, and the like).

Referring now to FIG. 1, an exemplary ventricular assist system 100 includes an intracardiac device 102 that is implanted into a heart chamber. Intracardiac device 102 comprises an outer casing 104, which in some embodiments may comprise a substantially cylindrical stent body. Casing or stent 104 includes an internal lumen running between two open ends and an axial pump (not shown) between the two open ends. Stent 104 can have a mesh or wire construction, such that stent 104 can be collapsible into a narrow configuration to facilitate insertion and expandable at a site of implantation. In certain embodiments, stent 104 comprises a covering, which can have a biological (such as pericardium or engineered tissue scaffold), artificial (such as a polymer), or a biological and artificial hybrid construction.

Figure 2:
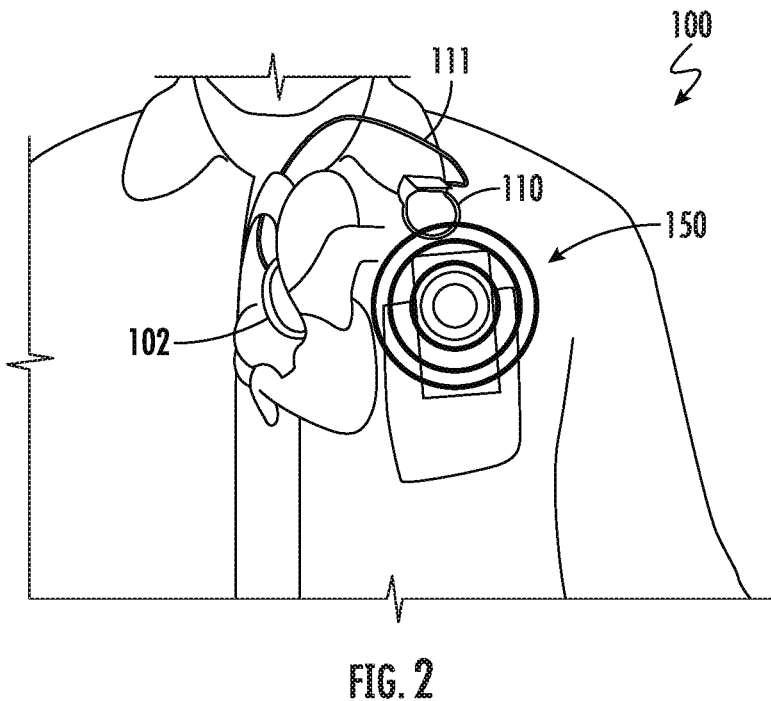
FIG. 2 illustrates an exemplary VAD implanted within a patient with a wireless power source.
Figure 3:
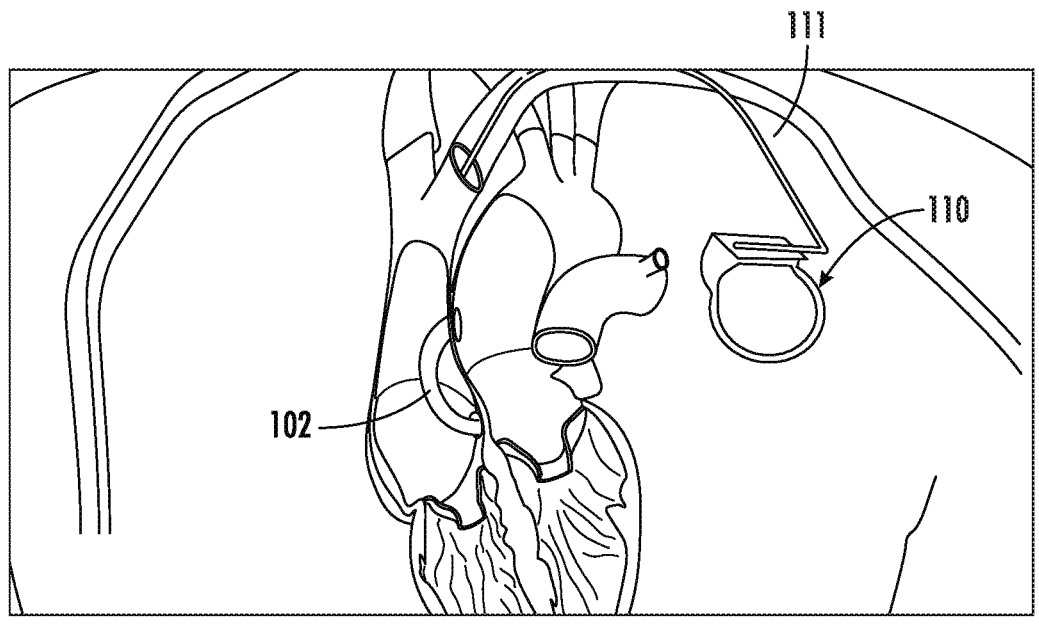
FIG. 3 illustrates the implanted portions of the VAD of FIG. 2.

In some embodiments, stent 104 may include a valve 120 positioned at each open end and a cleaning system 130 fluidly connected to device 102 via a lumen 132. The various components of device 102, including each valve 130, the axial pump, and cleaning system 130, can be powered by a receiving coil 106 wirelessly receiving electromagnetic energy from a transmitting coil 108 and a battery (discussed in further detail below). Coil 106 and/or cleaning system 130 may be housed within an internal controller 110 that is implanted within the patient (see FIG. 2). In certain embodiments, device 102 further comprises an external controller 112 configured to communicate with the wireless transmitter 108 to activate and modulate each of the components of device 102 (discussed in more detail below). For example, external controller 112 can be configured to wirelessly open and close each valve 120, to activate and modulate the speed of the axial pump, and to activate cleaning system 130. A more complete description of suitable intracardiac devices can be found in International Publication No. WO 2019/ 241556 and U.S. Pat. Nos. 9,919,088, 10,172,987, 10,729, 834 and 10,293,090 the complete disclosures of which are incorporated herein by reference in their entirety for all purposes.

FIGS. 2-5 illustrate the representative intracardiac system 100 implanted in a patient. As shown, device 102 is coupled via a suitable connector 111 to controller 110, which may be implanted subcutaneously in any suitable location known to those of skill in the art. Controller 110 includes wireless electronics, receiving coil 106 and a power source, such as a battery. System 100 may further include a wireless power transmitter 150 that includes transmitting coil 108 to communicate power and data to controller 110. Power transmitter 150 also may wirelessly communicate information to external patient and clinician devices to enable continuous and remote patient and system monitoring. A more complete description of suitable wireless power systems can be found in U.S. Pat. Nos. 11,090,481, 9,919,088 and 9,415,149, the complete disclosures of which are incorporated herein by reference in their entirety for all purposes.

Of course, it will be recognized that the systems and methods of the present disclosure may be used with other intracardiac systems. For example, power transmitter 150 may be directly coupled to controller 110, or they may both be incorporated into the same device. This device may be implanted subcutaneously within the patient, or it may be implanted within the patient's heart. Alternatively, the power transmitter and controller may be incorporated into intracardiac device 102.

Intracardiac device 102 may be implanted into a heart chamber through open surgical procedures, percutaneously, endoscopically, or through a minimally invasive procedure, for example, by advancing a catheter through the patient's vascular system. The device 102 may be inserted through a puncture in the cardiac wall and introduced into the heart such that casing 104 sealingly closes the puncture hole while device 102 is in the interior of the heart and a cannula or outlet tube coupled to device 102 is outside the heart.

In one minimally invasive procedure, casing 104 is in the form of a collapsible stent (or "graft") that is implanted into the right atrium, the superior vena cava (SVC) and/or the inferior vena cava (IVC) of the patient's heart. An arterial catheter is advanced through the ascending aorta into the SVC and then through the right atrium into the left atrium. The anchors may be deployed at the atrial septum and the SVC. The catheter is then withdrawn from the right atrium to deploy the graft between the anchors.

In another minimally invasive procedure, a catheter is advanced through an artery of the patient to deliver device 102 into a heart chamber, such as the right atrium. The intracardiac device 102 is then advanced through a femoral vein into the heart chamber and implanted therein. Delivering the intracardiac device into the heart chamber through the vein allows for use of a smaller bore arterial catheter, thereby minimizing stress on the femoral artery or aortic arch and reducing internal bleeding, bruising and other potential complications associated with a purely arterial approach.

In one such embodiment, the intracardiac device is advanced through an entry port and through the femoral vein and then coupled to the arterial catheter within the femoral vein, the inferior vena cava (IVC) or the heart chamber (e.g., via transcaval manipulation of the arterial catheter). The arterial catheter is then withdrawn into the heart chamber to advance the intracardiac device into the heart chamber. In this "in vivo" approach, the device is coupled to the catheter within the patient's body.

In an exemplary embodiment of the "in vivo" approach, a guidewire or similar device is advanced through the femoral vein into the IVC or the right atrium of the patient's heart. The venous guidewire is then coupled to a guidewire in the arterial catheter via a snare or similar device and the arterial guidewire is withdrawn through the femoral vein. The arterial catheter guidewire is then coupled to the intracardiac device and retracted back into the right atrium with the device. The device is then withdrawn into the arterial catheter with the guide wire and implanted within the heart chamber.

In another embodiment, the arterial catheter is advanced from the heart chamber through the femoral vein to an exit portal of the femoral vein. The intracardiac device is then coupled to the catheter externally of the patient's body and the catheter is withdrawn back through the femoral vein into the heart chamber to advance the intracardiac device into the heart chamber. In this "ex vivo" approach, the device is coupled to the catheter outside of the patient's body.

In an exemplary embodiment of the "ex vivo" approach, the intracardiac device is manually positioned within the arterial catheter exterior to the patient's body. The arterial catheter is then withdrawn back through the femoral vein into the heart chamber and the device is implanted therein.

In both the "in vivo" and "ex vivo" embodiments, the intracardiac device is positioned within the arterial catheter by moving the distal end portion of the arterial catheter from a collapsed position, where it is sized for advancement through an artery, to an expanded position, where it is sized to receive the intracardiac device. In certain embodiments, the arterial catheter is expanded while maintaining its steerability within the vasculature of the patient.

Figure 4:
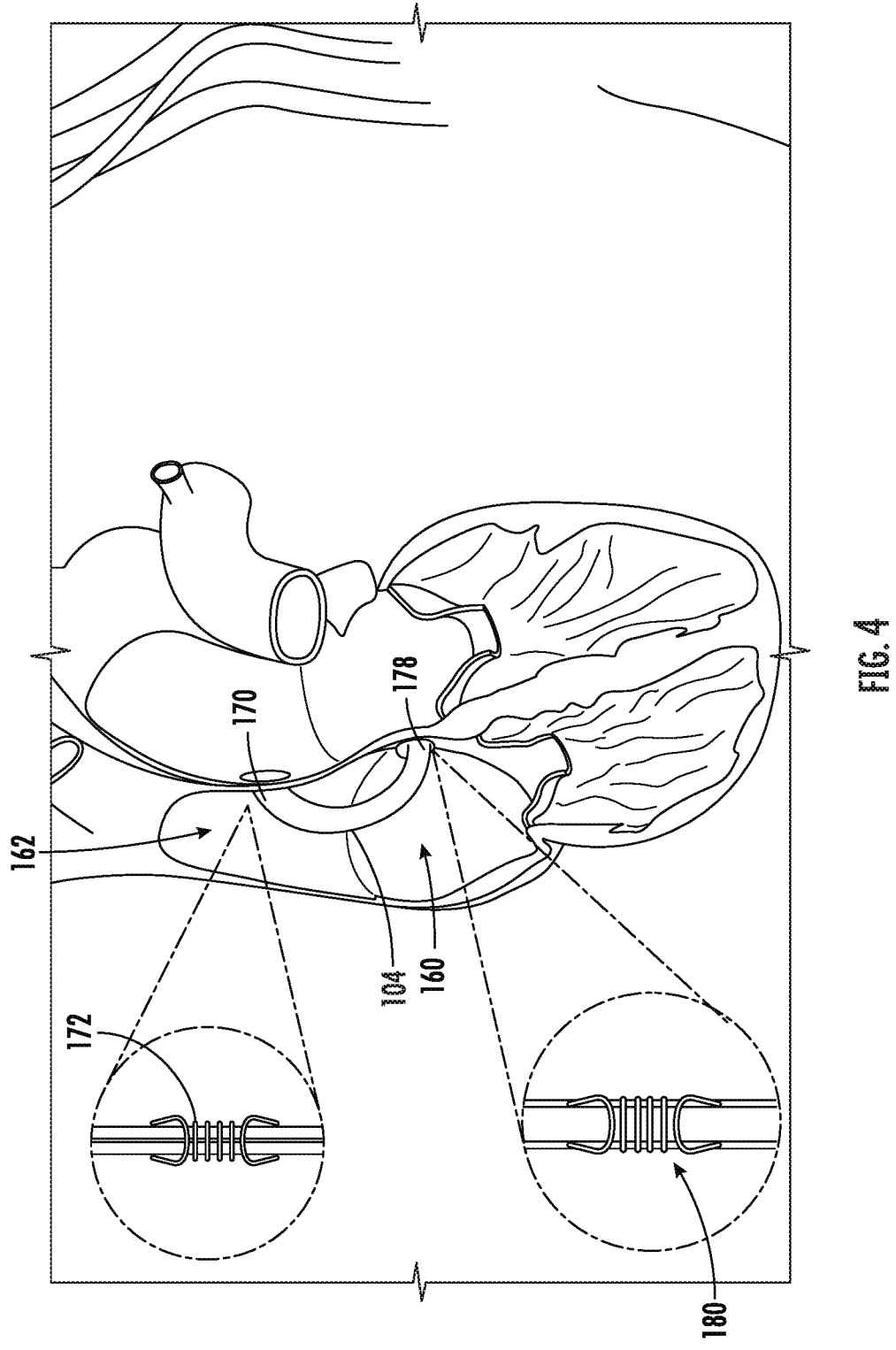
FIG. 4 illustrates an intracardiac device with first and second anchors for securing the VAD in the right atrium of a patient's heart.
Figure 5:
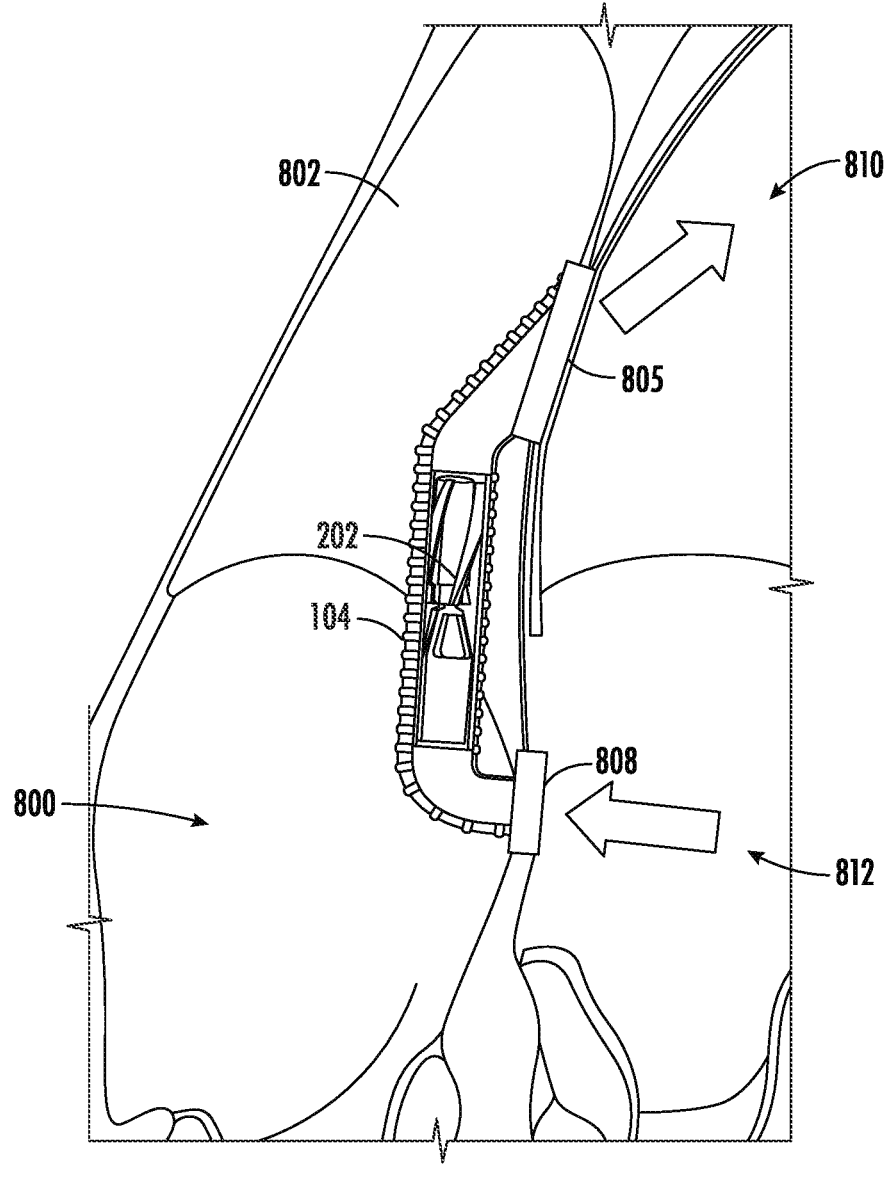
FIG. 5 is a cross-sectional view of the intracardiac device of FIG. 4.

FIGS. 4 and 5 illustrate a representative stent 104 implanted within the right atrium 160 and the SVC 162 of a patient. As shown, stent 104 includes a first end 170 coupled to a first anchor 172 and a second end 178 coupled to a second anchor 180. First anchor 172 is preferably positioned such that first end 170 of stent 104 outflows into the aorta 182 and second anchor 180 is positioned such that second end 178 receives inflow from the left atrium 184. The axial pump 200, which includes a motor 201 and an impeller 203 (discussed in detail below) is housed within stent 104 between first and second ends 170, 178 to pump blood from the left atrium 184 into the aorta 182 and throughout the patient's body. Thus, the pump essentially bypasses the left ventricle by drawing freshly oxygenated blood from the left atrium 184 and propelling this blood into aorta 182, thereby reducing the pre-load on the left ventricle.

Since device 200 is implanted in the right atrium 160, any blood clots that form on the pump will remain in the right atrium 160 and will not break away and pass into the aorta 182 and the arteries supplying blood to the brain, thereby eliminating the potential for a thrombotic stroke. In addition, the internal pressure within the right atrium is lower than any other chamber of the heart, which decreases the stresses and loads on the blood pump, thereby reducing bleeding events, mechanical failure and/or wear on the pump components over time.

Since there are no valves between the right atrium 160 and the SVC 162, at least a portion of device 200 may extend from the right atrium 160 and into the SVC or IVC 162. This provides a larger combined space for device 200 and allows device to be longer than it otherwise would be, if, for example, it were implanted in the left atrium or the left ventricle. This additional length allows for the design of a more efficient pump. In addition, since the SVC 162 extends alongside the aorta 182, there are multiple locations along the SVC 162 in which to create an anastomosis for passing the anchor 172 therethrough.

In certain embodiments, anchors 172, 180 are coupled to, or integral with, stent 104 prior to deployment of stent 104 into the patient's heart. In these embodiments, stent 104 and anchors 172, 180 are advanced together through the femoral vein and into the right atrium. In other embodiments, anchors 172, 180 are separate from stent 104. In these embodiments, anchors 172, 180 are configured for deployment through the vascular system such that anchors 172, 180 may be secured to suitable locations within the patient's heart. Stent 104 may be coupled to anchors 172, 180 in vivo after they have been secured to such locations in the heart. In yet another embodiment, one of the anchors is secured to, or integral with, stent 104 prior to deployment of stent 104 within the heart. In this embodiment, the other anchor is secured within the heart, and then stent 104 and the anchor are advanced into the right atrium together. Stent 104 is coupled to the anchor that is already secured to the heart, and the other anchor is secured to complete deployment of stent 104.

Figure 6:
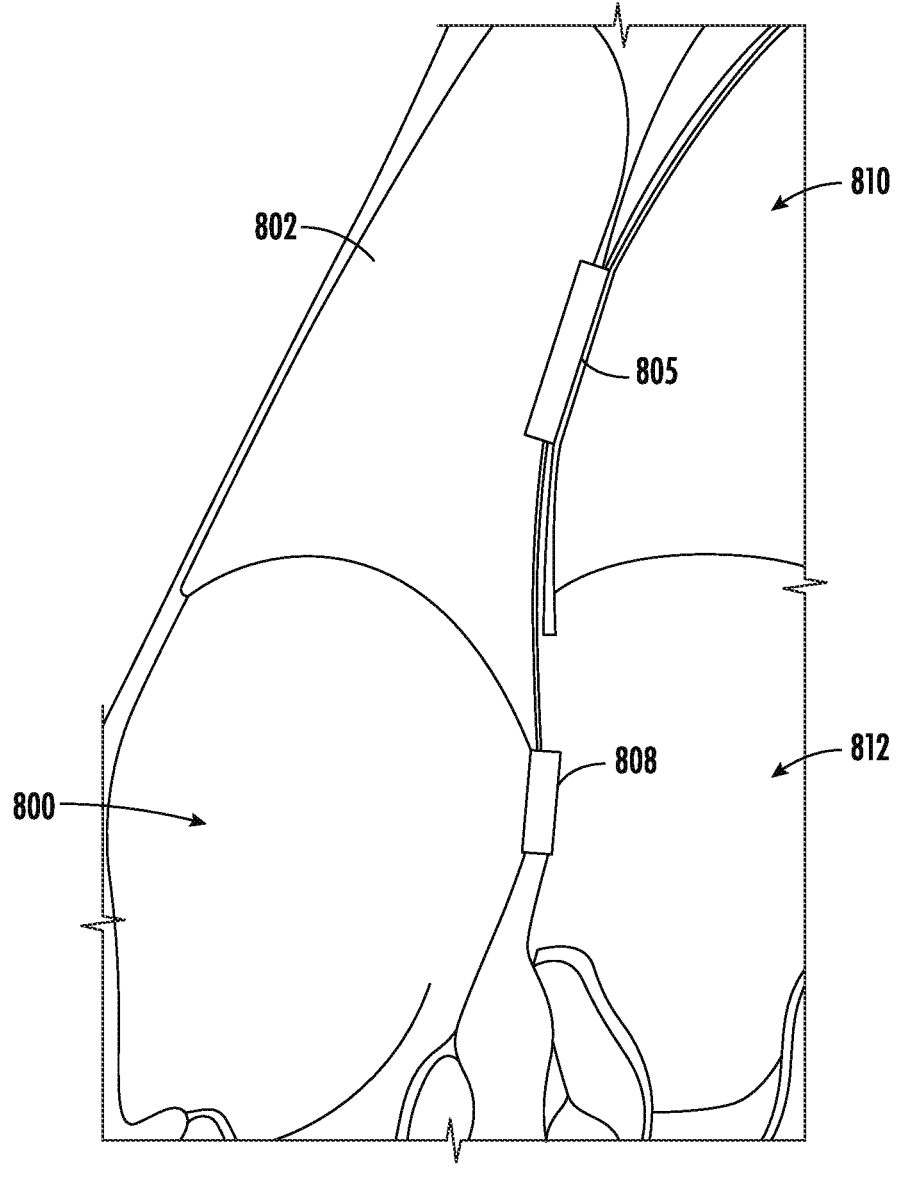
FIG. 6 illustrates the first and second anchors prior to implantation of the stent.

Referring now to FIGS. 6-13, systems and methods for implanting stent 104 within the patient's heart according to the present disclosure will now be described. As shown in FIG. 6, in one embodiment, anchors 805 and 808 are first deployed by advancing a venous catheter (not shown) through, for example, the femoral vein and coupling anchors 805, 808 to the heart wall in methods known by those of skill in the art. In other embodiments, one or both of the anchors 805, 808 may be deployed together with stent 104, as discussed above.

Figure 7:
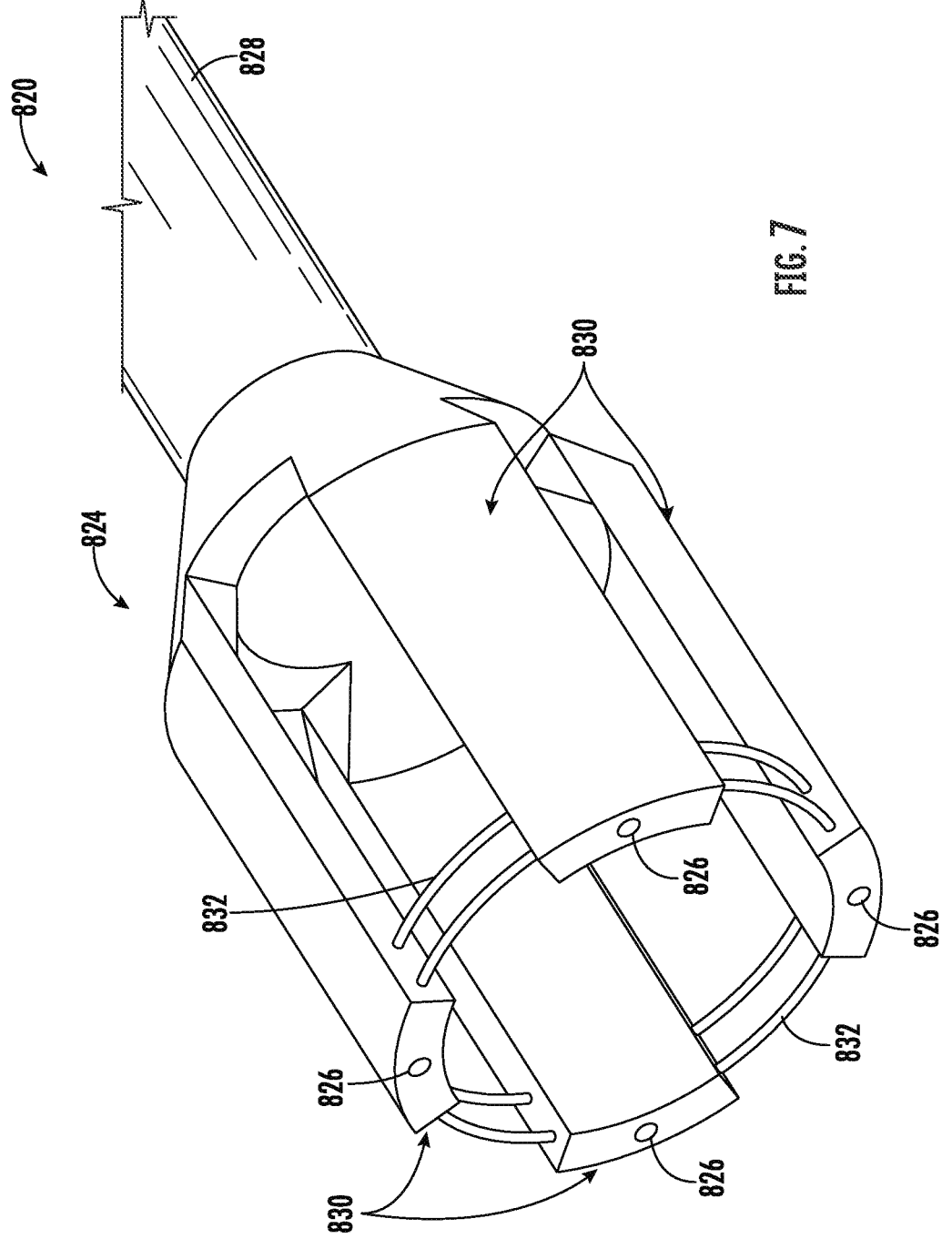
FIG. 7 illustrates a distal end of an arterial catheter according to the present disclosure.

FIG. 7 illustrates a distal end 824 of an arterial catheter 820 according to one embodiment of the present invention. As shown, catheter 820 includes a plurality of steering cables 826 extending through a shaft 828 to distal end 824. In the preferred embodiment, catheter 820 includes four steering cables 826 positioned around the catheter shaft 828 about 90 degrees from each other, although it will be recognized that other embodiments are possible. For example, catheter 820 may include two cables on opposite corners (i.e., 180 degrees separation), or three corners positioned generally around the shaft at about 120 degrees from each other or other known implementations. Steering cables 826 are each coupled to an actuator (not shown) at the proximal end of shaft 828 that allows the operator to steer catheter 820 in multiple degrees of freedom (DOF). Cables 828 typically operator through a push-pull actuation that provides the multiple DOF to catheter 820.

In one embodiment, distal end 824 may be expanded in order to accommodate stent 104 and/or one of the anchors 805, 808 therein (as discussed below). As shown in FIG. 7, distal end 824 includes a plurality of arms 830 that can be expanded and separated from each other. Arms 830 are expanded such that cables 828 remain at substantially parallel angles to each other in the expanded configuration. This ensures that the steering capabilities of catheter 820 will not be compromised when distal end 824 is expanded to accommodate stent 104.

In one embodiment, this is accomplished with a plurality of expansion straps 832 extending between arms 830. Straps 832 allow arms 830 to expand outward while constraining distal end 824 such that steering cables 828 expand an equal amount from the central longitudinal axis of shaft 828. Straps 832 may comprise cables, elastomeric straps, or other mechanisms that have sufficient flexibility to allow such expansion, while maintaining sufficient constraint upon distal end to expand arms 830 equally in a radial direction from its central longitudinal axis.

Figure 8:
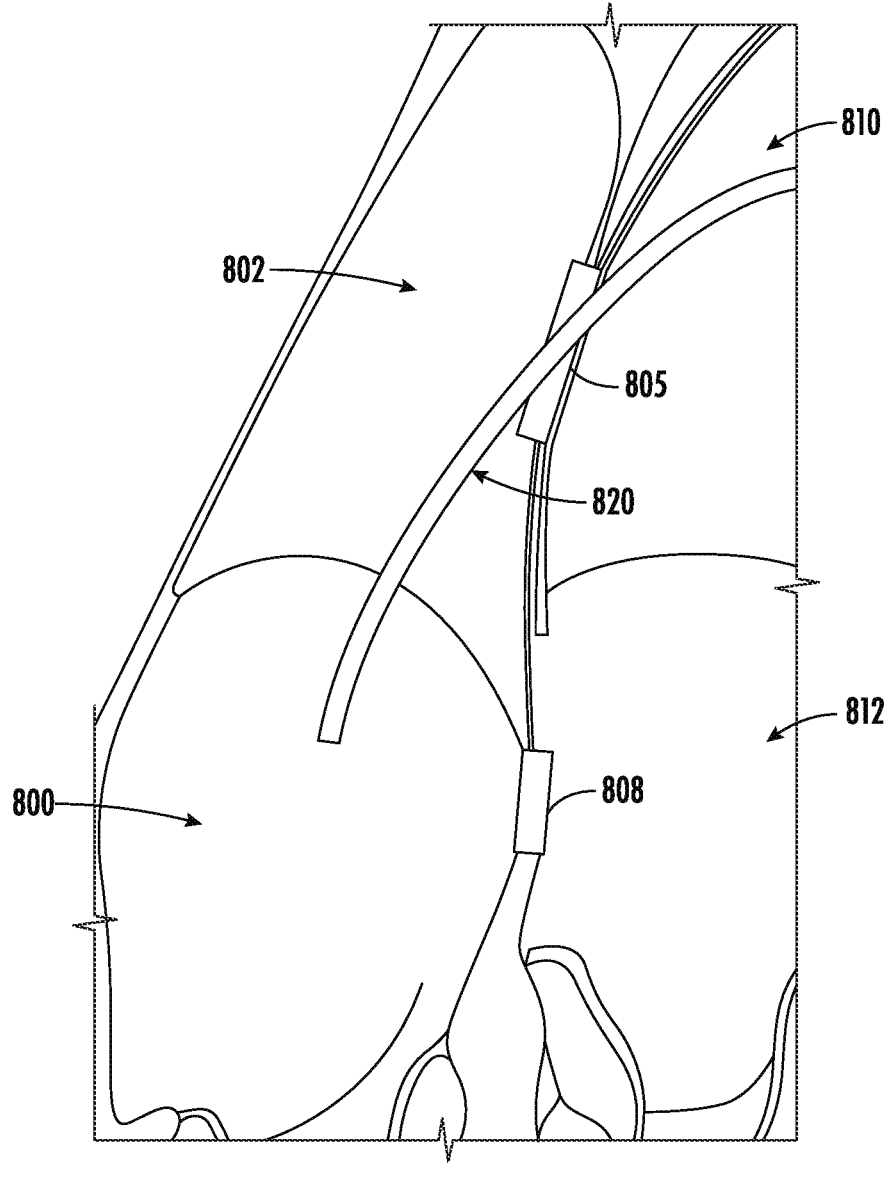
FIG. 8 illustrates a step in a method of the present disclosure that includes advancing an arterial catheter through the first anchor from the aorta into the superior vena cava.

Referring now to FIG. 8, arterial catheter 820 is then advanced through the femoral artery (preferably via a transcaval puncture) into the aorta 810, and then through first anchor 805 into the superior vena cava (SVC) 802. Passing catheter 820 through anchor 806 minimizes bleeding from the aorta 810 into the SVC 802. A guidewire (not shown) remaining from the deployment of the venous catheter discussed above may be used to guide catheter 810 into the right location.

Figure 9:
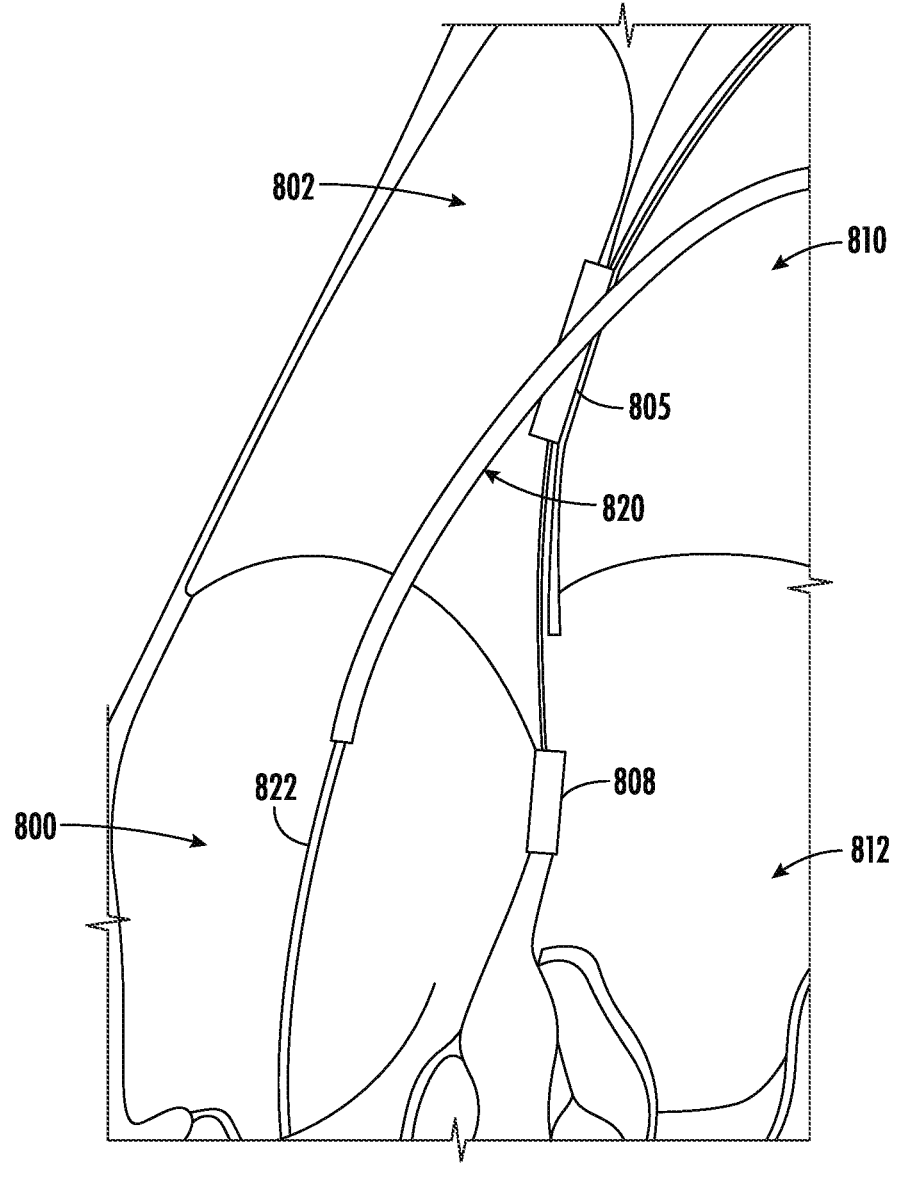
FIG. 9 illustrates one embodiment of the present disclosure wherein the catheter of FIG. 7 is coupled to a guidewire and advanced through a femoral vein.

Referring now to FIG. 9, a connection is then made between catheter 820 and the femoral vein (not shown) such that stent 104 may be advanced through the femoral vein and into the right atrium 800. In one embodiment (the "in vivo" approach), a guidewire (not shown) is advanced through an entry portal, such as an access sheath (not shown) in the femoral vein and advanced into the femoral vein, the inferior vena cava (not shown) or right atrium 800. A venous catheter (not shown) may then be advanced over guidewire 822 into the femoral vein, inferior vena cava or right atrium 800. The venous catheter preferably includes a snare or similar capture element configured for grasping arterial catheter 820, or a guidewire 822 within arterial catheter 820. In the preferred embodiments, arterial catheter 820 is coupled to the capture element of the venous catheter at a location distal of the femoral vein (e.g., within the inferior vena cava or the right atrium). The arterial catheter guidewire 822 may then be pulled through the femoral vein and the access sheath so that stent 104 may be attached to this guidewire.

In another embodiment (the "ex vivo" approach), arterial catheter 820 is advanced from the right atrium through the femoral vein such that it exits the access sheath of the vein. The stent 104 may then be manually positioned within the distal end of catheter 820 exterior of the patient.

Figure 10:
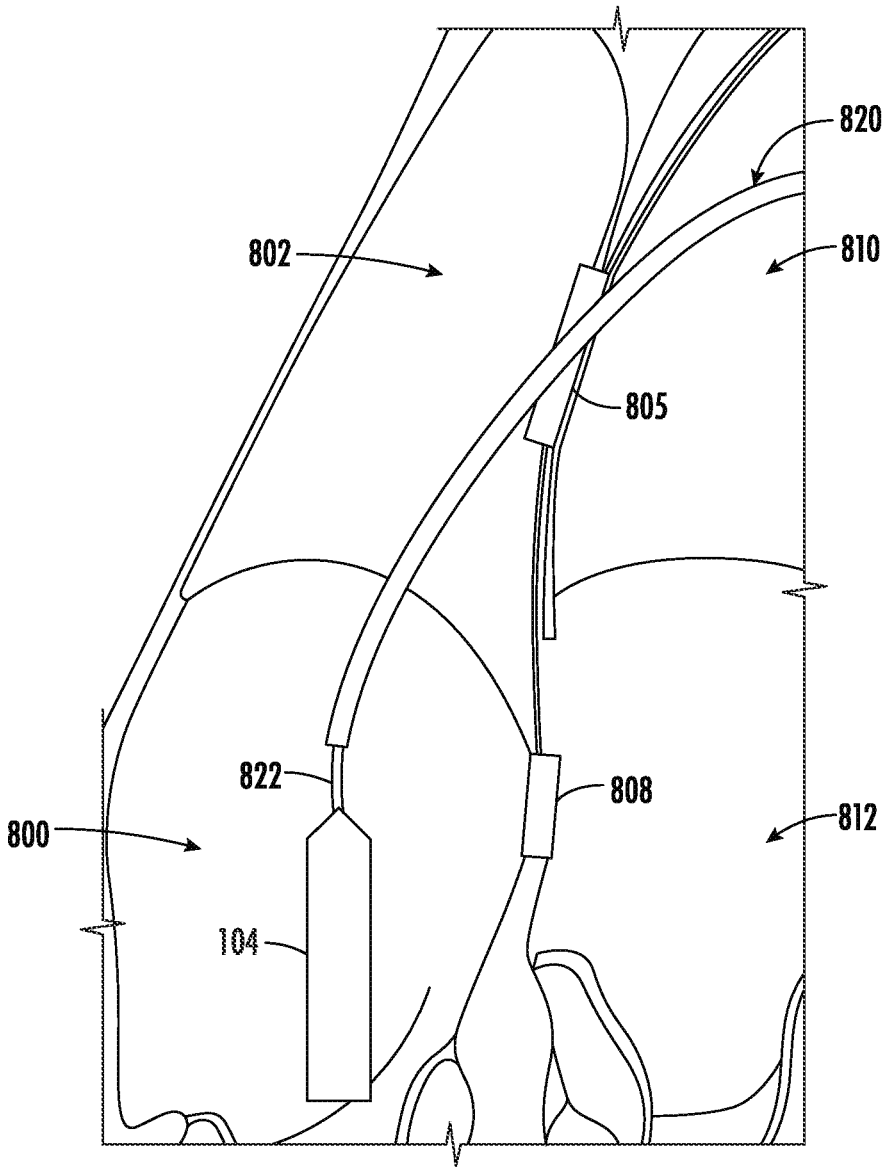
FIG. 10 illustrates the stent being advanced into the right atrium with the arterial catheter.

Referring now to FIG. 10, in either of the above described embodiments, stent 104 may then be pulled through the femoral vein and into right atrium 800 with arterial catheter 820. In the "in vivo" approach, the arterial catheter guidewire 822 is retracted back into the arterial catheter 820 until stent 104 is located in the right atrium (catheter 820 remains in the right atrium throughout this procedure). In the "ex vivo" approach, catheter 820 is retracted until its distal end is located in right atrium 800.

Figure 11:
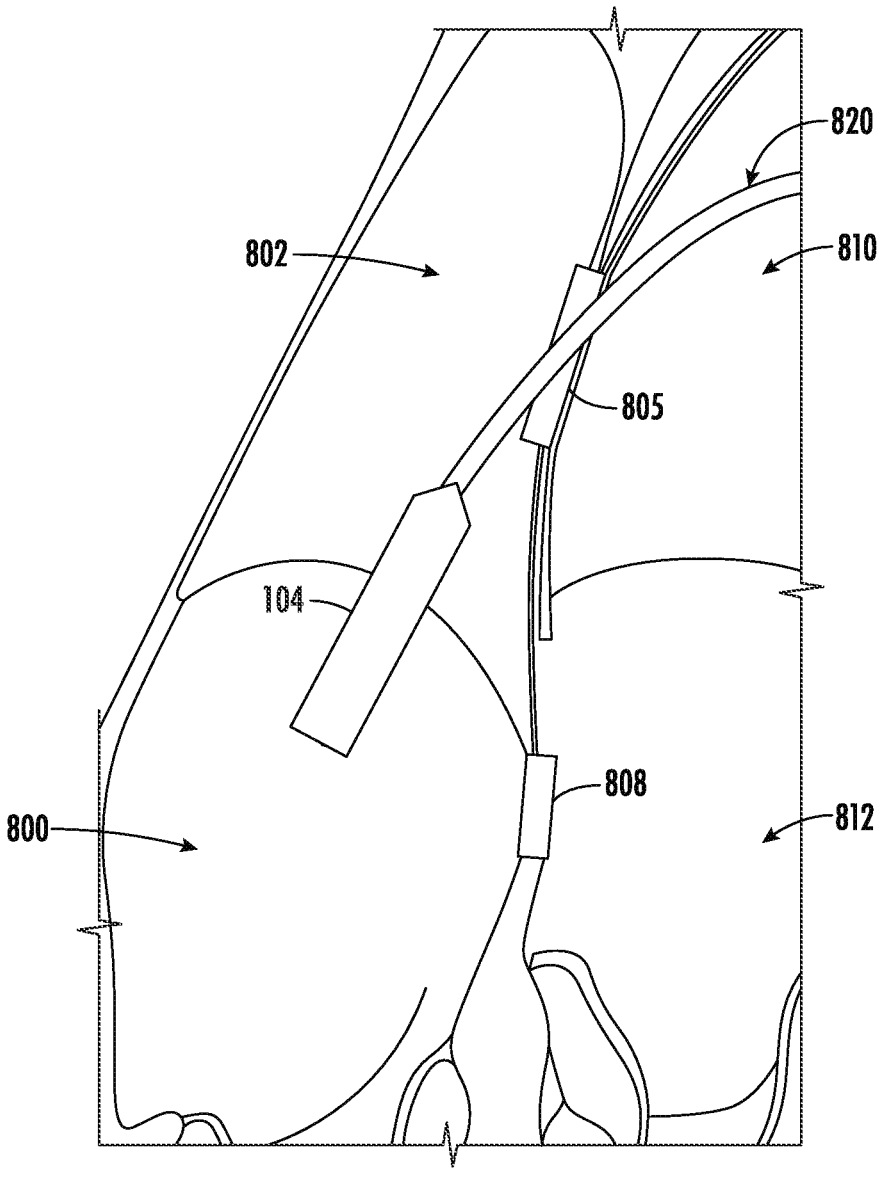
FIG. 11 illustrates the stent being pulled into the arterial catheter.

Referring now to FIG. 11, stent 104 is then pulled or advanced into arterial catheter 820 (note that this step has already occurred in the "ex vivo" approach). Typically, the stent 104 has a larger diameter than catheter 820 even in the collapsed configuration of stent 104 (this is because axial pump 202 has a substantially fixed outer diameter that cannot be collapsed). In certain embodiments, stent 104 has a diameter of about 27 fr in its collapsed configuration and arterial catheter 920 has a diameter of about 18 fr in its collapsed position. Thus, in order to capture stent 104 within catheter 820, the distal end 824 of catheter 820 is split open to accommodate stent 104 (see FIG. 7). In the preferred embodiment, catheter 820 retains its steering capability after the distal end has been split open, as described above in reference to FIG. 7.

Figure 12:
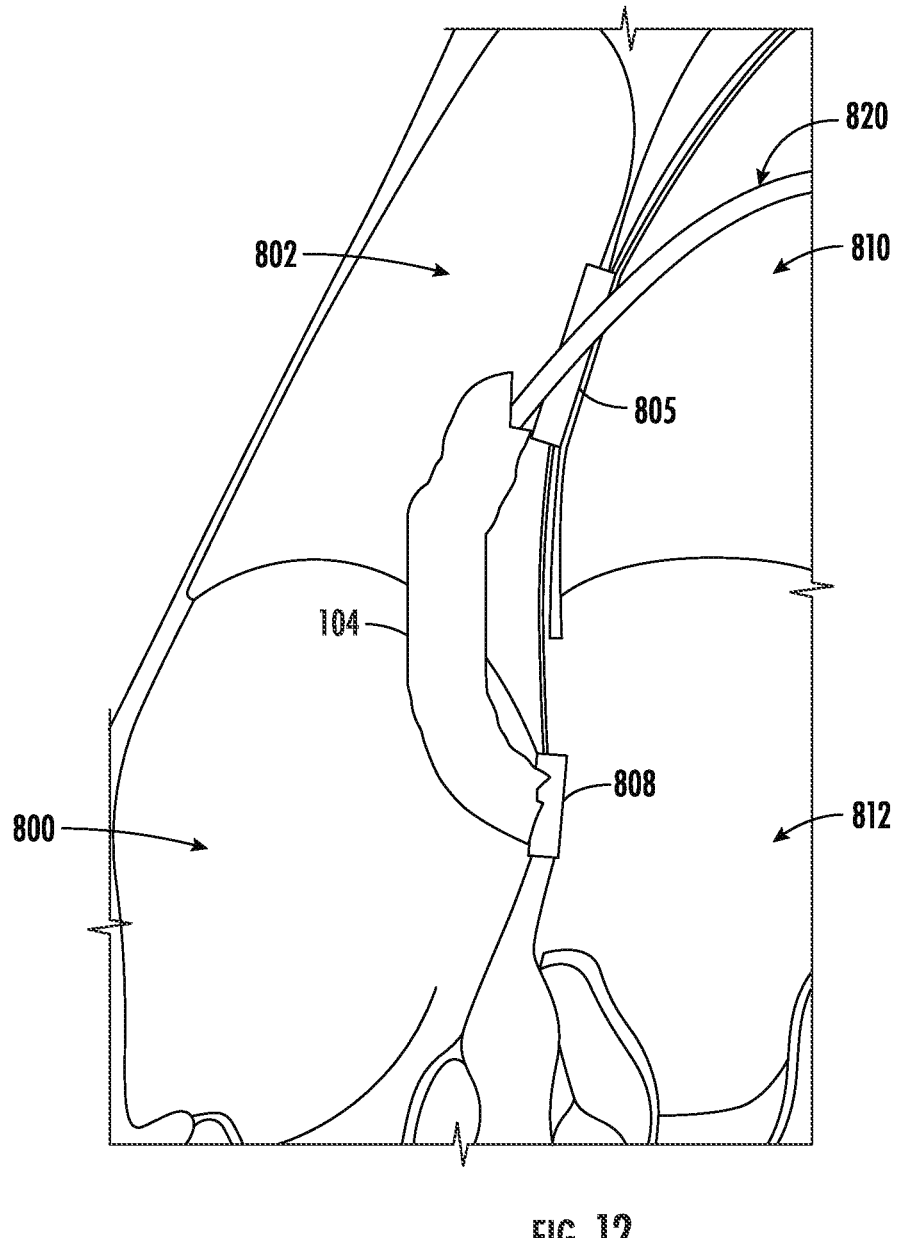
FIG. 12 illustrates the stent being attached to the second anchor.

Referring now to FIG. 12, a first end of stent 104 is attached to second anchor 808 through methods known in the art. Catheter 820 is steered through first anchor 805 into the aorta 801, while stent 104 is advanced. A second end of stent 104 may then be attached to first anchor 805 through methods known in the art.

Figure 13:
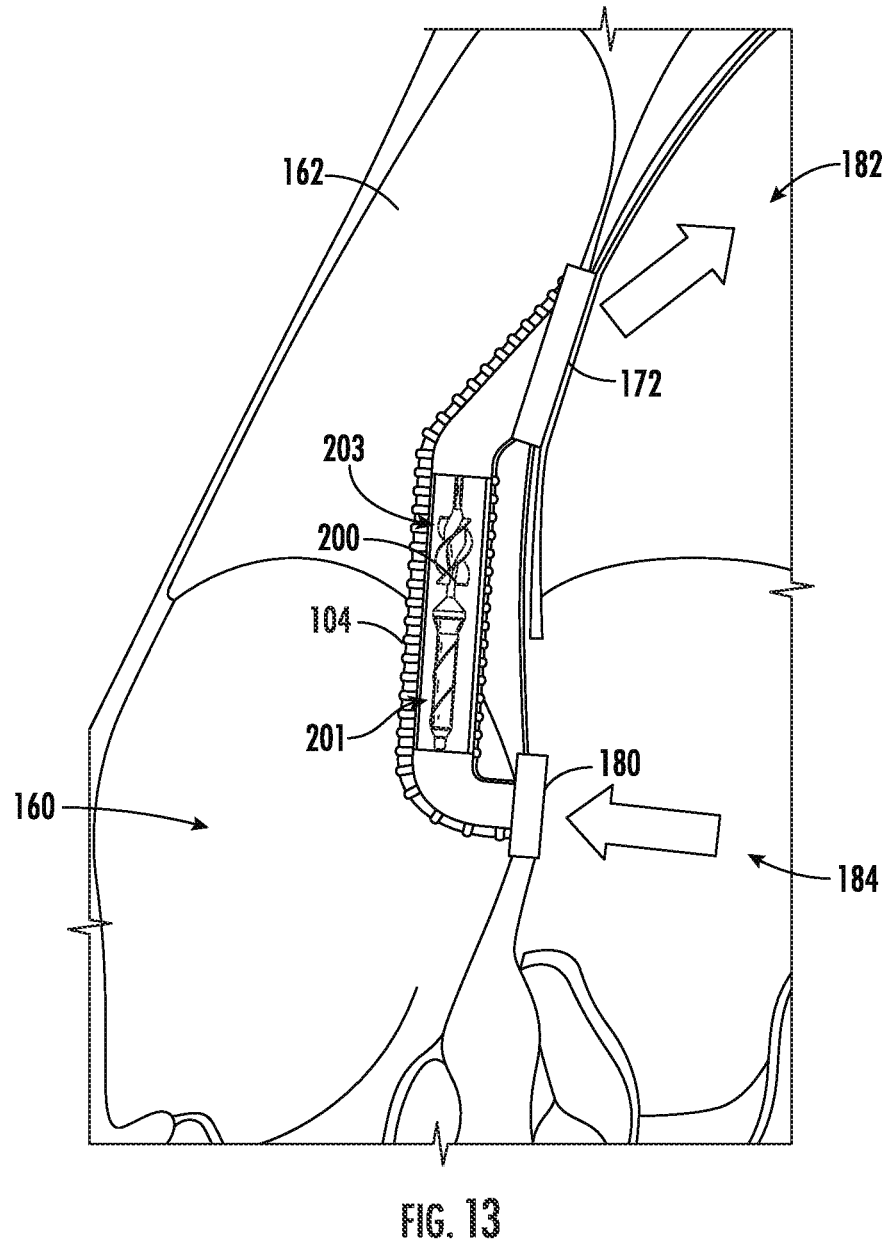
FIG. 13 illustrates the stent being attached to the first anchor by retracting the arterial catheter through the first anchor and into the aorta.

As shown in FIG. 13, once stent 104 is fully deployed, the distal end of catheter 820 is collapsed to its original size and retracted back through aorta 810 and the femoral artery to remove catheter 820 from the patient. Of course, it will be recognized by those of skill in the art that the systems and methods described herein may be used to implant other intracardiac devices. For example, they may be used to advance an aortic heart valve replacement through a vein, such as the femoral vein, to a target location between the left ventricle and the aorta. An arterial catheter, such as those described above, may be coupled to the artificial valve through the methods described above: either external to the body outside of the femoral vein access sheath, or internally within the body, such as within the inferior vena cava or the right atrium. The arterial catheter may then be used to withdraw the artificial valve into the patient's heart at the target location. This approach allows for use of a smaller bore arterial catheters than are conventionally used for minimally invasive implantation of artificial heart valves. The smaller bore arterial catheter minimizes stress on the femoral artery or aortic arch and reduces internal bleeding, bruising and other potential complications associated with a purely arterial approach.

Figure 14:
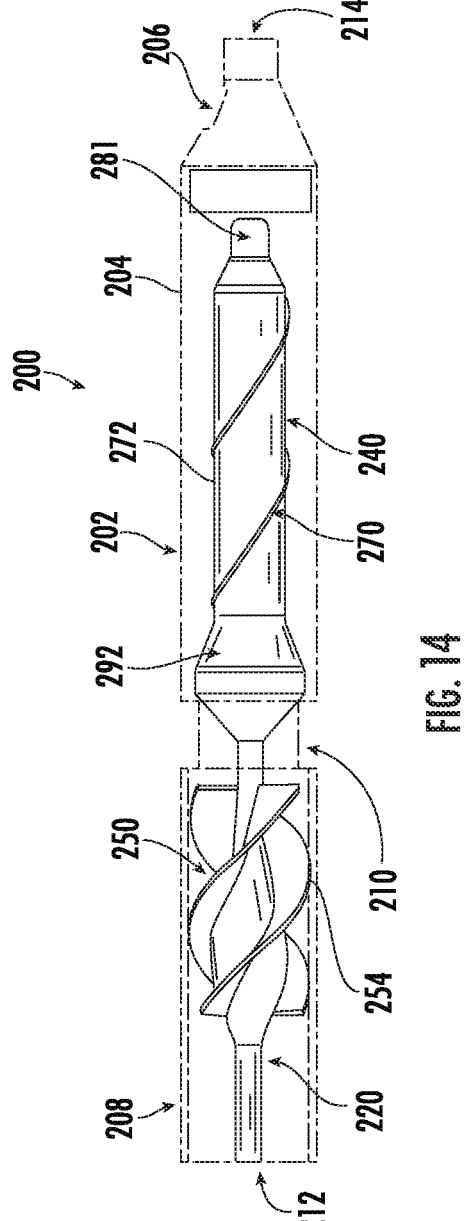
FIG. 14 is a side view of an axial flow pump.
Figure 15A:
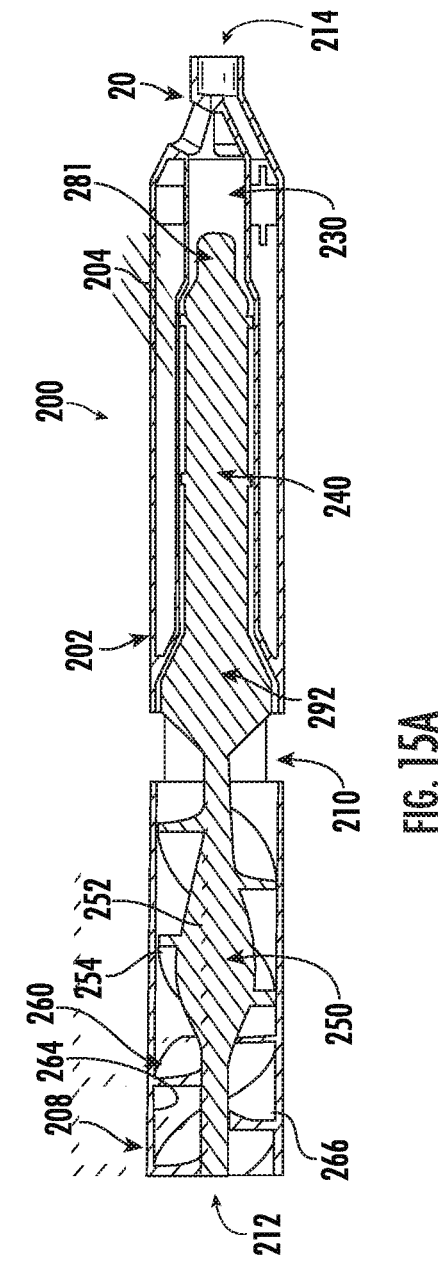
FIG. 15A is a cross-sectional view of the axial flow pump of FIG. 14.
Figure 15B:
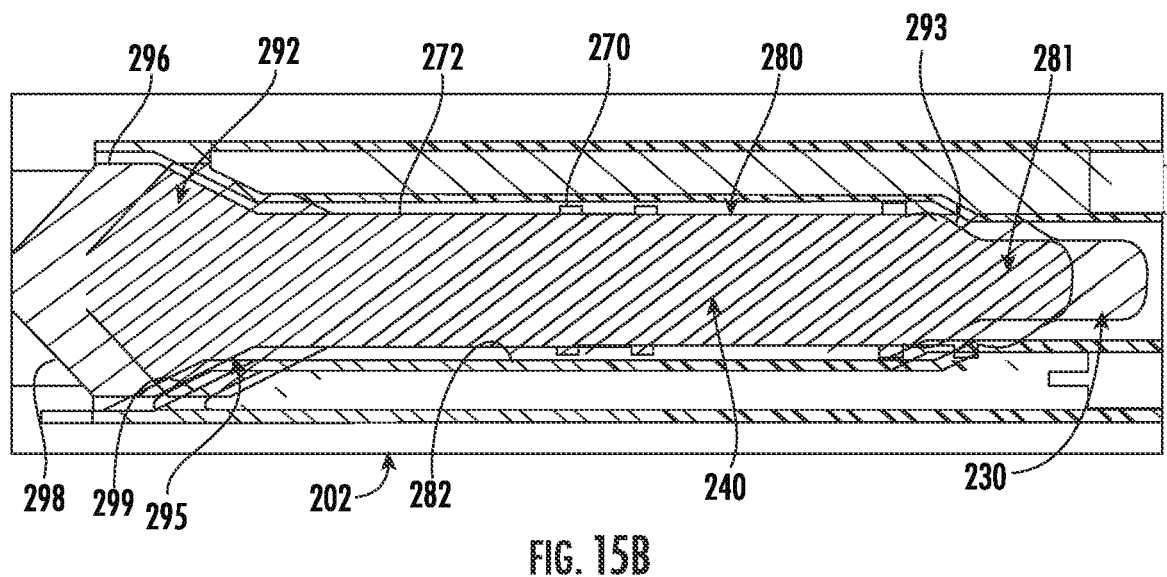
FIG. 15B is an enlarged cross-sectional view of a rotor of the axial flow pump.
Figure 15C:
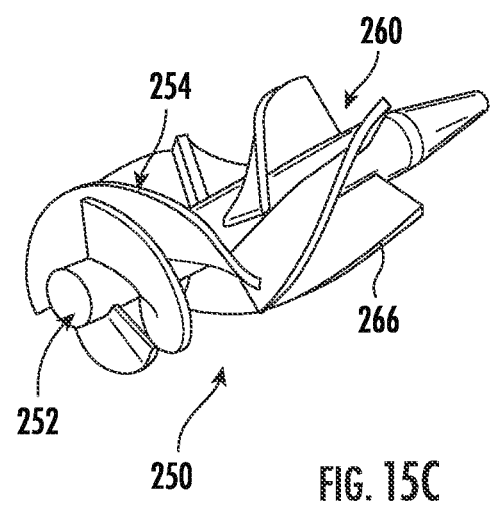
FIG. 15C is an enlarged perspective view of an impeller of the axial flow pump.
Figure 15D:
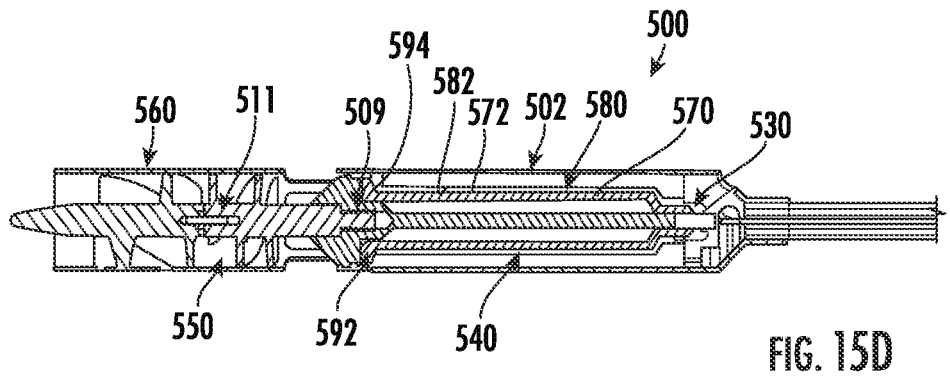
FIG. 15D is a side cross-sectional view of another embodiment of an axial flow pump.
Figure 5E:
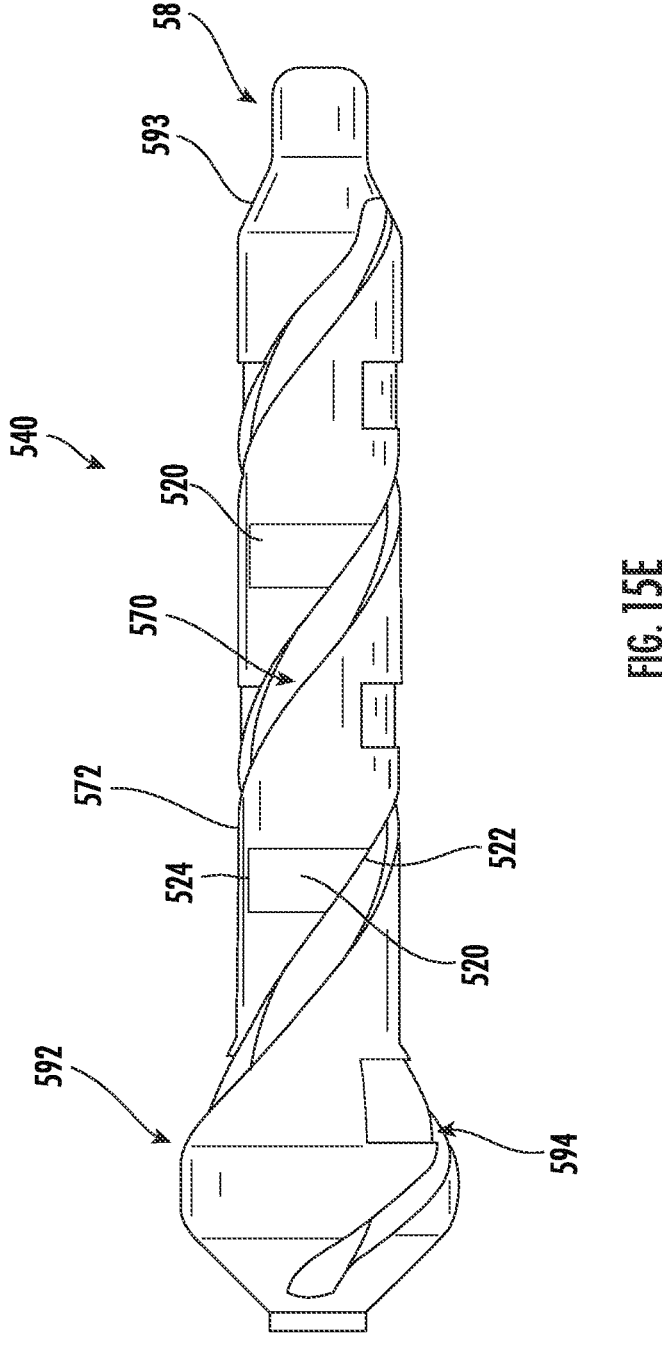
Figure 5E:
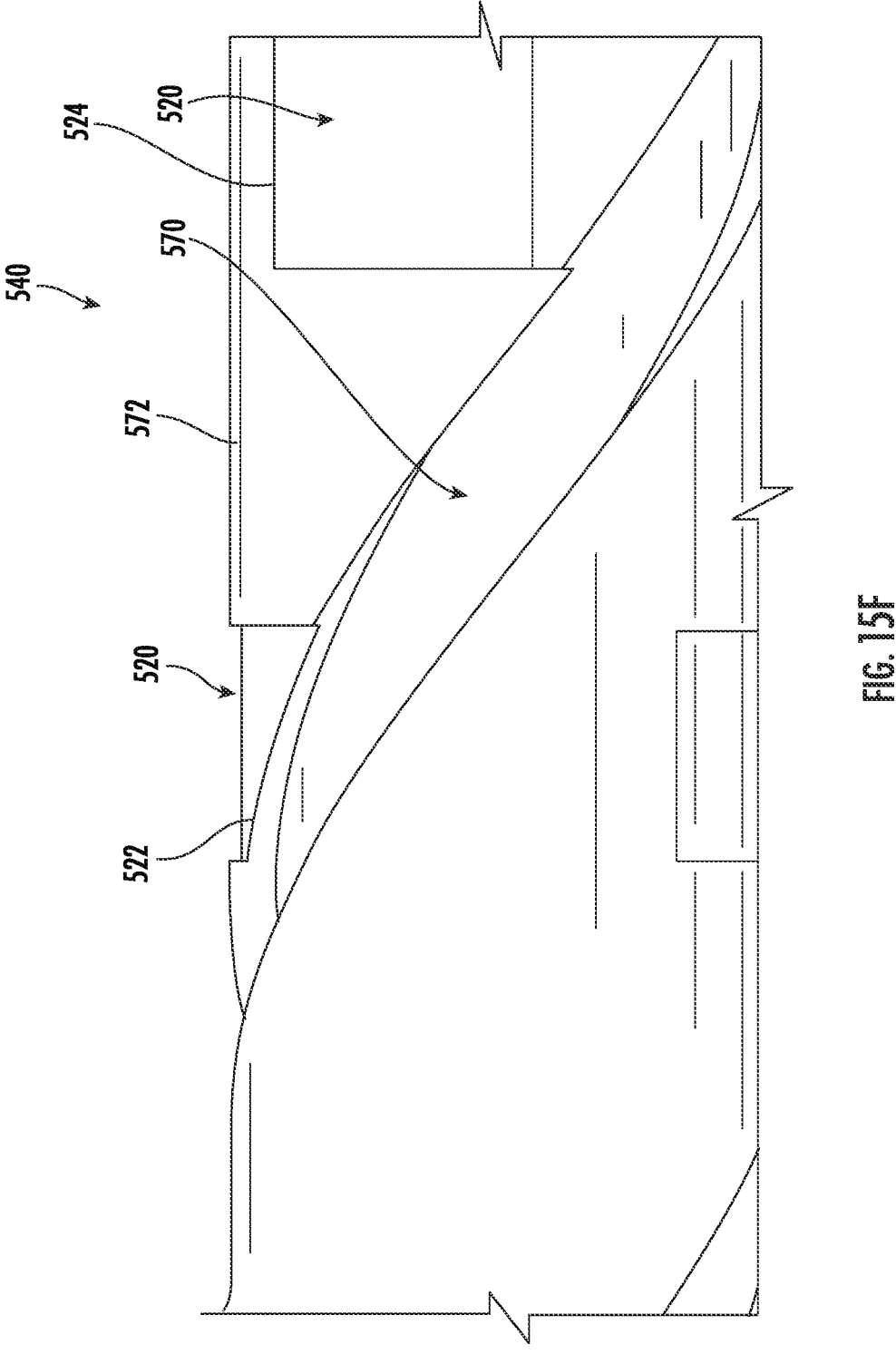
Figure 16:
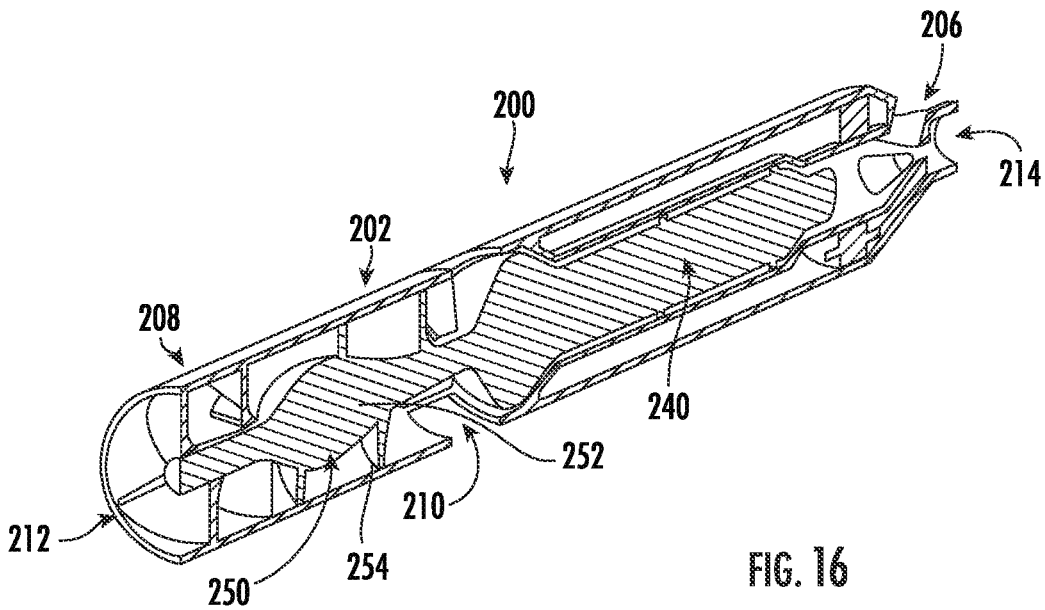
FIG. 16 is another cross-sectional view of the pump of FIG. 13.

Referring now to FIGS. 14-16, an exemplary embodiment of an intracardiac device 200 includes an outer casing 202 having a substantially cylindrical main body 204 with first and second ends 206, 208. Main body 204 preferably has a substantially uniform outer diameter to facilitate insertion of device 200 into an artery or specific delivery device. In some embodiments, however, device 200 may be inserted percutaneously, endoscopically or through an open incision in the patient. In these embodiments, device 200 may have other configurations.

Main body 204 includes a first inlet 210 located between first and second ends 206, 208, an outlet 212 at, or near, second end 208 and a second inlet 214 at, or near, first end 206. First inlet 210 and outlet 212 are fluidly coupled to each other to define a primary blood flow path 220 through an internal lumen in casing 202. Second inlet 214 is fluidly coupled to either or both of first inlet 210 and outlet 212 to define a secondary blood flow path 230 through an internal lumen of casing 202, as discussed in more detail below.

First inlet 210 preferably comprises a semi-circular opening in outer casing 202 that extends at least partially around the circumference of casing 202, preferably at least about 25% of the circumference, and more preferably at least about 50%. The exact size and shape of first inlet 210 is designed to provide sufficient flow from a heart chamber surrounding device 200 into primary blood flow path 220. Of course, other configurations are possible. For example, first inlet 212 may comprise one or more openings spaced from each other around the circumference of casing 202. Such openings may have any suitable cross-sectional shape, e.g., circular, square, diamond, rectangular, triangular or the like.

Device 200 further includes a motor stator (not shown) that is preferably integral with outer casing 202 and may include stator windings and a back iron. A tubular rotatable element 240 is positioned within casing 202 between first and second inlets 210, 214. Rotatable element 240 comprises a rotor portion of the motor and is configured to be rotated (i.e., driven) by the motor stator. In one embodiment, the motor stator includes one or more permanent magnets and rotor 240 includes one or more magnets such that rotor 240 may be rotated around its longitudinal axis by a suitable magnetic field, as is known in the art. Casing 204 may be formed from a magnetically permeable material selected to minimize power losses due to magnetic hysteresis. Electrical conductors (not shown) passing through casing 202 provide power and control signals to the electric motor.

Rotor 240 is coupled to an impeller 250 that comprises a hub 252 and one or more rotating blades 254 that project from hub 252 for drawing blood through inlet 210. The blades 254 may take any appropriate shape and be of any appropriate number. Blades 254 preferably define a clearance with the inner surface of casing of about 0.1 mm to about 0.8 mm, preferably about 0.2 mm to about 0.4 mm, more preferably about 0.3 mm. In one embodiment, blades 254 have a substantially helical shape such that the blades 254 spiral around hub 252 from the upstream end to the downstream end. Blades 254 may have the same, or a different, pitch. Each blade 254 may have a pitch that varies from hub 252 to the tip of the blade 254.

As shown in FIG. 15C, impeller 250 may include three blades 254 extending from hub 252 and spaced apart from each other. In certain embodiments, the pitch angle of each of the blades 254 changes in the longitudinal direction such that the angle between the blade surface and the blood flow increases in the downstream direction. Thus, the angle between the blade surface at the hub (where the blood first contacts the blade) is smaller and closer to parallel to the blood flow direction to reduce turbulence and minimize damage to the blood cells upon initial contact with blade 254. As the blood flows along the surface of the blade downstream, this angle increases to provide sufficient power to accelerate the blood flow and propel the blood radially relative to the housing.

Impeller further comprises a stator 260 that is configured to redirect the flow of the blood from the radial direction to the longitudinal direction towards outlet 212. Stator 260 includes one or more blade-shaped surfaces 266 that have pitch angles that decrease in the downstream direction. Similar to the impeller blades, surfaces 266 are designed to reduce the impact of the radial blood flow at the upstream end of the surface 266 and then to gradually redirect this blood flow in the longitudinal direction. This design reduces turbulence and minimizes damage to blood cells.

Rotor 240 preferably includes one or more ribs 270 extending from an outer surface 272 of rotor 240. Ribs 270 may comprise blades, vanes or other projections that extend around outer surface 272 and are configured to draw fluid into casing from second inlet 214 as rotor 240 rotates around its longitudinal axis. Ribs 270 preferably have a substantially helical shape with the same orientation as impeller blades 254 such that the flow of blood in secondary blood flow path 230 is in substantially the same direction as primary blood flow path 220.

Pump 600 provides an efficient design that may pump at least 5 Liters of blood per minute, preferably at least about 6 Liters/minute, at the physiological pressures typically existing within the heart chambers. Applicant has conducted tests of pump 600 to measure the pump's performance parameters. These tests have shown that pump 600 can pump over 5.5 Liters/minute of water at pressures around 59 mmHG at a rotational speed of about 25.4K RPM, and over 6 Liters/minute (about 6.4 Liters/minute) at pressures around 85 mmHG at a rotational speed of about 27.6K RPM.

In addition, pump 600 consumes less power than conventional axial flow pumps. Applicant has tested the power consumption of pump 600 in water and has determined that the pump consumes about 30 Watts at 25K RPM and about 32 Watts at 27.6 K RPM.

Of course, the pumps described herein are not limited to the specific impeller configuration described above and shown in the figures. For example, pump 200 can alternatively employ a fluid actuator that has a shaftless design for the actuation of fluids. The actuator comprises a housing having a plurality of blades. The housing has a hollow, substantially cylindrical shape having a long axis with open ends and an outer and an inner surface. Each of the blades is attached to the inner surface of the housing and extends from opposite ends of housing in a helical pattern. The blades are thereby configured to actuate a fluid by the rotation of the housing along its long axis. The rotation can be achieved by mechanical linkage with a motor, such as by a rim driven connection or an end-driven connection. The rotation can also be achieved by magnetic coupling with external electromagnets or a rotating magnet. The blades may have any suitable cross-section shape, including a substantially parallelogram-like cross-sectional, rectangular, with rounded edges, with sharp edges, and the like. A more complete description of a suitable fluid actuator with a shaftless design can be found in International Patent Application No. PCT/US2019/037047, the complete disclosure of which is incorporated herein by reference in its entirety for all purposes.

As shown in FIG. 15B, rotor 240 defines a clearance 280 between its outer surface 272 and the inner surface 282 of casing 202. This clearance 280 provides the space for secondary blood flow path 230. Blood flowing through secondary flow path 230 supports rotor 240 within casing 202, thereby providing a fluid bearing for rotor 240 (i.e., with no mechanical bearings). In addition, the blood continuously flushes clearance 280 to minimize the formation and/or growth of blood clots and/or to remove heat generated by the motor and rotor 240. The width of clearance preferably remains substantially constant and is in the range of about 0.1 mm to about 0.8 mm, preferably about 0.2 mm to 0.4 mm, and more preferably about 0.3 mm. This width is preferably substantially the same as the clearance between impeller blades 254 and casing 202.

The operation of rotor 240 and impeller 250 creates a force that draws these element forward (i.e., in the direction opposite the blood flow or left to right in FIG. 14). Since device 200 does not contain any mechanical bearings to arrest this movement and prevent the rotor 240 from being drawn so far forward that it contacts the inner surface of casing 202, device 200 includes one or more fluid pressure elements that provides resistance to the flow of blood along secondary flow path 230. This resistance at least partially offsets these axial forces and serves to arrest the forward translation of rotor 240 and impeller 250 within casing 202.

In one embodiment, the fluid pressure elements comprises an enlarged bulb 292 coupled to, or integral with, rotor 240 and having an outer diameter larger than the outer diameter of rotor 240. Bulb 292 includes an outer surface 296, a first inclined surface 294 adjacent the outer surface of rotor 240 that is transverse to the flow of blood in secondary flow path 230 and a second inclined surface 298 adjacent inlet 210. Outer casing 202 includes a substantially cylindrical inner surface 282 that surrounds rotor 240 to provide clearance 280. This inner surface 282 includes an inclined portion 299 that extends alongside inclined surface 294 of bulb 292 to form a clearance 295 therebetween.

Clearance 295 has a smaller cross-sectional area than clearance 280. Thus, fluid flowing clearance 295 is compressed creating a higher fluid pressure within this area. This higher fluid pressure applies a force against inclined surface 294 of bulb 292. The force applied against bulb 292 is in the opposite direction of forces applied by impeller 250 and rotor 240 and therefore at least partially resists these axial forces to maintain the axial position of impeller 250 and rotor 240 relative to housing.

The angle of inclined surface 298 is critical. The larger the angle between inclined surface 298 and the longitudinal axis or the direction of clearance 280, the greater the force that is applied against inclined surface 298 as blood flows therethrough (the relative cross-sectional area of clearance 295 will almost impact these forces). On the other hand, a large change in direction of blood flow through clearance 295 could cause damage to the blood cells. Therefore, Applicant has discovered that the optimal angle for inclined surface is about 5 degrees to about 45 degrees, preferably between about 10 degrees and about 30 degrees.

Of course, it will be recognized that other configurations for providing an offsetting axial force may be included in device 200. For example, the thickness of clearance 280 may be reduced in others places along secondary flow path 230 to create high pressure regions. Alternatively, secondary flow path 230 may include other surfaces or elements, such as projections extending into path 230 from either rotor 240 or casing 204, or a roughened surface on the rotor or casing. In some cases, secondary flow path 230 may be designed to provide a non-linear path through casing 204 to provide additional force vectors in the opposite direction of the flow provided by impeller 250.

Device 600 may further include an additional magnetic bearing to maintain the axial positions of rotor 240 and impeller 250 in the event that the secondary flow path does not sufficiently resist these forces. In one embodiment, for example, the axial magnetic bearing may comprise a permanent axial housing magnet (not shown) positioning within casing 202 that cooperates with a permanent axial rotor magnet (not shown) positioned in the rotor 240 and/or the impeller 250. In another embodiment, the axial magnetic bearing may include an active magnetic bearing that operates alone or in conjunction with a passive magnetic bearing. In this embodiment, the axial magnetic bearing may comprise, for example, a cylindrical passive magnet designed to counteract the axial forces encountered when rotor 240 is up to speed, surrounded by an active magnet, designed to compensate for additional axial loads, such as those present during pre-load or after-load of impeller 250. In yet another embodiment, permanent magnets may be radially distributed around impeller 250 and/or rotor 240. The attractive force of the magnetic coupling provides axial restraint to impeller 250.

Device may also include a radial magnetic bearing for stabilizing radial forces against rotor 240 and impeller 250 to minimize contact between these components and casing 202. For example, permanent radial bearing magnets (not shown) may be disposed within casing 202 and designed to cooperate with rotor bearing magnets in rotor 240 and/or impeller 250. The radial bearing magnets allow the rotor 240 and impeller 250 to rotate relative to casing 202 without significant radial contact. In addition, they assist the fluid bearing described above to maintain the annular clearance 280 between rotor 240 and casing 202, as well as the clearance between impeller blades 254 and casing 202.

Rotor 240 may further include an upstream magnetic bearing 281 positioned at the end of rotor 240 opposite impeller 250 that includes one or more magnets therein (not shown) to form the axial and/or radial magnetic bearings for device 200.

Alternatively, magnetic bearing 281 may function similar to enlarged portion 292 of rotor 240 to provide a relatively high fluid pressure region that creates stabilizing axial forces. For example, bearing 281 is designed with a smaller outer diameter than the remainder of rotor 240 (see FIG. 15B). In this configuration, bearing 281 and rotor 240 define an inclined surface 293 therebetween. Inclined surface 293 may be configured to create a clearance between bearing 281 and the inner surface of housing 202 that has a smaller cross-sectional area than the cross-sectional area of clearance 280. Similar to the above description of enlarged portion 292, this increases the fluid pressure within this clearance and applies a force against inclined surface 293.

Referring now to FIGS. 15D-15F, another embodiment of an axial flow pump 500 will now be described. As in the previous embodiment, pump 500 includes an outer housing or casing 502 and a rotor 540 coupled to an impeller 550 and a stator or diffuser 560. Rotor 540 and impeller 550 may be coupled together by any suitable means, such as a threaded screw type connection 509 that allows rotor 540 to rotate impeller 550. Impeller 550 and stator 560 are rotatably coupled to each other with a rotational linkage 511 such that stator 560 remains stationary within housing 502 as impeller 550 rotates.

In this embodiment, rotor 540 includes one or more grooves, channels or the like 570 extending around an outer surface 572 of rotor 540. Groove 570 preferably extend around outer surface 572 in a spiral or helical direction similar to ribs 270 and function in the same manner to draw blood into a secondary flow path 530 that passes through a clearance 580 between rotor 540 and an inner surface 582 of housing 202.

Pump 500 comprises an enlarged bulb 592 coupled to, or integral with, rotor 540 and having an outer diameter larger than the outer diameter of rotor 540. Bulb 592 includes a surface 594 adjacent the outer surface of rotor 540 that is transverse to the flow of blood in secondary flow path 530. As in previous embodiments, this compresses the fluid creating a higher fluid pressure within this area. This higher fluid pressure applies a force against inclined surface 594 of bulb 592. The force applied against bulb 592 is in the opposite direction of forces applied by impeller 550 and rotor 540 and therefore at least partially resists these axial forces to maintain the axial position of impeller 550 and rotor 540 relative to housing.

Referring now to FIGS. 15E and 15F, rotor 540 further comprises a plurality of variable pressure surfaces 520 that are spaced from each other both longitudinally and circumferentially with respect to rotor 540. Variable pressure surfaces 520 each have a first end 522 adjacent groove 570 and a second end 524 circumferentially spaced away from groove 570 such that the surfaces 520 extend from groove 570 to a portion of outer surface 572 between adjacent spirals of the groove 570.

As shown more clearly in FIG. 15F, variable pressure surfaces 520 are at least partially recessed from the outer surface 572 of rotor 550. Specifically, surfaces 520 are angled in the circumferential direction such that second end 524 is substantially parallel with the outer surface of 572 of rotor and first end 522 extends inwardly at an angle relative to outer surface 572. Thus, first end 522 is recessed from outer surface 572 and gradually angles upward relative to surface 572 until it joins with the outer surface and is no longer recessed. This creates a greater cross-sectional area between the inner surface 582 of housing 502 at first end 522 of pressure surface 520 than the cross-sectional area between inner surface 582 of housing and second end 524 of housing. Also, the cross-sectional area between first end 522 and inner surface 582 is greater than the cross-sectional area of clearance 580 (see FIG. 15D).

In the event that any portion of rotor 540 moves closer to inner surface 582 of housing 502 (i.e., such that the clearance 580 becomes smaller at that location), the variable pressure surfaces 520 compress the blood flowing past them at the circumferential location that is closest to inner surface 582 of housing 502 to generate a force opposing this motion. This radial force resists the radial force or motion that is moving the rotor towards the housing and would otherwise destabilize the radial position of rotor 540 within housing 520.

Figure 17:
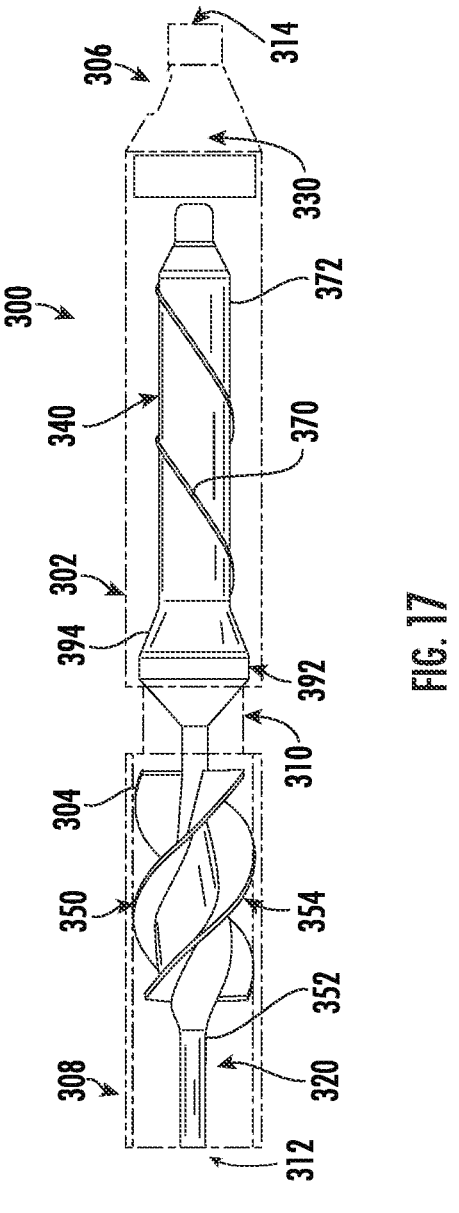
FIG. 17 is a side view of another embodiment of an axial flow pump.

Referring now to FIG. 17, an alternative embodiment of an intracardiac device 300 includes an outer casing 302 having a substantially cylindrical main body 304 with first and second ends 306, 308. Main body 304 may have a substantially uniform outer diameter to facilitate insertion of device 300 into an artery or specific delivery device. Main body 304 includes an inlet 310 located between first and second ends 306, 308, a first outlet 312 at, or near, second end 308 and a second outlet 314 at, or near, first end 306. Inlet 310 and first outlet 312 are fluidly coupled to each other to define a primary blood flow path 320 through an internal lumen in casing 302. Inlet 310 is also fluidly coupled to second outlet 314 to define a secondary blood flow path 330 through an internal lumen of casing 302.

Device 300 further includes a motor stator (not shown) that is preferably integral with outer casing 302 and may include stator windings and a back iron. A tubular rotatable element 340 is positioned within casing 302 between inlet 310 and second outlet 314. Rotatable element or rotor 340 is configured to be rotated (i.e., driven) by the motor stator. In one embodiment, the motor stator includes one or more permanent magnets and rotatable element 340 includes one or more magnets such that rotatable element 340 may be rotated by a suitable magnetic field, as is known in the art.

Rotor 340 is coupled to an impeller 350 that comprises a hub 352 and one or more rotating blades 354 for drawing blood through inlet 310. Device 300 may further include a diffuser or stator (not shown) that is configured to redirect blood flow from the radial direction to the longitudinal direction and to reduce turbulence of the blood flow passing through blades 354 and into outlet 312. In one embodiment, blades 354 have a substantially helical shape such that the blades 234 spiral around hub 352 from the upstream end to the downstream end.

Rotor 340 preferably includes one or more ribs 370 (or channels) extending from an outer surface 372 thereof. Ribs 370 may comprise blades, vanes, fins or other projections that extend around outer surface 372 and are configured to draw fluid into casing from inlet 310 as element 340 rotates around its longitudinal axis. Ribs 370 preferably have a substantially helical shape with generally the opposite orientation as impeller blades 354 such that the flow of blood in secondary blood flow path 330 is in substantially the opposite direction as primary blood flow path 320. Similar to the device shown in FIGS. 14-16, rotor 240 defines a clearance (not shown) between its outer surface and the inner surface of casing 202.

The blood flowing through secondary flow path 330 creates a force against device 300 that is in the opposite direction as the force created by the blood flowing through impeller 354 in the primary blood path 320. The mass flow rate of the blood in secondary flow path 330 is significantly less than the mass flow rate of the blood in primary flow path 320 in order to ensure that the majority of the power applied to pump 300 is consumed with the primary goal of propelling blood through the primary flow path and into the aorta to support function of the left ventricle. In certain embodiments, mass flow rate of the blood in secondary flow path is about 1% to about 20%, preferably about 5% to about 10% of the mass flow rate of the blood in primary flow path 320.

Since the mass flow rate of the secondary flow path is less than the primary flow path, additional forces must be applied to maintain axial stability of the rotor and impeller. To that end, device 300 includes one or more fluid pressure elements that provides resistance to the flow of blood along secondary flow path 330. This resistance at least partially offsets these axial forces and serves to arrest the forward translation of rotor 340 and impeller 350 within casing 302.

In one embodiment, the fluid pressure elements comprises an enlarged bulb 392 coupled to, or integral with, rotor 340 and having an outer diameter larger than the outer diameter of rotor 340. Bulb 392 includes an outer surface 396, a first inclined surface 394 adjacent the outer surface of rotor 340 that is transverse to the flow of blood in secondary flow path 330 and a second inclined surface 398 adjacent inlet 310. Outer casing 302 includes a substantially cylindrical inner surface 382 that surrounds rotor 340 to provide clearance 380. This inner surface 382 includes an inclined portion 399 that extends alongside inclined surface 394 of bulb 392 to form a clearance 395 therebetween.

Clearance 395 has a smaller cross-sectional area than clearance 380. Thus, fluid flowing through clearance 395 is compressed creating a higher fluid pressure within this area. This higher fluid pressure applies a force against inclined surface 394 of bulb 392. The force applied against bulb 392 is in the opposite direction of forces applied by impeller 350 and rotor 340 and therefore at least partially resists these axial forces to maintain the axial position of impeller 350 and rotor 340 relative to housing.

Figure 18:
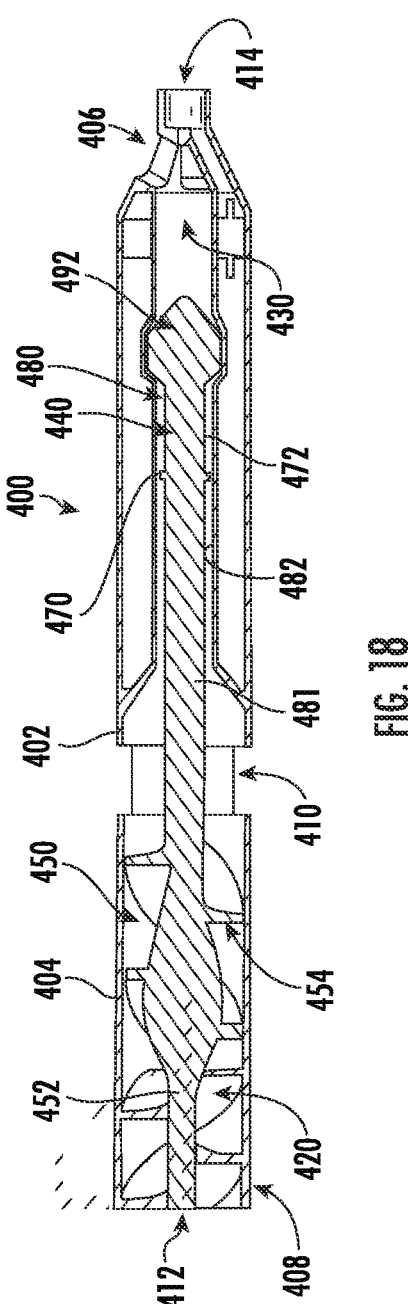
FIG. 18 is a cross-sectional view of another embodiment of an axial flow pump.

Referring now to FIG. 18, another embodiment of an intracardiac device 400 comprises an outer casing 402 having a substantially cylindrical main body 404 with first and second ends 406, 408. Main body 404 includes a first inlet 410 located between first and second ends 406, 408, an outlet 412 at, or near, second end 408 and a second inlet (or outlet) 414 at, or near, first end 406. First inlet 410 and outlet 412 are fluidly coupled to each other to define a primary blood flow path 420 through an internal lumen in casing 402. Second inlet (or outlet) 414 is fluidly coupled to either or both of first inlet 410 and outlet 412 to define a secondary blood flow path 430 through an internal lumen of casing 402.

Similar to previous embodiments, device 400 also includes a motor stator (not shown) and a rotor 440 positioned within casing 402 between first and second inlets 410, 414. Rotor 440 is coupled to an impeller 450 that comprises a hub 452 and one or more rotating blades 454 for drawing blood through inlet 410. Rotor 440 preferably includes one or more ribs 470 extending from an outer surface 472 of rotatable element 440. Ribs 470 may comprise blades or other projections that extend around outer surface 472 and are configured to draw fluid into casing from inlet 410 as rotor 440 rotates around its longitudinal axis. Alternatively, ribs 470 may be oriented to draw blood from inlet 414. Ribs 470 preferably have a substantially helical shape and may be oriented in the same or the opposite direction as impeller blades 354, as described in the embodiments of FIGS. 14-17.

Rotor 440 defines a clearance 480 between its outer surface 472 and the inner surface 482 of casing 402. This clearance 480 provides the space for secondary blood flow path 430. Blood flowing through secondary flow path 430 ensures that rotatable element 440 does not contact casing 402.

In this embodiment, the fluid pressure element comprises an enlarged bulb 492 coupled to rotor 440 having an outer diameter larger than the outer diameter of rotatable element 440. Bulb 492 is located near second inlet 414 on the opposite side of rotor 440 from impeller 454. An axial magnetic bearing 481 is located on the side of rotatable element 440 adjacent to or near impeller 454. Locating axial magnetic bearing 481 closer to impeller reduces the distance of the magnetic field, thereby making it more efficient and requiring less power consumption to provide axial stability to the device.

Figure 19:
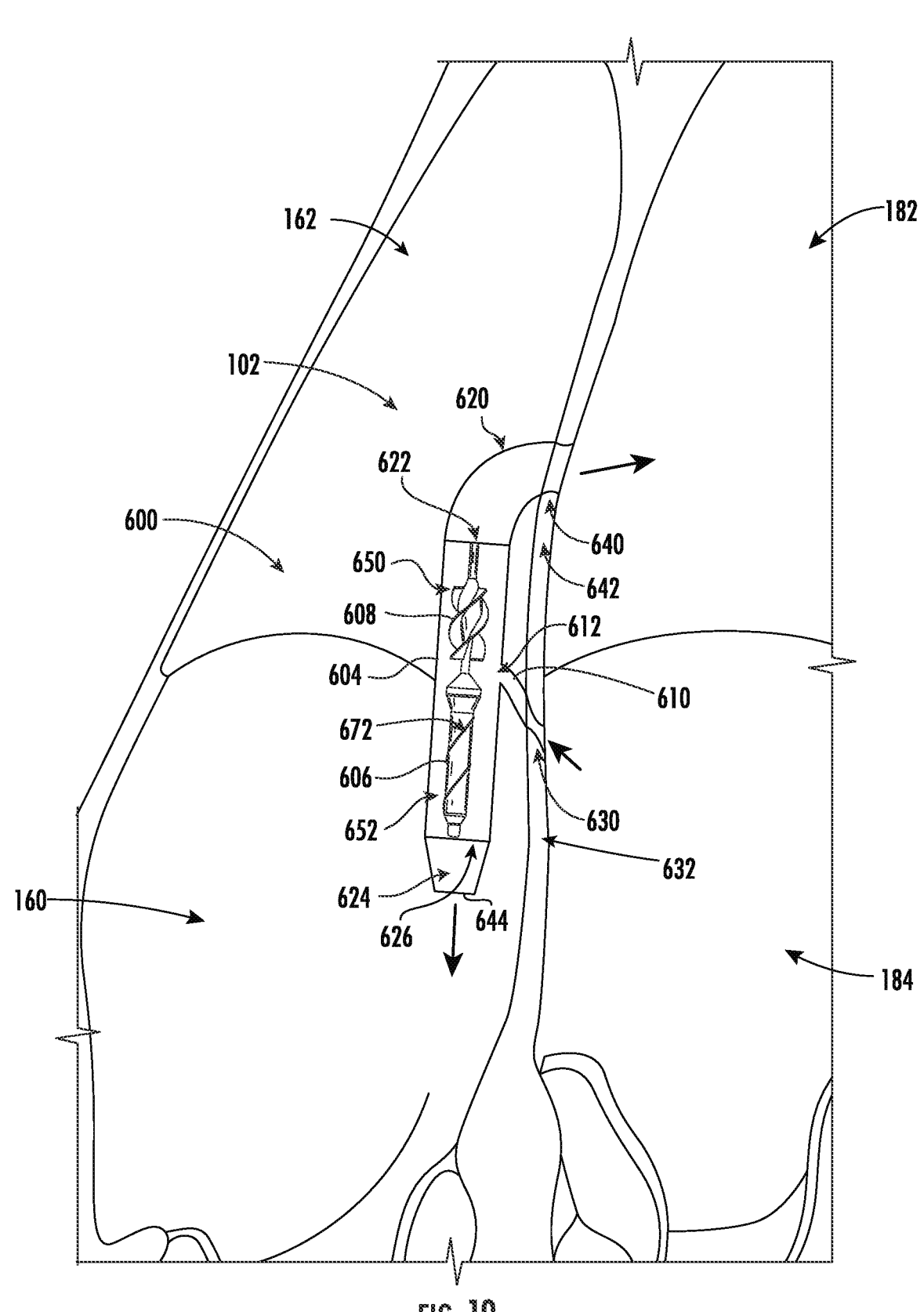
FIG. 19 is a schematic view of an axial flow pump in a right atrium of a patient's heart, illustrating a secondary flow path from the left atrium to the right atrium.

Referring now to FIG. 19, a system and method for supporting cardiac function with an implantable intracardiac device 600 will now be described. Device 600 is configured for implantation into the right atrium 160 and/or the SVC 162 of the patient. As discussed previously, device 600 includes an outer casing 604 enclosing a rotor 606 coupled to a motor stator (not shown) and an impeller 608. Device 600 further includes a first tube 610 attached to an inlet 612 within device 600 between rotor 606 and impeller 608, a second tube 620 attached to a first outlet 622 of device 600 and a third tube 624 attached to a second outlet 626 of device 600. Tubes 610, 620, 624 may be formed integrally with device 600, or they may be removably coupled to device 600 through any coupling device known to the art. One or all of the tubes may include a valve for opening and closing the fluid connection between the tube and device 600. The valve(s) may include sensors and may be controlled externally through the wireless power system described above.

In certain embodiments, device 600 includes one or more sensors (not shown) configured for detecting a physiological parameter of the right atrium, such as pressure, temperature or the like. The sensors are coupled to an internal or external controller (such as those described herein) and may be configured to transmit data related to the physiological parameter to the controller to allow for monitoring of these physiological parameters during operation of the device 600.

Device 600 further includes a first anchor 630 coupled to an inlet of first tube 610 and configured for anchoring tube 610 to a septal wall 632 between the right atrium and a left atrium 184 of the patient. Anchor 630 is configured to create a fluid passage through wall 632 such that blood may flow from left atrium 184 and into tube 610. A valve may be included within anchor 630 in addition to, or alternatively to, the valve coupling tube 610 to device 600. First anchor 630 may include one or more sensors (not shown) configured for detecting one or more physiological parameters of the left atrium and/or the right atrium. The sensors are coupled to the internal or external controller and may be configured to transmit data related to the physiological parameter to the controller to allow for monitoring of these physiological parameters during operation of the device 600.

Device 600 further includes a second anchor 640 coupled to an outlet of second tube 620 and configured for anchoring second tube 620 to a wall 642 between the SVC 162 and an aorta 182 of the patient. The valve may be included within anchor 640 in addition to, or alternatively to, the valve coupling tube 620 to device 600. Second anchor 640 may include one or more sensors (not shown) configured for detecting one or more physiological parameters of the SVC and/or the aorta. The sensors are coupled to the internal or external controller and may be configured to transmit data related to the physiological parameter to the controller to allow for monitoring of these physiological parameters during operation of the device 600.

Third tube 624 includes an outlet 644 that may be fluidly coupled with right atrium 602. Alternatively, outlet 626 of device 600 may simply have an open end coupled to right atrium 160 (i.e., without a tube extending therefrom).

Device 600 may further include one or more additional anchors (not shown) coupled to casing 602 and configured to secure device 600 to one or more of the inner walls of right atrium 160 and/or SVC 162.

Device 600 has a similar blood flow path as device 300 described above and shown in FIG. 17. Namely, impeller 608 creates a primary blood flow path 650 from left atrium 184, through first tube 610 and inlet 612 into device 600. The blood flows past impeller 608 through outlet 622 to second tube 620 and through anchor 640 into the aorta 182 of the patient. This primary blood flow path assists the heart by pumping blood from the left atrium directly into the aorta. The primary blood flow path bypasses the left ventricle and reduces the pre-load on the left ventricle, thereby supporting heart function.

In addition, device 600 creates a secondary blood flow path 652 from inlet 612 past rotor 606 and through second outlet 626 into tube 624, where it is propelled into right atrium 160. As discussed above, the secondary blood flow path 652 supports rotor 606 within casing (with no mechanical bearings), cleans blood and other debris form the clearance between rotor 606 and the casing 604 and at least partially offsets axial forces applied to device 600 by impeller 608.

The blood that exits tube 624 and into right atrium 160 will be oxygenated since it originated from the left atrium. Accordingly, it is important to minimize the mass flow rate of the blood passing through secondary flow path 652 to minimize the amount of oxygenated blood within the right atrium that will eventually travel through the patient's lungs. To that end, secondary flow path 652 is configured to allow a mass flow rate of about 5% to about 10% of the mass flow rate of primary flow path 650.

Applicant has discovered that it is advantageous to drive the blood from secondary flow path 652 into right atrium 602, rather than into aorta 642 or back into left atrium 634. This is because this blood is flushing out any blood or other debris within the clearance between rotor 606 and casing 602. If this blood or debris includes any blood clots, these clots will not pass into the aorta and the arteries supplying blood to the brain, which avoids the potential for a thrombotic stroke.

Figure 20:
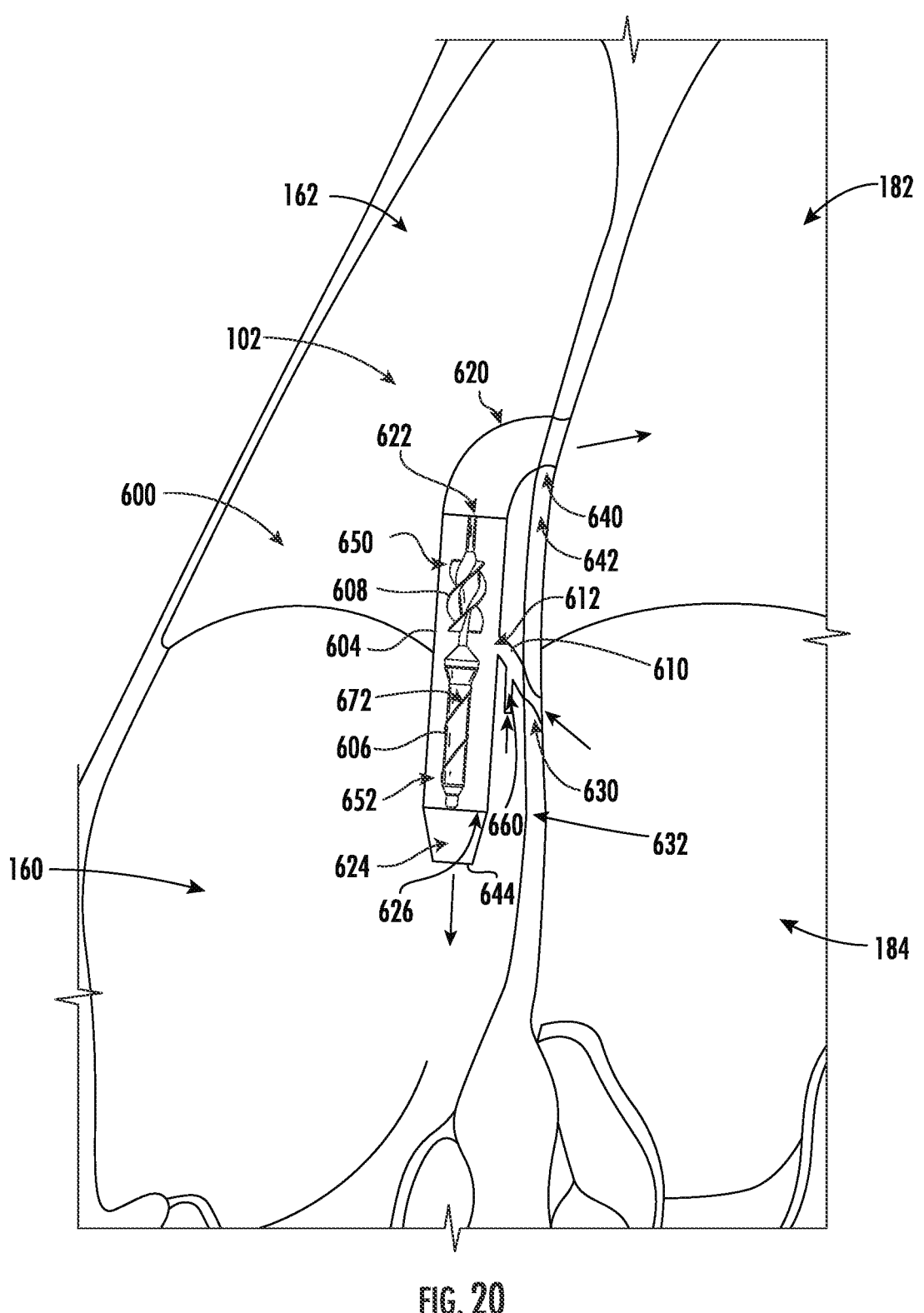
FIG. 20 is a schematic view of an axial flow pump in the right atrium of a patient's heart, illustrating a secondary flow path from the right atrium, through the pump and back into the right atrium.

Referring now to FIG. 20, another embodiment of an implantable intracardiac device 600 for supporting cardiac function will now be described. Device 600 is configured for implantation into the right atrium 160 and/or the SVC 162 of the patient. As discussed previously, device 600 includes an outer casing 604 enclosing a rotor 606 coupled to a motor stator (not shown) and an impeller 608. Device 600 further includes a first tube 610 attached to an inlet 612 within device 600 between rotatable element 606 and impeller 608, a second tube 620 attached to a first outlet 622 of device 600 and a third tube 624 attached to a second outlet 626 of device 600.

Device 600 further includes a first anchor 630 coupled to an inlet of first tube 610 and configured for anchoring tube 610 to a septal wall 632 between the right atrium 602 and a left atrium 634 of the patient. Anchor 630 is further configured to create a fluid passage through wall 632 such that blood may flow from left atrium 634 and into tube 610.

Device 600 further includes a second anchor 640 coupled an outlet of second tube 620 and configured for anchoring second tube 620 to a wall between the SVC 162 and the aorta 182 of the patient. Third tube 624 includes an outlet 644 that may be fluidly coupled with right atrium 602.

In this embodiment, device 600 further includes a fourth tube 660 fluidly coupled to first tube 620 between anchor 630 and inlet 612 of device 600. The fourth tube 660 may be a separate tube that is connected to tube 610 through a suitable fluid connection, e.g., luer lock or the like. Alternatively, tubes 610 and 660 may be a single Y-shaped tube having two inlets and one outlet.

In this embodiment, impeller 608 creates a primary blood flow path 650 from left atrium 634, through first tube 610 and inlet 612 into device 600. The blood flows past impeller 608 through outlet 622 to second tube 620 and through anchor 640 into the aorta of the patient. This primary blood flow path assists the heart by pumping blood from the left atrium directly into the aorta. The primary blood flow path bypasses the left ventricle and reduces the pre-load on the left ventricle, thereby supporting heart function.

In addition, device 600 creates a secondary blood flow path 652 from inlet 612 past rotor 606 and through second outlet 626 into tube 624, where it is propelled into the right atrium. As discussed above, the secondary blood flow path 652 supports rotor 606 within casing (with no mechanical bearings), cleans blood and other debris form the clearance between rotor 606 and the casing 604 and at least partially offsets axial forces applied to device 600 by impeller 608.

In this embodiment, inlet 612 may include separate passages coupling tube 610 with primary flow path 650 and tube 660 with secondary flow path 652. The separate passages may be included within 610 downstream of the Y-connection. Alternatively, tube 660 may enter device 660 in a separate inlet, e.g., between inlet 612 and rotor 606. This design ensures that the blood flowing from right atrium 602 passes only through secondary flow path 652. Likewise, the blood flowing from left atrium 634 only flows through primary flow path 650. This ensures that only oxygenated blood from the left atrium passes into the aorta and downstream through the arterial system. In addition, the blood from the right atrium is recirculated back into the right atrium, ensuring that the deoxygenated blood remains in the right side of the heart and any blood clots that are flushed from the pump remain on the right side of the heart.

Figure 21:
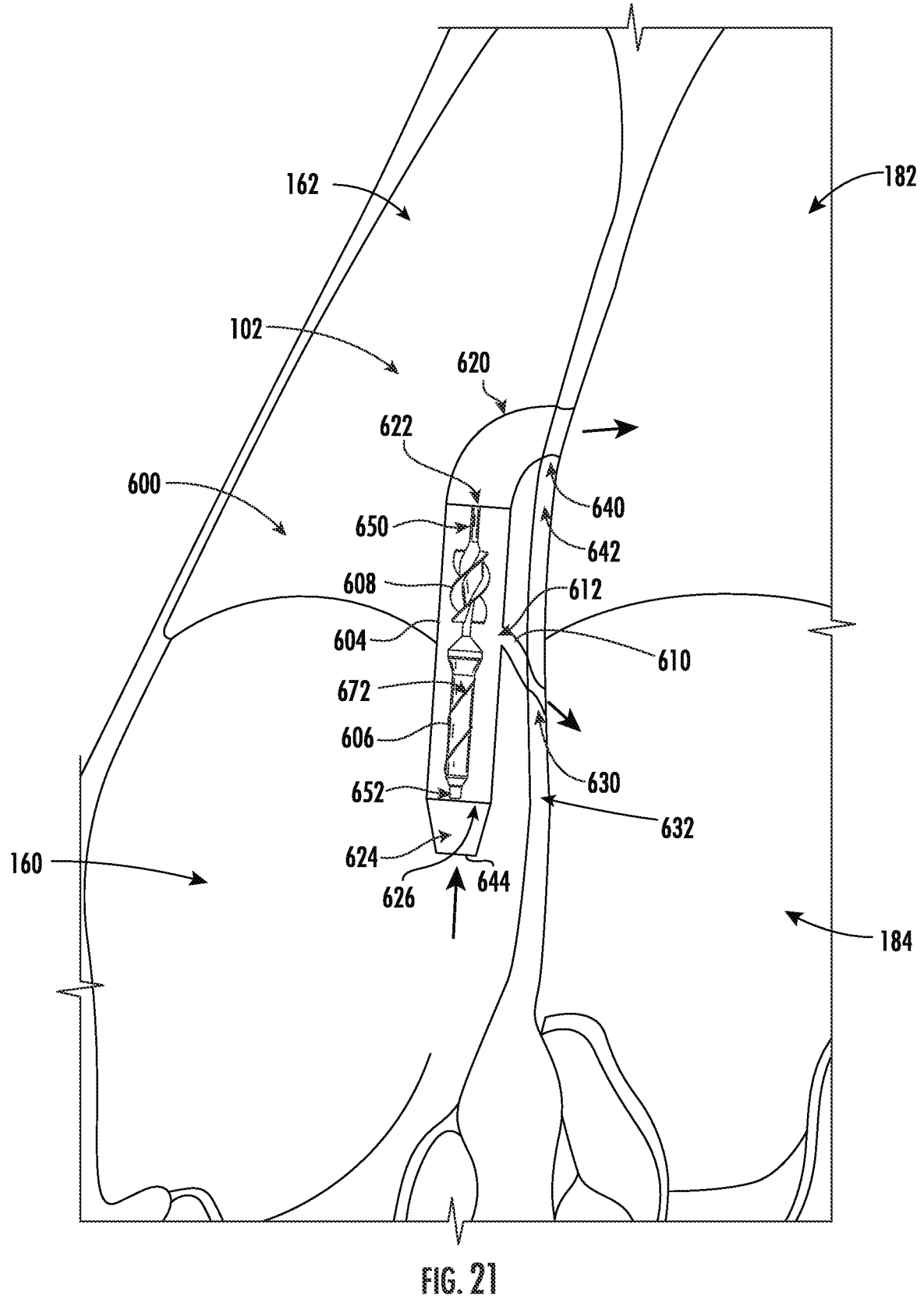
FIG. 21 is a schematic view of an axial flow pump in the right atrium of a patient's heart, illustrating a secondary flow path from the left atrium to the aorta.

Referring now to FIG. 21, device 600 has a similar construction as in FIG. 20 above except that the ribs 672 on rotor 606 form a reverse orientation so that the secondary blood flow path 652 is in substantially the same direction as the primary blood flow path 650. Thus, third tube 624 has an inlet 644 fluidly coupled to the right atrium 160 (rather than an outlet).

Impeller 608 creates primary blood flow path 650 from left atrium 184, through first tube 610 and inlet 612 into device 600. The blood flows past impeller 608 through outlet 622 to second tube 620 and through anchor 640 into the aorta 182 of the patient. In addition, device 600 creates a secondary blood flow path 652 from inlet 644 past rotatable element 606, where it joins the blood in primary blood flow path 650 and is propelled into the aorta.

This design causes both oxygenated and deoxygenated blood to flow into the aorta. As a result, the percentage of deoxygenated blood as compared to the oxygenated blood must be kept relatively low. Thus, rotor 606 is configured to draw a mass flow rate of blood through secondary blood flow path that is about 5% to about 10% of blood in the primary flow path.

In another embodiment, pump 600 may be configured such that a portion of the pump extends into left atrium 184. For example, inlet 644 of pump 600 may extend directly into left atrium 184 such that the blood flowing through secondary flow path 652 into the aorta 182 is oxygenated. In some embodiments, pump 600 is anchored across septal wall 632 such that an upstream portion of the pump 600 is disposed in left atrium 184 and a downstream portion of pump 600 is disposed in right atrium 160. In this embodiment, inlet 612 of the primary flow path 650 may also be disposed in left atrium 184, thereby obviating the need for tube 610 and anchor 630. This configuration also provides a stable anchoring point for pump 600 at septal wall 632.

Figure 22:
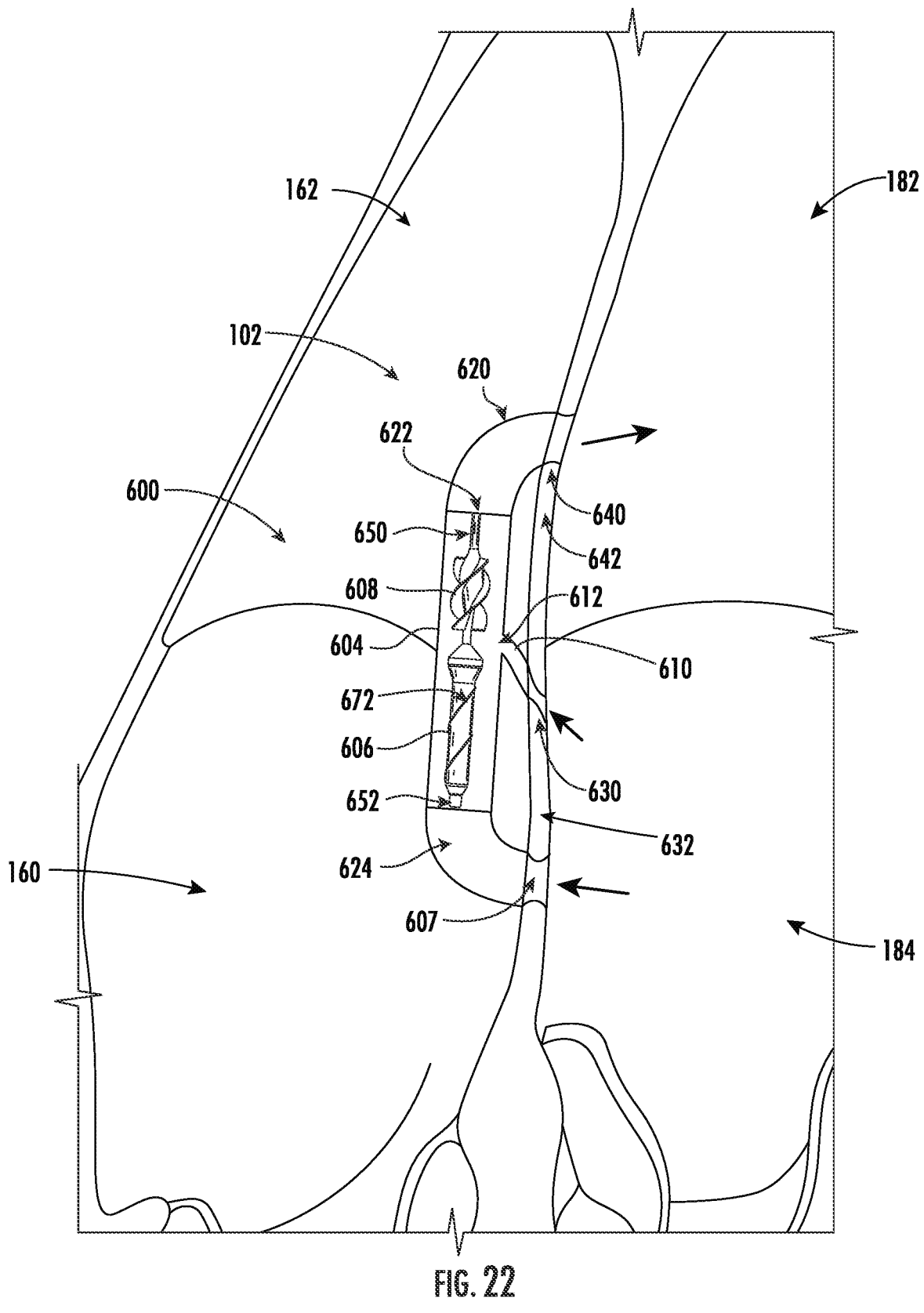
FIG. 22 is a schematic of an axial flow pump in a right atrium of a patient's heart, illustrating a secondary flow path from the left atrium to the aorta.

Referring now to FIG. 22, device 600 has a similar construction as in FIG. 20 above except that third tube 624 is coupled to a third anchor 670. Third anchor 670 is coupled to an inlet of third tube 624 and configured for anchoring tube 624 to septal wall 632 between the right atrium 602 and a left atrium 634 of the patient. Anchor 670 is further configured to create a fluid passage through wall 632 such that blood may flow from the left atrium and into tube 624. Thus, in this embodiment, blood flowing into both the primary and secondary blood flow paths is drawn from the left atrium and propelled directly into the aorta.

Similar to the embodiment shown in FIG. 21, the pump 600 in FIG. 22 may be anchored across septal wall 632 such that a portion of the pump is disposed within left atrium 184. This obviates the need for tubes 624, 610 and anchors 670, 630.

In other embodiments, the pumps described here may be entirely implanted in the left atrium 184. In these embodiments, pump 600 may include one or more tubes or anchors that direct the flow of blood from left atrium 184 through septal wall 632 and second tube 620 such that the blood flows through the wall between the SVC 162 and the aorta 182 of the patient. Alternatively, pump 600 may be configured to direct blood flow from the left atrium directly into the aorta (i.e., without passing into the right atrium or the SVC).

In yet another embodiment, the pumps described herein may be positioned in the left ventricle of the patient and configured to propel blood from the left ventricle directly into the aorta. In these embodiments, the pump may be configured for chronic longer-term implantation, as described above.

Alternatively, the pump may be configured for acute use for mechanical circulatory support of the heart, such as for the treatment of cardiogenic shock, to unload the ventricle and decrease myocardial oxygen consumption. In this embodiment, the pump may be placed percutaneously in the femoral artery using an introducer sheath and advanced in a retrograde fashion across the aortic valve into the left ventricle. In these embodiments, both the primary and secondary blood flow paths described above draw blood from the left ventricle. The secondary flow path may recirculate the blood back into the left ventricle, or it may direct the blood into the aorta along with the primary flow path.

Systems and methods for transferring energy and/or power to an implanted medical device will now be described. In the representative embodiments, the devices are implantable intracardiac devices, such as the ventricular assist devices (VADs) described above. However, it will be recognized that these systems may be used to power mechanical circulatory support devices (MCS), artificial hearts, ECMO devices, implantable heart monitors and defibrillators, pacemakers, or other intracardiac devices as well as patient and disease management devices such implantable pulmonary artery pressure monitors.

Figure 23:
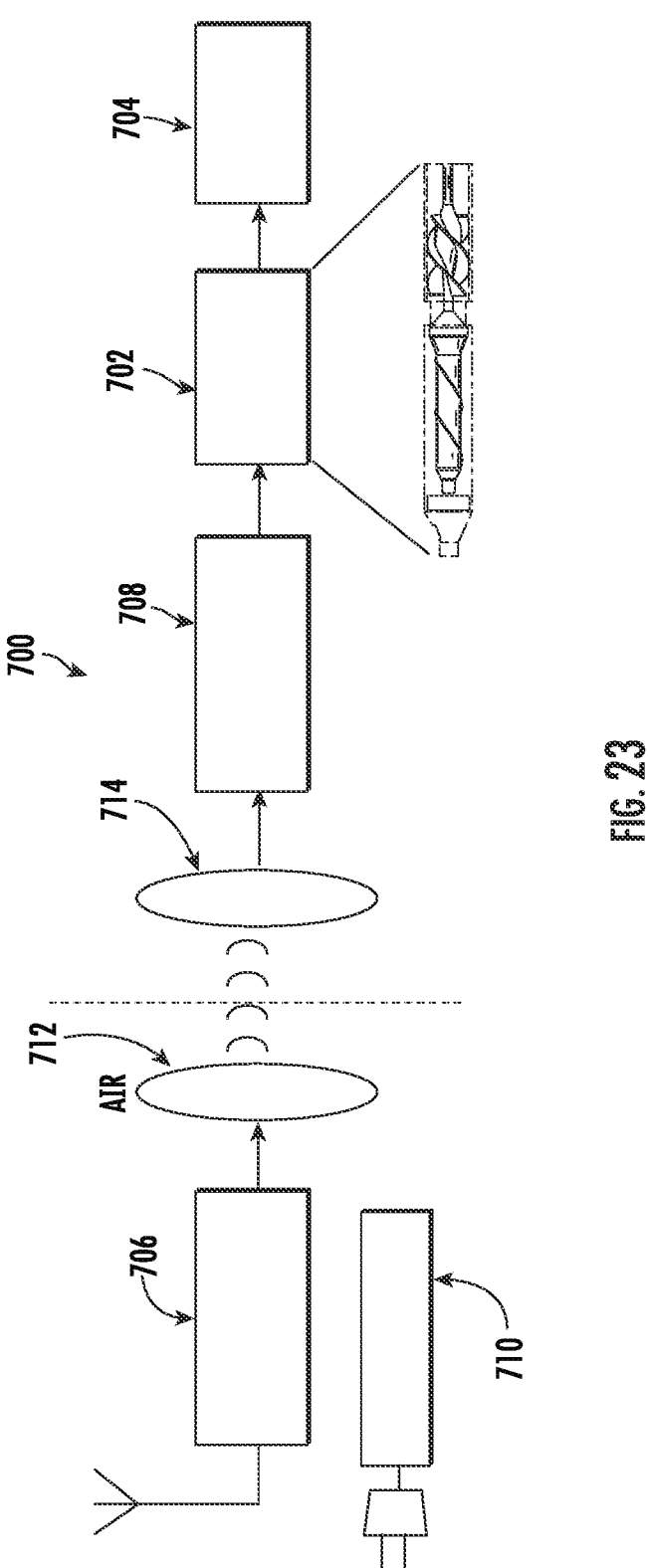
FIG. 23 is a schematic view illustrating various components of a ventricular assist system.
Figure 24:
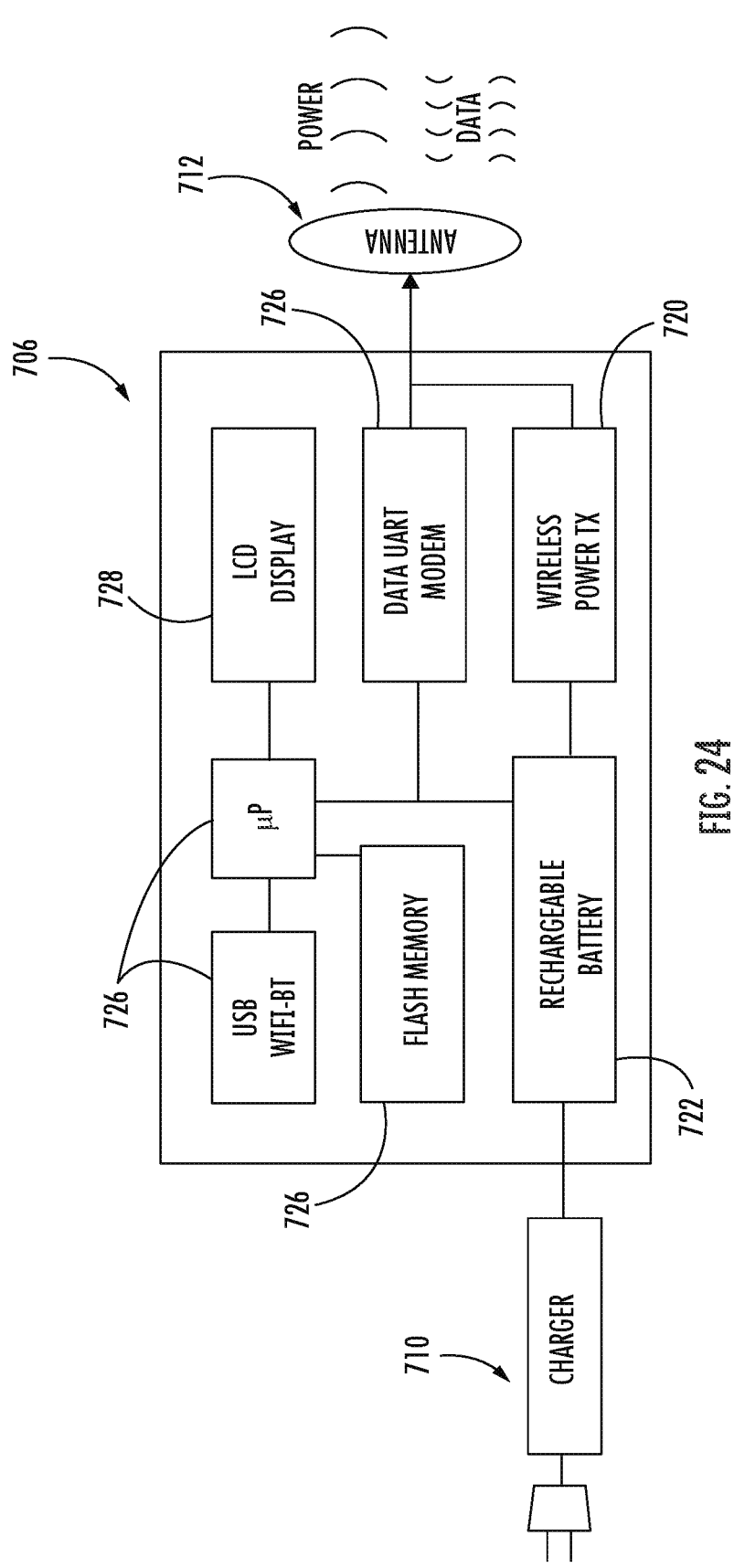
FIG. 24 is a block diagram of an external device that comprises a wireless power transmitter of the system of FIG. 23.
Figure 25:
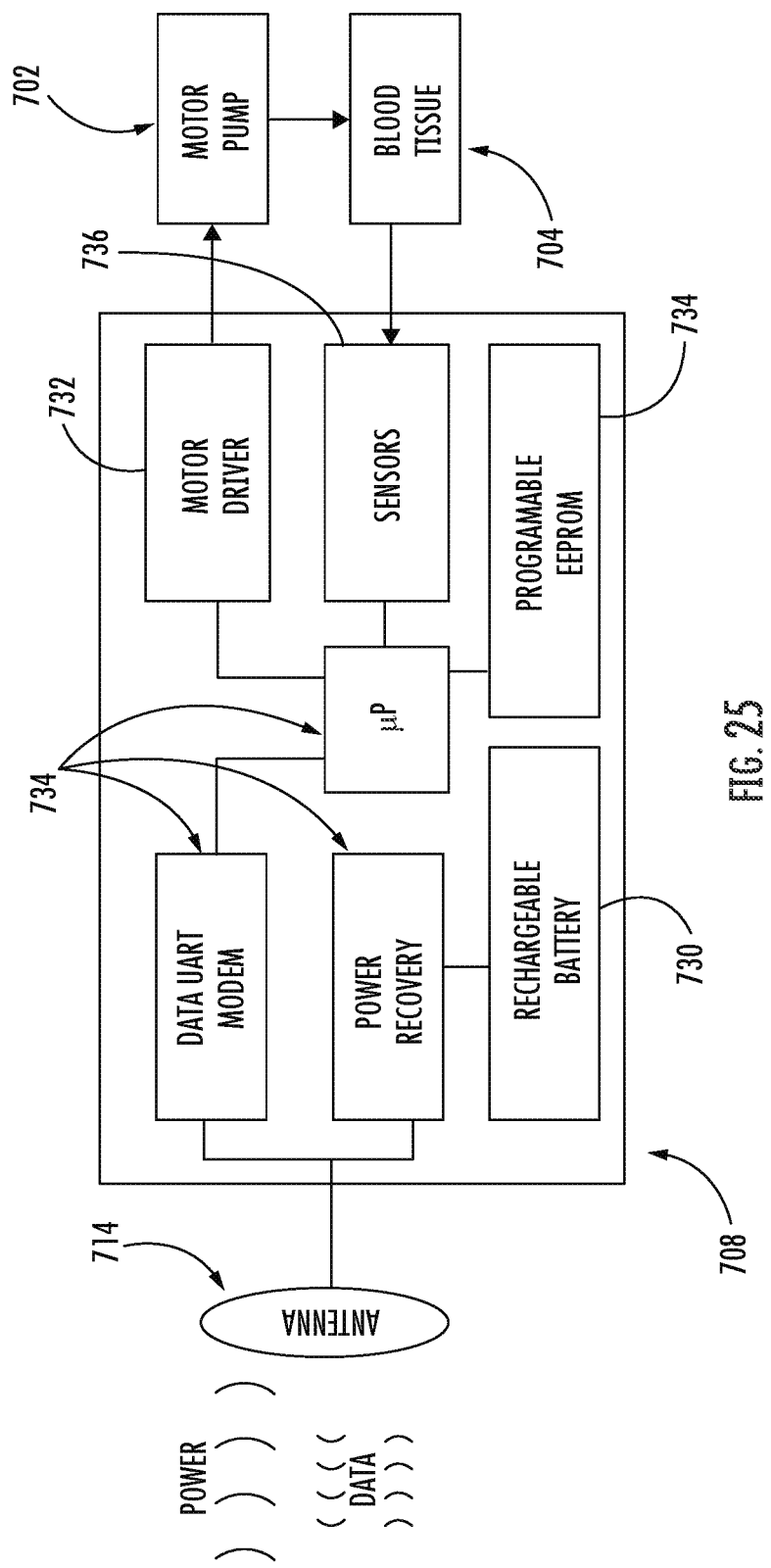
FIG. 25 is a block diagram of an internal controller and wireless receiver of the system of FIG. 23.

FIG. 23 is a flow diagram of ventricular assist system 700 that may include one or more pumps 702, such as the axial pumps described above. System 700 includes an external device 706 that comprises a wireless power transmitter 720, a magnetic coil (not shown), a power source 722, such as a rechargeable battery or the like, an antenna 712 and the associated electronics 726 for transferring energy or power from antenna 712 to an internal controller 708 (see also FIG. 24). In some embodiments, external device 706 may include a user display 728 for providing information to the patient related to various parameters of the system, such as the power delivered to the motor 702, the speed of the pump and the like. User display 728 may also include a user interface that provides input controls for the patient to directly modulate certain parameters of the system (discussed below). Device 706 may also include a suitable coupler for removably coupling the power source to an external charger 710. Alternatively, the power source may be situated remotely from device 706 and may be coupled to device 706 wirelessly or via a direct wired connection (see, for example, FIG. 25).

In certain embodiments, the wireless power transmitter 720 within device 706 includes an amplifier or controller AC power supply that is operably coupled to a drive loop, to provide RF energy to the drive loop. A sensor, such as a directional coupler, vector network analyzer or the like, provides information from the drive loop. The drive loop may comprise a single-turn or multi-turn drive loop.

Device 706 may comprise a wearable device that can be attached to, or worn by, the patient. Preferably, the wearable device is secured near a portion of the patient's body directly over, or near, antenna 714 or internal controller 708. In some embodiments, device 706 also includes an attachment element (not shown) for attaching device 706 to a patient. The attachment element may comprise any suitable releasable coupling element, such as fasteners, snaps, interference fit structures, Velcro and the like. Wearable device 706 may be configured for direct attachment to the patient's outer skin surface or for attachment to a variety of different wearable garments, such as pants, belts, chest straps, pendants, sashes, hats, jackets, shirts, vests, shorts, skirts, bibs, coveralls. The wearable garment may include additional features, such as multiple hardpoints, straps or the like, for ensuring that the antenna contacts the patient's skin surface and engages this surface sufficiently to transmit the power therethrough with minimal losses. The wearable garment may also include a waterproof outer shell around to insulate the antenna, transmitter and associated electronic circuits from water or other fluids that may contact the garment.

System 700 may further include one or more relay resonators (not shown) positioned between external device 706 and internal controller 708. In this embodiment, one or more of the relay resonators may be provided in a wearable device, while device 706 remains in a position remote to the patient. Alternatively, the relay resonator may be disposed in or on a different wearable device. In certain embodiments, the relay resonator may be larger than implanted resonator in controller 708 and is operable to increase the range of the wireless energy transfer.

The internal controller 708 may be implanted in a suitable location within the patient. Controller 708 may be implanted subcutaneously within the patient, or it may be implanted within the patient's heart. Controller 708 comprises an antenna 714 for receiving power from transmitter 706, a power source 730, such as a rechargeable battery, a motor driver 732 for transferring the power to pump 702 and associated electronics 734, such as memory, power recovery, telemetry and the like. Controller 708 may further include one or more sensors 736 that detect a variety of operational parameters for the pump 702, such as the power transmitted to the pump, the pump speed, the maximum output pressure, the negative intake pressure and the like.

Motor driver 732 communicates with pump 702 to drive the pump motor and control blow flow through the pump. In some embodiments, controller 702 wirelessly communicates with the heart pump. In other embodiments, controller 702 is connected to pump 702 via direct wire connections. In other embodiments, controller 708 is integrated into the housing of the heart pump.

Controller 708 may have the ability to monitor the function of the heart pump and/or the cardiac function of the patient. In certain embodiments, controller 708 includes one or more sensing electrodes (not shown) to receive, filter, amplify and analyze an EKG signal. The controller may measure real time function and power consumption of the heart. These measures can then be used to derive many variables of pump function, including speed, flow, suction, pressure head of the pump and an occlusion event. Controller 708 may also have multiple modes, such as a continuous flow mode and/or a pulsatile flow mode, wherein the pump speed is attuned to the systole and diastole periods of the cardiac cycle of the patient. The system may further include an external control unit with a user interface for controlling the specific mode of operation of controller 708, which may include fixed speed (RPM) operation, fixed flow rate operation as well as fixed power operation. A more complete description of one representative controller for use with the system described herein can be found in U.S. Pat. No. 9,919,088, the complete disclosure of which is incorporated herein by reference in its entirely for all purposes.

In some embodiments, internal controller 708 may include a load loop operably connected to provide energy to the pump 702, and a receiver resonator that is inductively coupled to the load loop. During operation, the transmitter resonator and the receiver resonator may form a magnetically coupled resonator (MCR), such that the pump 702 is energized from RF energy from the amplifier that is inductively transmitted from the drive loop, to the MCR, and is inductively transmitted from the MCR to the load loop. MCRs induce power transfer between two components through a matching of the resonance frequency between a source resonator and a receiver resonator. A controller may be operable to receive data from the sensor, and to control the operating parameters to optimize the energy transfer efficiency in the MCR. A more complete description of suitable wireless power transmitters can be found in U.S. Pat. Nos. 8,299,652, 8,827,889 and 9,415,149, the complete disclosures of which are incorporated herein by reference in their entirety for all purposes.

Transmitter 706 is also configured to transmit various control signals to internal controller 708. Likewise, controller 708 is operable to control operation of pump 702 and to transmit data back to transmitter 706. The control signals provide feedback control to the pump based on physiological requirements of the patient. In some embodiments, the control signals are based on the power transferred to the receiver 708. These control signals may, for example monitor the dynamic power coupling between the transmitter and the receiver to ensure the efficient transfer of power therebetween.

Power may be transferred from wearable device 706 through the air 712 and the patient's tissue 714 to internal controller 708. In some embodiments, wearable device 706 may be in direct contact with the patient's tissue, which reduces or eliminates the amount of air 712 in the power transmission pathway. Internal controller 708 then transfers the power to the motor in pump 702, which drives the impeller and provides work to the blood 704 to propel the blood through pump 702. Power may be lost between all of these components due to various inefficiencies. For example, power may be lost between the receiver and transmitter due to a number of factors, including the distance between the coils, the offset between the center of the coils, the substance between the coils and the angle between the coils. The position and orientation of wearable device 706 may, therefore, change the efficiency of this power transfer, which may in turn effect the operation of pump 702. In certain embodiments, the wearable device 706 and/or the internal controller 708 include sensors (not shown) that detect the power transferred from wearable device 706 and the power received by internal controller 708. A controller (not shown) housed within, or coupled to, wearable device 706 calculates the difference between these two power values to ensure that the power loss remains within an acceptable range to operate pump 702.

In certain embodiments, the wearable device 706 and/or the internal controller 708 may also include sensors indicating the position and/or orientation of the wearable device 706 relative to the internal controller 708. In certain embodiments, the sensors indicate the absolute position of the transmitter. In other embodiments, the sensors may indicate the position of the transmitter relative to the receiver. Suitable sensors may include capacitive displacement sensors, eddy-current sensors, Hall effect type position sensors, inductive sensors, laser doppler sensors, linear variable differential transformers (LVDTs), photodiode arrays, piezoelectric transducers, position encoders, potentiometers, optical proximity sensors, magnetic angle sensors, TMR, GMR or AMR angle sensors, orientation sensors, RF interferometry based sensors and the like. The sensors may be coupled to external device 706, internal controller 710 or both. The controller is configured to compare the position and orientation of the transmitter and receiver with the power delivered to the motor within the pump to, for example, determine if the wearable device 706 is positioned correctly on the patient (i.e., at the optimal distance, angle and/or coil center offset to achieve an acceptable power transfer therebetween).

In one such embodiment, system 700 includes sensors that detect the physical distance between the antenna coils in wearable device 706 and internal controller 708. The sensors are coupled to the controller and configured to transmit this distance to the controller, either wirelessly, or through wearable device 706. The controller is configured to compare this distance with the power loss detected between the receiver and the transmitter and/or the absolute power delivered to the motor within the implanted device to determine if the coils are, for example, positioned close enough to each other to provide sufficient power transfer to operate pump 702. In some embodiments, controller uses the extra power received to charge an implanted battery and drain energy from it when the received power is insufficient.

In another embodiment, system 700 includes one or more sensors that detect the relative angle of the coils in transmitter 706 and receiver 708. The sensors are coupled to the controller and configured to transmit this angle data to the controller. The controller is configured to compare this angle data with the power loss detected between the receiver and the transmitter and/or the absolute power delivered to the motor within the implanted device to determine if the coils are, for example, oriented at an angle close enough to parallel to provide sufficient power transfer to operate pump 702.

In yet another embodiment, system 700 includes one or more sensors that detect the offset (if any) between the centers of the coils on the transmitter and the receiver. The sensors are coupled to the controller and configured to transmit this data to the controller. The controller is configured to compare this data with the power loss detected between the receiver and the transmitter and/or the absolute power delivered to the motor within the implanted device to determine if the coils are, for example, centered relative to each other to provide sufficient power transfer to operate pump 702.

In certain embodiments, one or more of the controllers is configured to automatically adjust parameters of the wireless power based on either detecting the power delivered to the motor within the pump (i.e., if this power drops below a threshold level), or detecting changes in the relative position and/or orientation of the magnetic coils in the transmitter and receiver. In certain embodiments, the power delivered to transmitter 706 may be adjusted directly to account for these changes. In other embodiments, the frequency of the amplifier is adjusted to adapt to changes in the position and/or orientation of the magnetic coils in the transmitter and receiver. In yet another embodiment, the coupling between the magnetic coils is actively controlled with one or more matching networks that are operable to adjust the impedance in the system, such that the power level delivered to the motor remains at or above a threshold level.

System 700 may further comprise a user interface (not shown) within user display 728 or wirelessly coupled to external device 706 and including one or more alert indicators that indicate whether the wearable device is positioned at the optimal distance and/or orientation relative to the receiver 708. The alert indicators may be visual, audible, tactile (e.g., vibration) or the like, and they may be housed on, or within, wearable device 706 or wirelessly coupled to wearable device 706, for example, on a separate mobile device or the like. The user interface provides immediate feedback to the patient and/or the healthcare professional that the wearable device 706 should be repositioned to establish sufficient power transfer to pump 702.

In one such embodiment, the user interface includes one or more position indicators that indicate: (1) a distance between the wearable device 706 and the receiver 708; and/or (2) the positional offset between the centers of the coils in these two devices. The position indicator alerts the patient if the wearable device 706 is not positioned properly to achieve an efficient power coupling with the receiver 708.

In another embodiment, the wearable device 706 includes an angle indicator that alerts the patient of an unsuitable angle between the coils. Generally, the closer these two coils are to a parallel angle relative to each other, the less power will be lost during transfer. This angle indicator provides an alert to the patient if the wearable device 706 needs to be repositioned to reestablish this angle.

In certain embodiments, system 700 is configured to automatically provide a constant level of power to pump 702 and/or to blood 704. This ensures that pump 702 will continuously pump blood flow through the heart at a sufficient rate regardless of any changes in the system that would otherwise reduce this level of power, such as power loss due to inefficiencies and/or changes in the relative positions of the coils within the transmitter and receiver, including the distance between the coils, the offset between the center of the coils, changes in the substance(s) or material(s) located between the coils and the angle between the coils.

In this embodiment, the implant will include a sensor (not shown) for continuously measuring the power received by the pump. This sensor may be, for example, housed within the implant housing and coupled to the power electronics provided to the pump. The sensor is coupled to internal controller 708 (either directly through wired connections or wirelessly). Internal controller 708 receives this data related to the power received by the pump and transmits it to an external controller (e.g., controller 712 shown in FIG. 1) that is coupled to, or disposed within, external device 706. External device 706 is configured to modulate one or more of the parameters of the wireless power transmission based on this data, such that the power received by the pump remains substantially constant, e.g., about 5 Watts to about 20 Watts, or about 7 Watts to about 17 Watts. In an exemplary embodiment, the second lever of power is about 15 Watts.

The system is preferably configured to deliver a constant amount of power to the pump to ensure that the pump draws flows through the heart at a target rate. In an exemplary embodiment, the target power delivered to the blood is about 1.5 W to about 2.0 W or about 1.73 W, which is sufficient power to pump at least about 6 Liters of blood per minute or 100 mL/second (i.e., based on a mean arterial pressure (MAP) of about 130 mm Hg). In this regard, the implant may include an additional sensor located, for example, within the implant housing near its outlet to measure the power delivered by the pump to the blood. This additional sensor may be coupled to internal controller 708 such that the system can modify parameters in the event that the pump is not transferring the target power to the blood.

In certain embodiments, the controller is programmed to direct a continuous level of power (and thus a continuous level of blood flow through the pump). In other embodiments, the controller is programmed to direct pulsatile flow that may be, for example, synchronized with physiological blood flow through the patient's heart. For example, the power level (or the speed of the pump) may be increased or decreased during a systole or diastole state in the heart.

Figure 26:
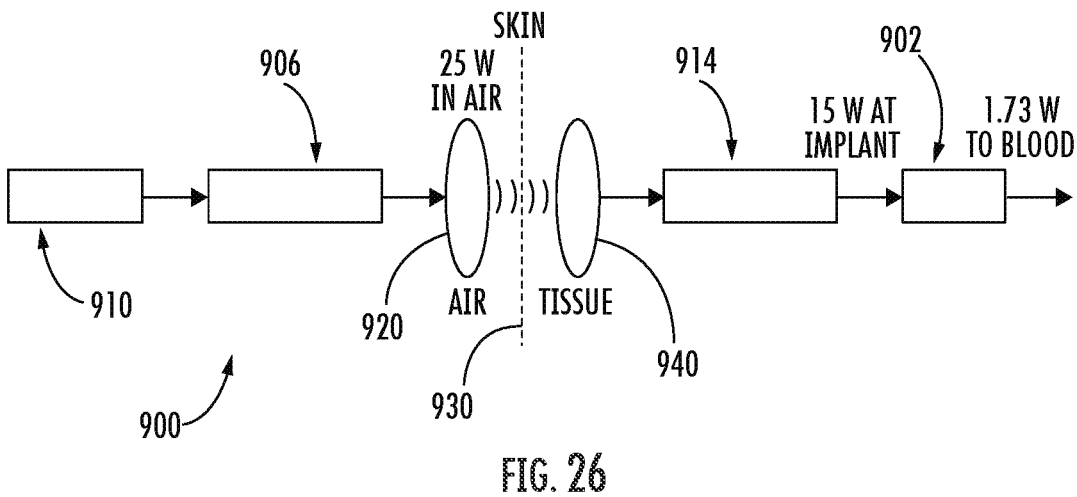
FIG. 26 is a schematic view illustrating wireless power transfer with the system of FIG. 23.

FIG. 26 illustrates a more simplified version of a system 900 that includes a power source 910, a transmitting resonator 906, a receiving resonator 914 and an implanted device 902 that may include a motor and a pump, as described above. As shown, system 900 will provide a constant power level of about 5 W to about 20 W to the pump, preferably about 13 W to about 17 W, or about 15 W. This power level, however, is lost as it is transmitted from power source 910, through resonator 906, the air 920, the patient's skin 930, the patient's tissue 940 and the implanted device 902. Thus, system 900 is designed such that power source 910 generates about 20 W to about 40 W, preferably about 30 W, of power. Transmitting resonator 906 is designed to delivery this power through air 920, skin 930 and tissue 940 to receiving resonator 914, which delivers about 10 to 20 W, or about 15 W, to implanted device 902. Device 902 may include one of the embodiments described and delivers about 1 W to 3 W, or about 1.5 to 2 W, preferably about 1.73 W, to the blood flowing through device 902 at a rate of approximately 6 Liters/minute. Power usage would be less at lower flow rates, such as 4 Liters/minute.

The overall efficiency of the system ensures that an appropriate amount of power is transmitted to the device 902 regardless of any other inefficiencies in the pathway between the energy source 910 and the receiving resonator 914. In certain embodiments, the power level transmitted to the implanted device is at least about 40% of the power level transmitted from the energy source 910, preferably at least about 50%.

The system also is configured to minimize the specific absorption rate (SAR) of the tissue 940 between the transmitting and receiving resonators. The SAR is generally defined as the measure of the rate of radiofrequency (RF) energy absorption within the body tissue. In certain embodiments, the system is configured to maintain the SAR at or below about 1.5 W/Kg.

Figure 27:
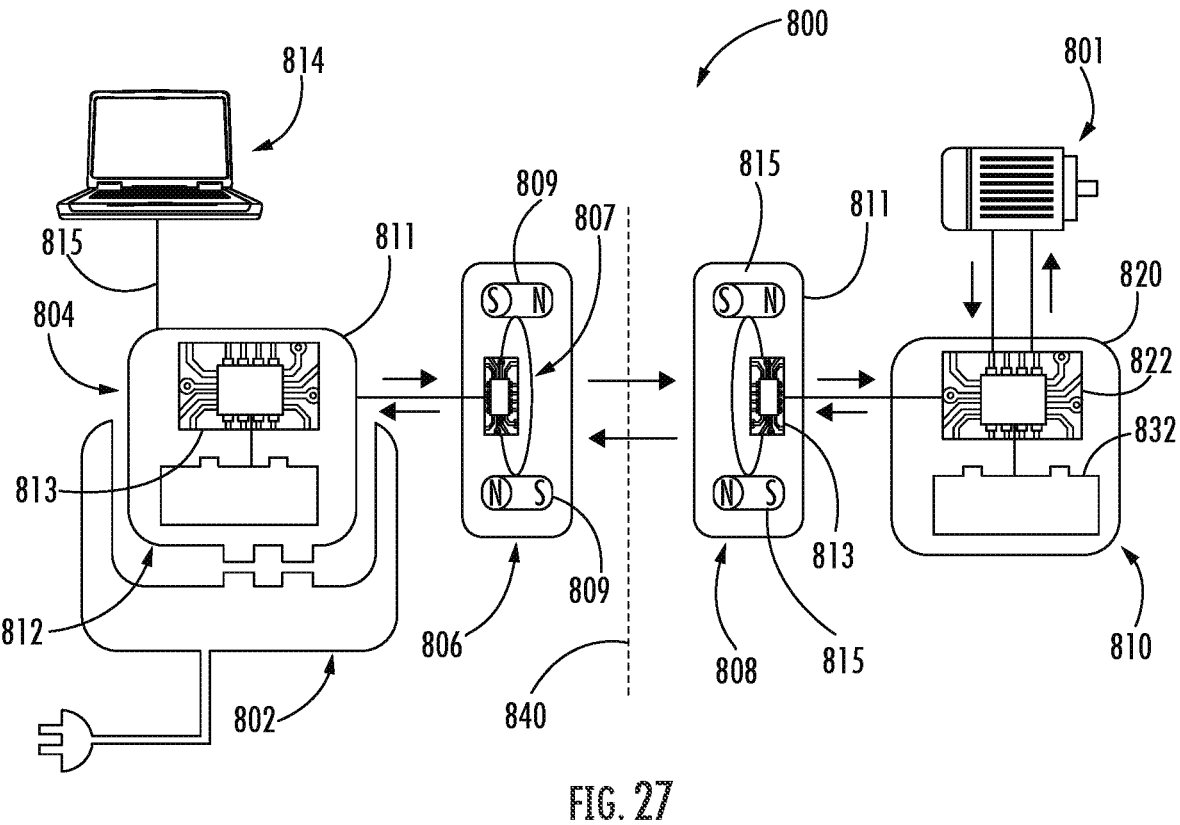
FIG. 27 is a schematic view of a system for transferring power to an implanted medical device.

FIG. 27 illustrates another ventricular assist system 800 that may include one or more implantable pumps 801, such as the axial pumps described above. System 800 includes a first module 802, a second module 804 and a third module 806 that are located external of outer skin surface 840 of the patient and a fourth module 808 and a fifth module 810 that are located within the patient. Module 802 generally functions as an external battery charger, such as a DC or AC battery charger, for charging module 804. In an exemplary embodiment, module 802 operates with an AC supply in the range of about 110V to about 240 V and a frequency of about 50 Hz to about 60 Hz. It can also be a DC source, such as USB or 12 Volt cigarette lighter adapter. Module 802 is capable of charging a battery of at least about 800 kJ within about 2 hours (average 100 Watts, peak 200 Watts).

Module 804 comprises a housing 811 and a power source 812, such as a rechargeable battery, within housing 804 for providing power to module 806. In an exemplary embodiment, the rechargeable battery provides usable power of at least about 500 kJ to about 1,000 kJ, or about 750 kJ to about 850 k J, or about 800 kJ and is configured to inhibit or prevent deep discharge of the battery within to prolong its life. Module 804 may also include a suitable coupler for removably coupling the power source to module 802. Alternatively, the power source may be situated remotely from module 802 and may be coupled to module 802 via a direct wired or a wireless connection.

Module 804 may contain suitable electronics 813 for controlling the parameters of the power delivered to module 806. Module 804 may also include an electrical connection 815 to a computer or other processing device 814. Processing device 814 may provide a variety of software programs and memory for transferring data to and from system 800. Module 804 may be coupled to processing device 814 via wired connections, such as Ethernet, USB, RS-232 or the like, or wirelessly, such as WIFI, Bluetooth or the like.

Module 806 comprises a transmitting antenna 807 and the associated electronics for transferring energy or power from the antenna to internal modules 808, 810. Antenna 807 includes a magnetic coil that preferably has a diameter of about 20 cm or less and may be flexible or rigid. Module 806 may further include one or more magnets 809 to assist with the positioning of a transmitting antenna 807 relative to an implanted antenna 813 within Module 808. Module 806 may also be configured to provide visual or other feedback related to the alignment of coils within antennas 807, 813 within module 806 and module 808. In an exemplary embodiment, module 806 is configured to perform all of its functions with a maximum power consumption of about 30 Watts. Module 806 is further configured to transfer power in the range of about 20 to about 28 Watts, preferably about 25 Watts, to module 808.

In an exemplary embodiment, module 808 comprises a housing 811 that is implanted within the patient, e.g., subcutaneously. Housing 811 preferably comprises a water-tight material, such as ceramic or the like, that hermetically seals housing 811 to ensure that the components within remain insulated from bodily fluids. Module 808 comprises a receiving antenna 813 and power recover circuitry, e.g., rectifiers or the like. Receiving antenna 813 includes a magnetic coil with a diameter that is preferably about 7 to 10 cm and may be flexible or rigid. Module 808 will also include one or more magnets 815 that cooperate with the magnet(s) 809 in module 806 to improve the relative positioning of module 806 and ensure that a constant level of power is delivered to the implant. Module 808 recovers RF power and is preferably configured to produce at least about 15 Watts of power to the implanted medical device 801. Module 808 operates with 24 Volts DC and may transmit data using in band or out of band modulation.

In one embodiment, RF electronics are disposed within module 806 and configured to provide a DC connection between modules 806 and 808. In another embodiment, RF circuitry is housed within module 806 and configured to provide an RF connection with module 808. In yet another embodiment, modules 806 and 808 are combined into a single housing to product a more compact design. In this embodiment, modules 806, 808 may be located externally of the patient, or implanted within the patient subcutaneously or in a location closer to module 810.

Module 810 comprises an implantable housing 820 that includes a controller 822 for controlling a motor within the implanted medical device 801, which may, for example, comprise an implantable pump for assisting with cardiac function as described above. Housing 820 preferably has a volume of 40 cc or less. Module 810 may further include a rechargeable battery 832 for providing short-term power to the pump within device 830 when, for example, external power is not available. In an exemplary embodiment, battery 832 has at least about 20 kJ power. System 800 may further include a wired or wireless connection between module 808 and module 810 for transferring power and/or data therebetween. In an exemplary embodiment, this connection is permanent. In certain embodiments, system 800 includes another wired or wireless connection between module 810 and device 801 to transfer power and data between module 810 and the motor 824. In an exemplary embodiment, this electrical connection is industry standard IS-1.

Referring now to FIGS. 28-37, preferred embodiment of magnetic coils for the transmitting and receiving resonators will now be described. In certain embodiments, the transmitting and resonating coils are step up/step down resonant coil pairs. Preferably, each of the transmitting and receiving resonators comprise at least two coils.

Generally speaking, the resonators will comprise a housing having an outer surface and an interior. The magnetic coil is located on the outer surface and the electronics to drive the coil in the interior of the housing. The housing may be any suitable shape. In one embodiment, the housing for the transmitting coil generally has a circular shape with a domed outer surface. the housing for the receiving coil may be the same shape as the transmitting coil, or a different shape. In one embodiment, the receiving coil housing is substantially rectangular. Preferred coil designs include substantially spiral windings that extend around the outer surface from a starting position near the outer edge of the outer surface to an end position near the center of the outer surface. In preferred embodiments, the spiral winding will extend around a central portion of the outer surface (i.e., the winding will leave a substantially open area in the center of the outer surface of the housing). In certain embodiments, the spiral windings will each have between about 2 to about 10 turns, preferable between about 4 to about 7 turns.

The transmitting coil(s) will typically be placed a distance of about 1.0 cm to about 6.0 cm, preferably about 2.0 cm, from the receiving coil(s). This distance will be occupied by the subcutaneous fat and skin tissue in the patient's outer skin surface, garment of the patient, fabric used for the construction of the vest worn by the subject as well as the material used for the encapsulation of the coils. During operation, the coils may be displaced from each other (i.e., shifted horizontally) and/or distanced from each other (i.e., moved toward and away vertically). This displacement may occur inadvertently (i.e., suboptimal placement of the coil, or movement of the patient after the transmitting coil has been), or it may be controlled by the system to maintain power levels, power efficiency and other parameters of the system. As discussed previously, the system ensures that the overall power efficiency and the power transmitted by the receiving resonator to the implant remains substantially constant despite such displacements between the receiving and transmitting coils, which could be accomplished by increasing the transmitter power or adjusting the coil and/or circuit parameters dynamically.

Preferred embodiments of the transmitting coil(s) are shown in FIGS. 28 to 33. The transmitting coil will prefer-ably have a diameter of less than about 20 cm. In certain embodiments, the transmitting coil is flexible and capable of movement relative to the receiving coil. The coil may comprise a conductor on any suitable material, such as polyimide, fiberglass-reinforced epoxy (e.g., FR4) or the like. In certain embodiments, the coil comprises a loop outer diameter of about 50 mm to about 110 mm and a coil outer diameter of about 100 mm to about 120 mm. The trace width of the representative coils is about 2.2 mm to about 2.7 mm, preferably about 2.5 m to about 2.6 mm and more preferably 2.588 mm and the pitch is from about 3 mm to about 10 mm, preferably about 4.5 mm to about 7.2 mm, or about 4.588 mm to about 7.088 mm (center to center), although it will be recognized that other configurations may be employed.

Figures 28, 29, 30, 31:
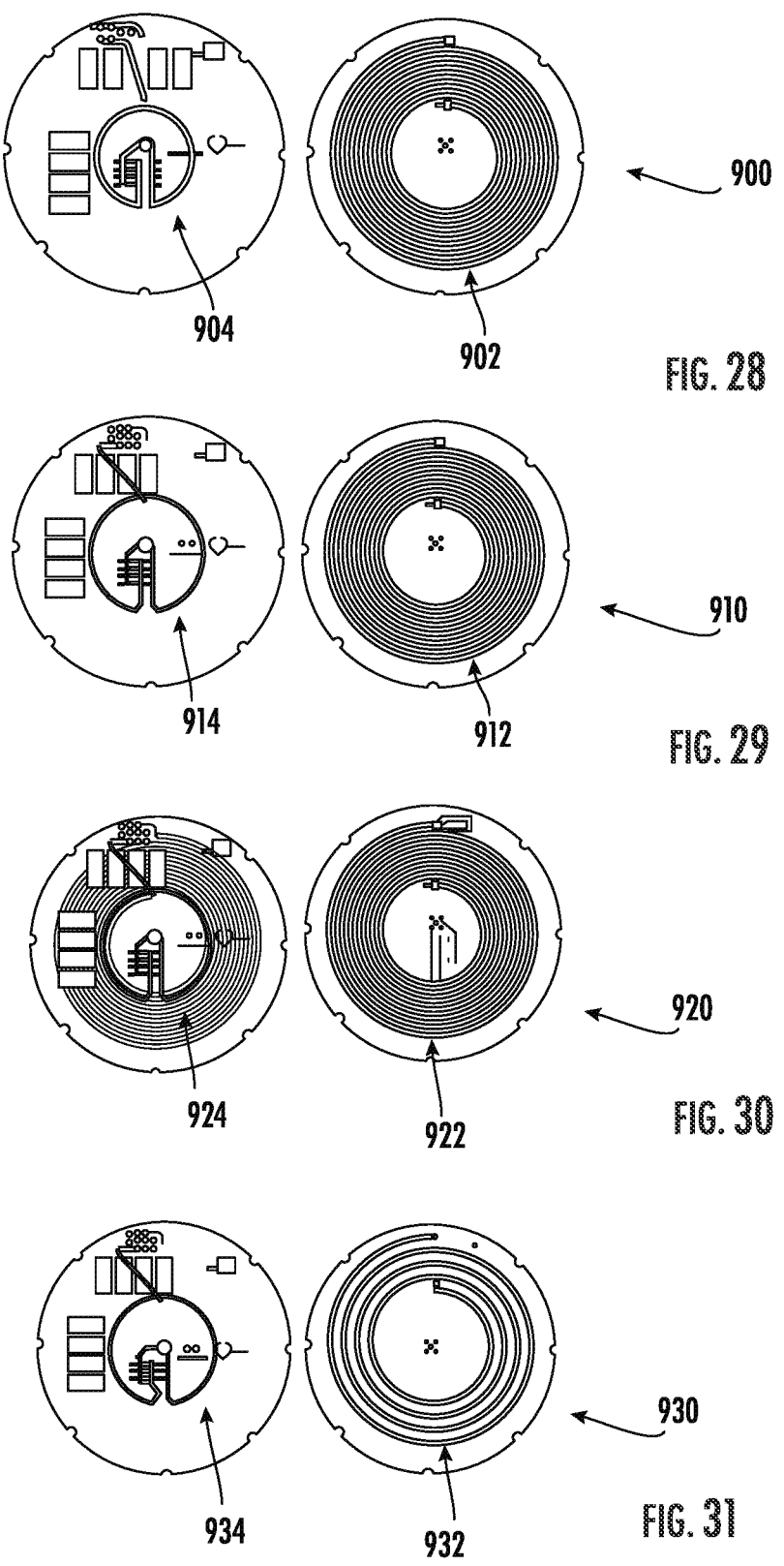
FIGS. 28-33 illustrate various embodiments of transmitting antennas or coils.

Referring now to FIG. 28, a transmitting coil 900 com-prises a housing with internal electronics 904 and a sub-stantially spiral continuous coil 902 having 7 turns on its outer surface. The coil includes a loop outer diameter (OD) of about 50 mm, a coil OD of about 110 mm, a trace width of about 2.588 mm and a pitch (center to center) of about 4.588 mm. The substrate was FR-4.

Referring now to FIG. 29, a transmitting coil 910 com-prises a housing with internal electronics 914 and a sub-stantially spiral continuous coil 912 having 7 turns on its outer surface. The coils includes a loop outer diameter (OD) of about 60 mm, a coil OD of about 110 mm, a trace width of about 2.588 mm and a pitch (center to center) of about 4.588 mm. The substrate was FR-4.

Referring now to FIG. 30, a transmitting coil 920 com-prises a housing with internal electronics 924 and a sub-stantially spiral continuous coil 922 having 7 turns on its outer surface. The coils includes a loop outer diameter (OD) of about 60 mm, a coil OD of about 110 mm, a trace width of about 2.588 mm and a pitch (center to center) of about 4.588 mm. The substrate was polyimide.

Referring now to FIG. 31, a transmitting coil 930 com-prises a housing with internal electronics 934 and a sub-stantially spiral continuous coil 932 having 4 turns on its outer surface. The coils includes a loop outer diameter (OD) of about 60 mm, a coil OD of about 110 mm, a trace width of about 2.588 mm and a pitch (center to center) of about 7.088 mm. The substrate was FR-4.

Figures 32, 33, 34:
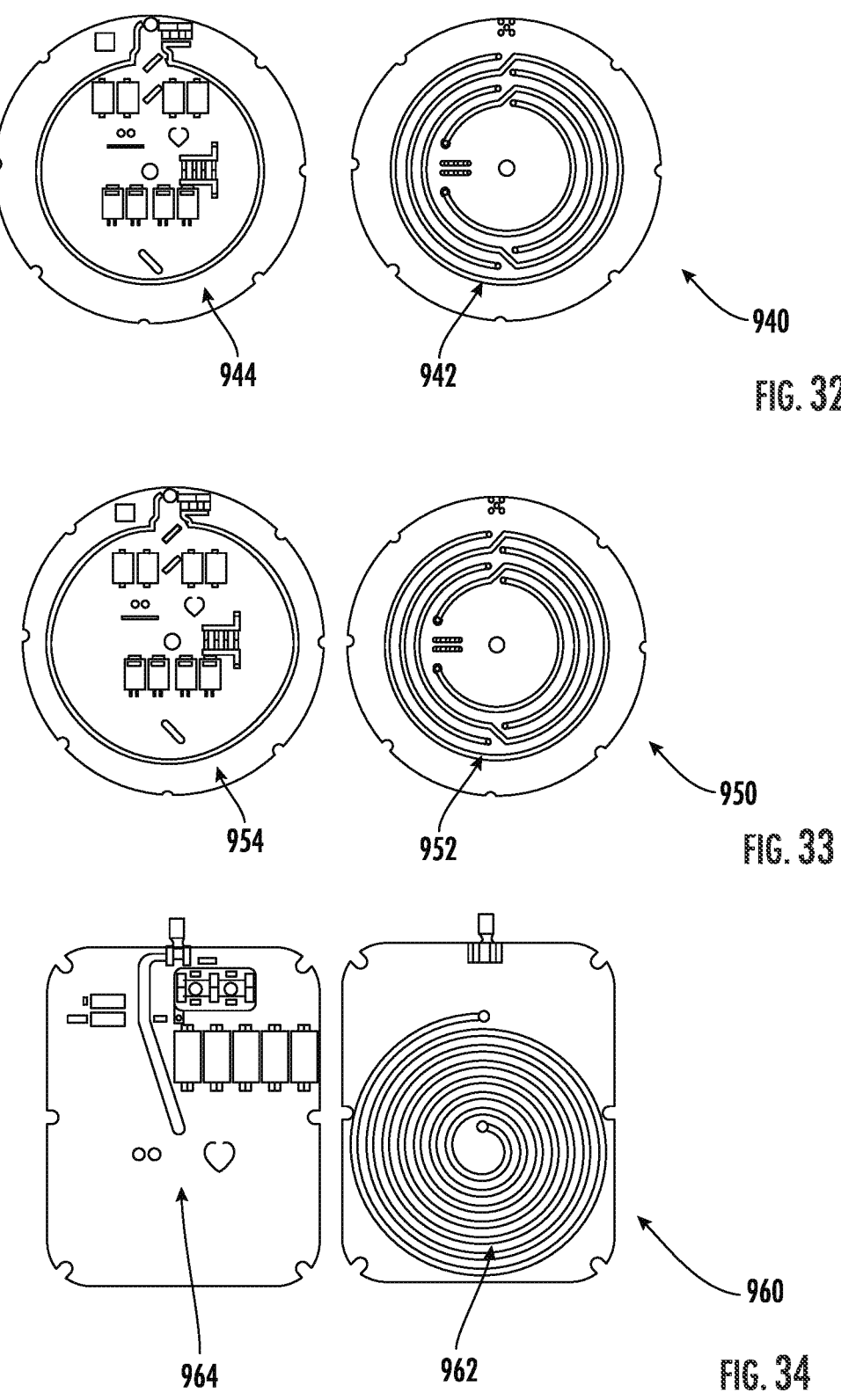
FIGS. 34-37 illustrate various embodiments of receiving antennas or coils.

Referring now to FIG. 32, a transmitting coil 940 com-prises a housing with internal electronics 944 and a sub-stantially spiral coil 942 having 4 turns on its outer surface. The coils includes a loop outer diameter (OD) of about 100 mm, a coil OD of about 110 mm, a trace width of about 2.588 mm and a pitch (center to center) of about 7.088 mm. The substrate was FR-4. In this embodiment, the spiral coil is a concentric design with multiple discontinuous compo-nents. As shown, the coil 942 includes multiple concentric portions that are discontinuous with each other.

Referring now to FIG. 33, a transmitting coil 950 com comprises a housing with internal electronics 954 and a substantially spiral coil 952 having 4 turns on its outer surface. The coils includes a loop outer diameter (OD) of about 110 mm, a coil OD of about 110 mm, a trace width of about 2.588 mm and a pitch (center to center) of about 7.088 mm. The substrate was FR-4. In this embodiment, the spiral coil is a concentric design with discontinuous components. As shown, the coil 930 includes multiple concentric portions that are discontinuous with each other.

Preferred embodiments of the receiving coil(s) are shown in FIGS. 34 to 37. The receiving coil will preferably have a diameter of less than about 10 cm, preferably between about 7 cm to about 10 cm. In certain embodiments, the receiving coil is flexible and capable of movement relative to the transmitting coil. The coil may comprise any suitable mate-rial, such as polyimide, fiberglass-reinforced epoxy (e.g., FR4) or the like. In certain embodiments, the coil comprises a loop outer diameter of about 60 mm to about 80 mm and a coil outer diameter of about 100 mm to about 120 mm. The trace width of the representative coils is about 2.2 mm to about 2.7 mm, preferably about 2.588 mm and the pitch is from about 3 mm to about 10 mm, preferably about 4.588 mm to about 7.088 mm (center to center), although it will be recognized that other configurations may be employed.

Referring now to FIG. 34, a receiving coil 960 comprises a housing with internal electronics 964 and a substantially spiral continuous coil 962 having 7 turns on its outer surface. The coils includes a loop outer diameter (OD) of about 70 mm, a trace width of about 2.588 mm and a pitch (center to center) of about 7.088 mm. The substrate was FR-4.

Figure 35:
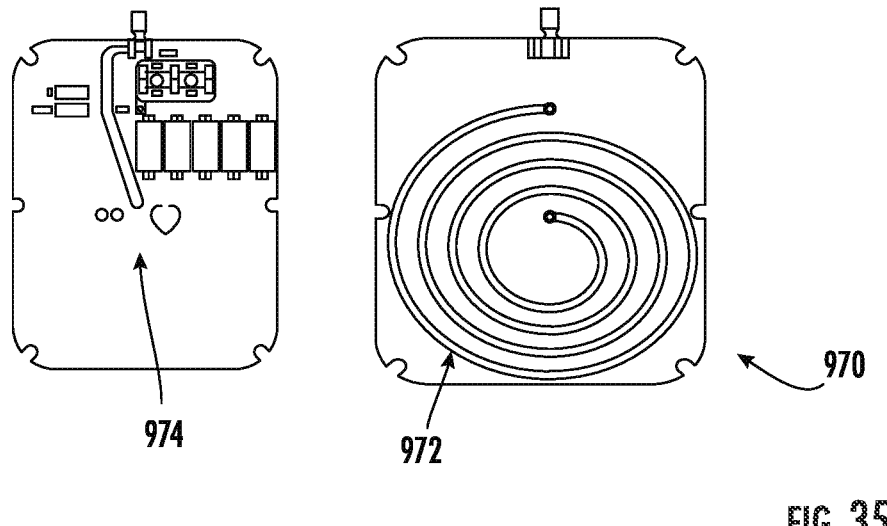

Referring now to FIG. 35, a receiving coil 970 comprises a housing with internal electronics 974 and a substantially spiral continuous coil 972 having 4 turns on its outer surface. The coils includes a loop outer diameter (OD) of about 70 mm, a trace width of about 2.588 mm and a pitch (center to center) of about 7.088 mm. The substrate was FR-4.

Figure 36:
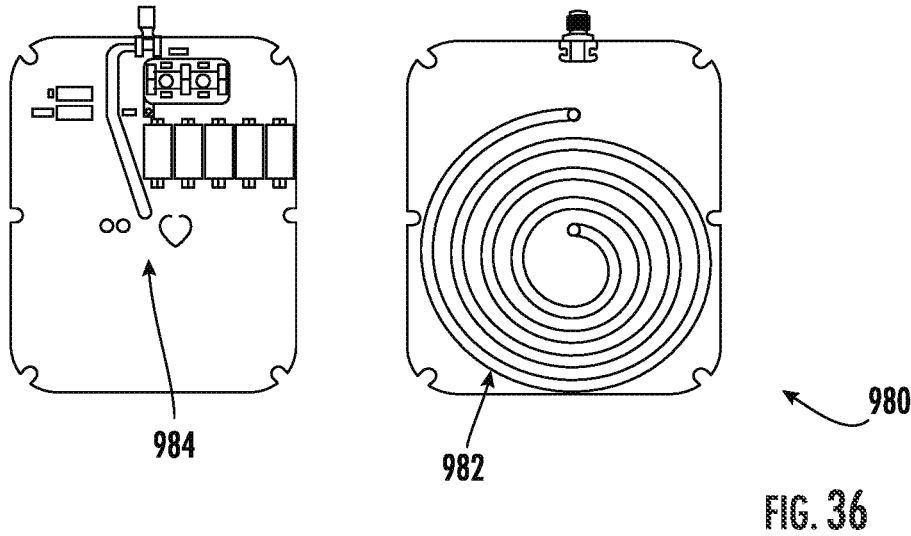

Referring now to FIG. 36, a receiving coil 980 comprises a housing with internal electronics 984 and a substantially spiral continuous coil 982 having 4 turns on its outer surface. The coils includes a loop outer diameter (OD) of about 70 mm, a trace width of about 2.588 mm and a pitch (center to center) of about 7.088 mm. The substrate was FR-4.

Figure 37:
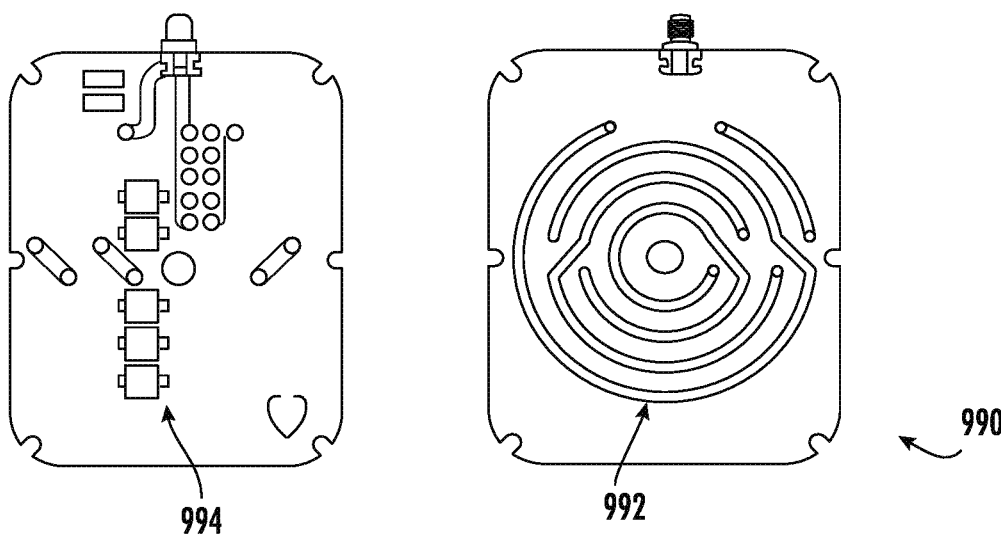

Referring now to FIG. 37, a receiving coil 990 comprises a housing with internal electronics 994 and a substantially spiral coil 992 having 4 turns on its outer surface. The coils includes a loop outer diameter (OD) of about 70 mm, a trace width of about 2.588 mm and a pitch (center to center) of about 7.088 mm. The substrate was FR-4. In this embodi-ment, the spiral coil is a concentric design with discontinu-ous components. As shown, the coil 980 includes multiple concentric portions that are discontinuous with each other.

Applicant conducted a number of comparative bench tests of the transmitting and receiving coils described in FIGS. 28-37. These tests compared the operating range, power and temperature of each of each other transmitting coils 900-950 with each of the receiving coils 960-990. Applicant conducted these tests with different types of tissue, include, muscle, fat, bone and skin, by changing the distance between the coils from 14 mm to 82 mm while the transmitter power was in the range of 38 Watts to 80 Watts and the receiver power was in the range of 20 Watts to 41 Watts. Highest temperature increase observed on the coil surfaces was 11° C. In each test, Applicant measured the transmitting power of the transmitting resonator coil(s) and the output of the receiving resonator coil(s) to ensure that the output power or voltage at the receiver remains substantially constant even when there was a reduction in coupling between the receiver and the transmitter.

Applicant discovered that the optimal combination of transmitter and receiver coils during this bench testing was the transmitting coil 940 shown in FIG. 32 and the receiving coil 960 shown in FIG. 35. This combination of transmitting and receiving coil passed all of the tests related to operating range, power and temperature.

Applicant further discovered another combination of transmitter and receiver coils that partially passed the bench testing, where the partial passage was defined as the antenna pairs meeting some, but not all of the test requirements. Test requirements were power transfer efficiency >50%, being able to maintain operation while coil separation distance is 4 cm or more, power reflection coefficient, aka S11, being less than −10 dB and surface temperature of the coils in air being less than 40° C. This combination was the transmitting coil 950 shown in FIG. 33 and the receiving coil 990 shown in FIG. 37.

Based on this testing, Applicant has demonstrated that the preferred design of a transmitting coil includes a concentric design with multiple discontinuous components that combine to provide 4 turns. Applicant has also demonstrated that the preferred design of a receiving coil includes a coil OD of 70 mm and 4 turns with either a substantially continuous spiral or a concentric design.

Figure 38:
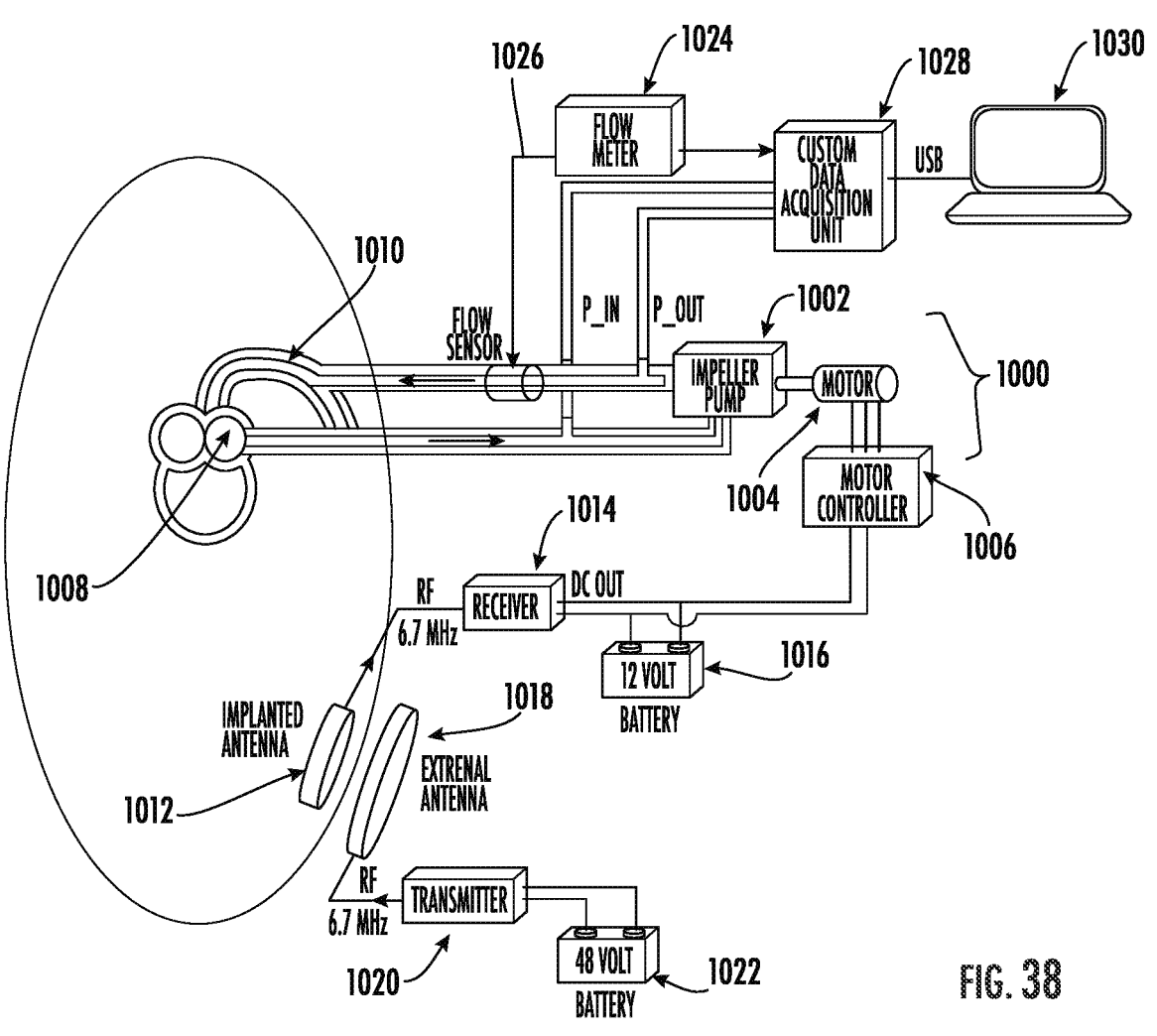
FIG. 38 illustrates an in vivo testing apparatus for the wireless power system described here.

Applicant also conducted in vivo testing of a fully battery operated wireless power system such as the one described herein for a pump 1000 with a swine model. As shown in FIG. 38, pump 1000 includes an impeller 1002, a motor 1004 and a motor controller 1006. The pump 1000 was suitably coupled to the pig's heart to draw blood from a heart chamber 1008 to the aorta 1010. The motor controller 1006 was powered by an implanted receiver antenna 1012 via a receiver 1014 powered by a battery 1016. The implanted antenna 1012 was, in turn, wirelessly powered by an external antenna 1018. External antenna 1018 received power from a transmitter 1020 coupled to a battery 1022.

A flow meter 1024 was connected to a flow sensor 1026 on the blood flow pathway between impeller 1002 and the aorta 1010 to measure the blood flow output of the pump 1000. A custom data acquisition unit 1028 was coupled to both the output and input lines of pump 1000 to measure pressure and other parameters. Acquisition unit 1028 was, in turn, coupled to a processor 1030, having a display for displaying the results of the testing.

In this testing, Applicant measured the transmitter current, the receiver current and the displayed current from the receiver. The input power delivered by the transmitter was 48 Watts (998 mA and 48 Volts). The output power delivered by the receiver to the pump was 28 Watts (2.0 Amps and 12 Volts). Thus, the ratio of output power to input power or efficiency of the wireless power system was 58.3%.

Figure 39:
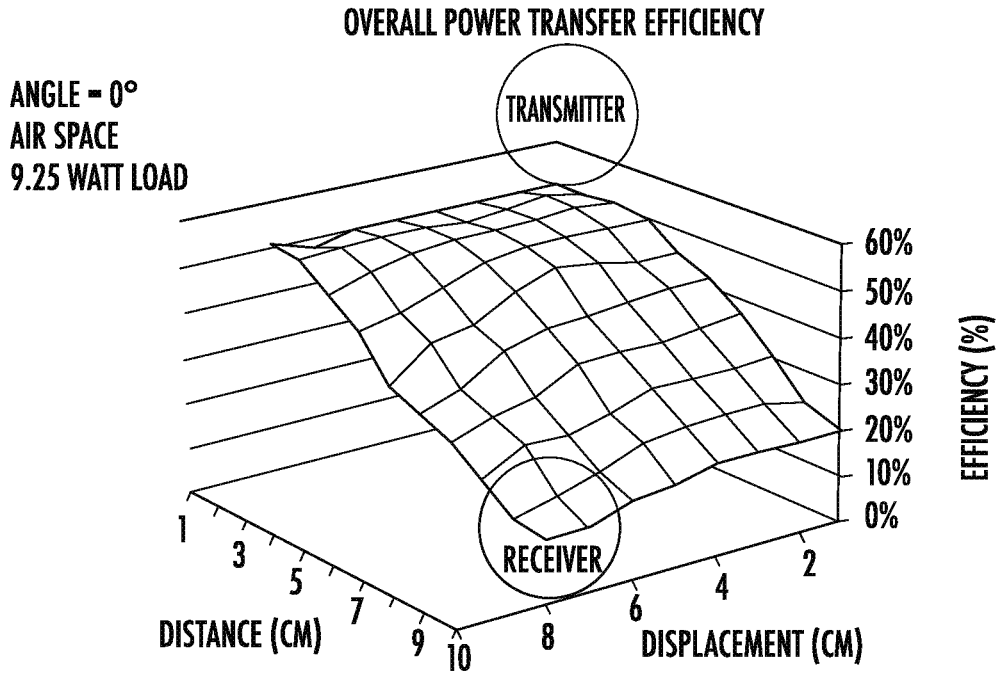
FIG. 39 is a graph of the power transfer efficiency of the wireless power system with varying distances and displacements between transmitter and receiving coils.

In addition, Applicant conducted a number of tests wherein the distance and the displacement (i.e., the distance of offset from coil centers) between the receiving and transmitter coils was adjusted to account for suboptimal placement of the coils. Ideally, the transmitting and receiving coils are positioned about 2 cm apart with a coil center offset of zero or close to zero. The system has been designed to provide at least 50% power delivery efficiency in the event that these optimal values are not met. For example, if the patient does not position the transmitting coil in the optimal location and orientation relative to the receiving coil. The results of this testing is shown in FIG. 39. As shown, the efficiency of the coils remained at or above 50% even when the coils were separated by 4 cm and offset by 4 cm. Thus, the wireless system described herein is capable of generating a ratio of output power to input power or efficiency of greater than 50% even when the coils are positioned up to 4 cm apart and the centers of the coils are offset by up to 4 cm.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications, and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A system for supporting cardiac function in a patient, the system comprising:

a housing configured for implantation into a human heart or vascular system, the housing comprising a motor and a pump, wherein the pump comprises a rotor disposed within the housing and spaced from an internal surface of the housing to define a clearance therebetween, an impeller coupled to the rotor for impelling blood from the inlet to the outlet of the housing and a fluid bearing suspending the impeller and the rotor within the housing, wherein the housing comprises an inlet and an outlet and defines a primary blood flow path between the inlet and the outlet, and further comprising a second inlet for blood within the housing fluidly coupled to the clearance between the rotor and the housing to define a secondary flow path through the clearance and wherein the primary blood flow path has a first mass flow rate and the secondary blood flow path has a second mass flow rate, wherein the second mass flow rate is 1% to 20% of the first mass flow rate;

an external power source;

a transmitting antenna coupled to the external power source and comprising at least one magnetic coil, wherein the external power source transmits a first level of power to the transmitting antenna and the transmitting antenna is configured to transmit a second level of power through an outer skin surface of the patient;

a receiving antenna configured for implantation within the patient, the receiving antenna comprising at least one magnetic coil and being configured to receive the second level of power and to transmit a third level of power to the housing, wherein the third level of power is at least 40% of the first level of power.

2. The system of claim 1, wherein the third level of power is at least 50% of the first level of power.

3. The system of claim 1, further comprising a controller coupled to the transmitting antenna and configured to control the transmitting and receiving antenna such that the third level of power remains at or above a threshold level.

4. The system of claim 3, wherein the controller maintains the third level of power at least 50% of the first level of power when the transmitting is moved a distance towards or away from the receiving coil.

5. The system of claim 4, wherein the distance is 4 cm.

6. The system of claim 3, wherein the controller is configured to maintain the third level of power constant.

7. The system of claim 1, wherein the controller maintains the third level of power at least 50% of the first level of power when a center of the transmitting coil is offset a distance from a center of the receiving coil.

8. The system of claim 7, wherein the distance is 4 cm.

9. The system of claim 1, wherein the first level of power is 10 Watts to 40 Watts.

10. The system of claim 1, wherein the second level of power is 15 Watts to 30 Watts.

11. The system of claim 1, wherein the third level of power is 5 Watts to 20 Watts.

12. The system of claim 1, wherein the transmitting and receiving coils are configured to have a specific absorption rate (SAR) in an touter skin surface of the patient of 1.5 Watts/kg or less.

13. The system of claim 1, wherein the transmitting coil is flexible.

14. The system of claim 1, wherein the transmitting coil comprises an outer surface and a spiral winding on the outer surface.

15. The system of claim 14, wherein the spiral winding comprises first and second discontinuous windings, wherein the first winding is-concentric with the second winding.

16. The system of claim 1, wherein the receiving coil comprises an outer surface and a spiral winding on the outer surface.

17. The system of claim 16, wherein the spiral winding is continuous.

18. The system of claim 16, wherein the spiral winding comprises first and second discontinuous windings, wherein the first winding is concentric with the second winding.

19. The system of claim 1, further comprising a receiving resonator disposed within the housing.

20. The system of claim 1, further comprising a wearable device configured to be attached to, or worn by, the patient, wherein the transmitting antenna is housed within the wearable device.

21. The system of claim 1, further comprising a transmitter antenna and a receiving antenna configured to form a magnetically coupled resonator (MCR) by matching a resonance frequency between the transmitter resonator and the receiver resonator.

22. The system of claim 1, wherein the housing is configured for implantation into a right atrium of the patient, the housing having an inlet and an outlet spaced longitudinally from the inlet, the inlet and the outlet defining a primary blood flow path from a left atrium through at least a portion of the housing to an aorta.

23. The system of claim 1, wherein the rotor and the impeller are spaced from the internal surface of the housing and at least partially supported with hydrodynamic forces within the housing.

24. The pump of claim 1, wherein the fluid bearing comprises one or more surfaces that create a fluid pressure that resists axial forces generated by the impeller or the rotor.

25. The pump of claim 1, wherein the fluid bearing comprises one or more surfaces that create a fluid pressure that resists radial forces generated by the impeller or the rotor.

26. The pump of claim 1, wherein the secondary blood flow path is in an opposite direction as the primary blood flow path.

27. The pump of claim 1, wherein the second mass flow rate is about 5% to about 10% of the first mass flow rate.

* * * * *